(12) United States Patent
Garrett et al.

(10) Patent No.: US 8,301,398 B2
(45) Date of Patent: Oct. 30, 2012

(54) STRUCTURE OF THE INSULIN RECEPTOR ECTODOMAIN

(75) Inventors: Thomas P. J. Garrett, Brunswick (AU); Timothy Edward Adams, Lower Plenty (AU); George Lovrecz, Balwyn North (AU); Neil Moreton McKern, Lilydale (AU); Michael Colin Lawrence, Newport (AU); Lindsay Gale Sparrow, Canterbury (AU); Colin Wesley Ward, Carlton North (AU); Meizhen Lou, Scoresby (AU); Victor Strelstov, Templestowe (AU)

(73) Assignee: Walter and Eliza Hall Institute of Medical Research, Parkville (AU)

( * ) Notice: Subject to any disclaimer, the term of this patent is extended or adjusted under 35 U.S.C. 154(b) by 336 days.

(21) Appl. No.: 12/305,951

(22) PCT Filed: Jun. 22, 2007

(86) PCT No.: PCT/AU2007/000869
§ 371 (c)(1),
(2), (4) Date: Jun. 15, 2010

(87) PCT Pub. No.: WO2007/147213
PCT Pub. Date: Dec. 27, 2007

(65) Prior Publication Data
US 2010/0267927 A1    Oct. 21, 2010

(30) Foreign Application Priority Data
Jun. 22, 2006 (AU) ................. 2006903378

(51) Int. Cl.
*C07K 14/00* (2006.01)
*G01N 33/00* (2006.01)
*G01N 23/02* (2006.01)
(52) U.S. Cl. ............................ 702/27; 436/86; 530/350
(58) Field of Classification Search ....................... None
See application file for complete search history.

(56) References Cited

FOREIGN PATENT DOCUMENTS
WO      WO 00/73793      *    7/2000

OTHER PUBLICATIONS

Wiencek, J. M. New Strategies for protein crystal growth. Ann. Rev. Biomed. Eng. 1999, 1, 505-534.*
Hubbard, S. Crystal structure of the activated insulin recptor tyrosine kinase in complex with peptide substrate and ATP analog.EMBO J. 1997, 16 (18), 5573-5581.*
Accili, D., Mosthaf, L., Ullrich, A. & Taylor, S.I. (1991). A mutation in the extracellular domain of the insulin receptor impairs the ability of insulin to stimulate receptor autophosphorylation, J.Bio. Chem., 226, 434-439.
Adams, T.E., Epa, V.C., Garrett, T.P.J. & Ward, C.W. (2000). Structure and function of the type 1 insulin-like growth factor receptor, Cell. Molec. Life Sci., 57, 1050-1093.

(Continued)

Primary Examiner — Nashaat Nashed
(74) Attorney, Agent, or Firm — DLA Piper LLP (US)

(57) ABSTRACT

The present invention relates to the crystal structure of the insulin receptor ectodomain, to the nature of its N-linked glycans and to methods of using the crystal and related structural information to screen for and design compounds that interact with or modulate the insulin receptor and/or the closely-related insulin-like growth factor receptors or variants thereof.

24 Claims, 17 Drawing Sheets

OTHER PUBLICATIONS

Andersen, A.S., Kjeldsen, T., Wiberg, F.C., Vissing, H., Schaffer, L., Rasmussen, J.S., De-Meyts, P. & Moller, N.P.H. (1992). Identification of determinants that confer ligand specificity on the insulin receptor, J. Biol.Chem., 267, 13681-13686.

Apfel, S.C. (1999). Neurotrophic factors in the therapy of diabetic neuropathy, Am. J. Med., 107, 34S-42S.

Auer, R.N. (1998). Insulin, blood glucose levels, and ischemic brain damage. Neurology, 51, S39-S43.

Bailyes, E.M., Nave, B.T., Soos, M.A., Orr, S.R., Hayward, A.C. & Siddle, K. (1997). Insulin receptor/IGF-I receptor hybrids are widely distributed in mammalian tissues: quantification of individual receptor species by selective immunoprecipitation and immunoblotting, Biochem. J., 327, 209-215.

Bajaj, M., Waterfield, M.D., Schlessinger, J., Taylor, W.R. & Blundell, T. (1987). On the tertiary structure of the extracellular domains of the epidermal growth factor and insulin receptors, Biochim. Biophys. Acta, 916, 220-226.

Bartlett et al, (1989). CAVEAT: A Program to Facilitate the Structure-Derived Design of Biologically Active Molecules, in Molecular Recognition in Chemical and Biological Problems, Special Pub., Royal Chem. Soc, 78, 182-196.

Bayne, M.L., Applebaum, J., Chicchi, G.G., Hayes, N.S., Green, B.G. & Cascieri, M.A. (1988). Structural analogs of human insulin-like growth factor I with reduced affinity for serum binding proteins and the type 2 insulin-like growth factor receptor, J. Biol. Chem., 263, 6233-6239.

Bentley, G.A. (1997). Phased translation function, Meth. Enzym., 276, 611-619.

Binz, H.K., Amstutz, P. & Pluckthun, A. (2005). Engineering novel binding proteins from nonimmunoglobulin domains, Nature Biotechnology, 23, 1257-1268.

Blanc, E., Roversi, P., Vonrhein, C., Flensburg, C., Lea, S.M. & Bricogne, G. (2004). Refinement of severely incomplete structures with maximum likelihood in BUSTER-TNT, Acta Crystallogr. D. Biol. Crystallogr., 60, 2210-2221.

Blondelle, S.E. & Houghten, R.A. (1996). Novel antimicrobial compounds identified using synthetic combinatorial library technology, Trends Biotechnol., 14, 60-65.

Bohm & Stahl (1999). M. Med. Chem. Res., 9, 445.

Bohne-Lang, A. & von der Leith, C.W. (2005). GlyProt: *in silico* glycosylation of proteins. Nucl. Acids Res. 33, W214-219.

Brandt, J., Andersen, A.S. & Kristensen, C. (2001). Dimeric fragment of the insulin receptor alpha-subunit finds insulin with full holoreceptor affinitym, J. Biol. Chem., 276, 12378-12384.

Bricogne, G. (1997). Bayesian statistical viewpoint on structure determination: basic concepts and examples, Methods Enzymol., 276, 361-423.

Brooks, B.R., Bruccoleri, R.E., Olafson, B.D., States, D.J., Swaminathan, S. & Karplus, J.M. (1983). Comp. Chem., 4, 187-217.

Brunger, A.T., Adams, P.D., Clore, G.M., DeLano, W.L., Gros, P., Grosse-Kunstleve, R.W., Jiang, J.S., Kuszewski, J., Nilges, M., Pannu, N.S., Read, R.J., Rice, L.M., Simonson, T. & Warren, G.L. (1998). Crystallography and NMR system: A new software suite for macromolecular structure determination, Acta Crystallogr. D. Biol. Crystallogr., 54, 905-921.

Brunger (1997). Meth. Enzym., 276, 558-580.

Burgess & Leach (1973a). Biopolymers, 12(12), 2691-2712.

Burgess & Leach (1973b). Biopolymers, 12(11), 2599-2605.

Burgess, A.W., Cho, H-S., Eigenbrot, C., Ferguson, K. M., Garrett, T.P.J., Leahy, D.J., Lemmon, M.A., Sliwkowski, M.X., Ward, C.W. & Yokoyama, S. (2003). An open-and-shut case? Recent insights into the activation of EGF/ErbB receptors, Molecular Cell, 12, 541-552.

Butt et al. (1999). Immunol. Cell Biol., 77, 256-262.

Carell et al. (1994a). Angew. Chem. Int. Ed. Engl., 33, 2059.

Carell et al. (1994b). Angew. Chem. Int. Ed. Engl., 33, 2061.

Chakravarty, A.; Hinrichsen, J.; Whittaker, L. & Whittaker, J. (2005). Rescue of ligand binding of a mutant IGF-I receptor by complementation, Biochem. Biophys. Res. Commun., 331, 74-77.

Chan, S.J., et al. (2007). Complementation Analysis Demonstrates That Insulin Cross-links Both α-Subunits in a Truncated Insulin Receptor Dimer. J. Biol. Chem. 282:13754-13758.

Cho et al. (1993). Science, 261, 1303.

Chow et al. (1998). Biol. Chem., 273, 4672-4680.

Clarke et al. (2000). Cancer Res., 60, 4804-4811.

Cohen et al. (1990). Molecular Modeling Software and Methods for Medicinal Chemistry, J. Med. Chem., 33, 883-894.

Cowtan, K.D. (1994). 'dm': An automated procedure for phase improvement by density modification, Joint CCP4 and ESF-EACBM newsletter on protein crystallography 31, 9-14.

Cull et al. (1992). Proc. Natl. Acad. Sci. USA, 89, 1865-1869.

Cwirla et al. (1990). Proc. Natl. Acad. Sci. USA, 97, 6378-6382.

de la Fortelle, E. & Bricogne, G. (1997). Maximum-likelihood heavy-atom parameter refinement for multiple isomorphous replacement and multiwavelength anomalous diffraction methods, Methods Enzymol., 276, 472-494.

De Meyts, P., Gu, J-L., Shymko, R.M., Kaplan, B.E., Bell, G.I. & Whittaker, J. (1990). Identification of a ligand-binding region of the human insulin receptor encoded by the second exon of the gene, Molecular Endocrinol., 4, 409-416.

De Meyts, P. (1994). The structural basis of insulin and IGF-1 Receptor binding and negative co-operativity, and its relevance to mitogenic versus metabolic signaling, Diabetologia, 37 (Suppl 2), S135-S148.

De Meyts, P. & Whittaker, J. (2002). Structural biology of insulin and IGF1 receptors: implications for drug design, Nat. Rev. Drug Discov., 1, 769-783.

De Meyts, P. (2004). Insulin and its receptor: structure, function and evolution, Bioessays, 26, 1351-1362.

DeWitt et al. (1993). Proc. Natl. Acad. Sci. USA, 90, 6909.

Denley, A., Wallace, J.C., Cosgrove, L.J. & Forbes, B.E. (2003). The insulin receptor isoform exon 11—(IR-A) in cancer and other diseases: a review, Horm. Metab. Res., 35, 778-785.

Denley, A., Bonython, E.R., Booker, G.W., Cosgrove, L.J., Forbes, B.E., Ward, C.W. & Wallace, J.C. (2004). Structural determinants for high-affinity binding of insulin-like growth factor II to insulin receptor (IR)-A, the exon 11 minus isoform of the IR, Mol. Endocrinol., 18, 2502-2512.

Derewenda, U., Derewenda, Z., Dodson, E.J., Dodson, G.G., Bing, X. & Markussen, J. (1991). X-ray analysis of the single chain B29-A1 peptide-linked insulin molecule. A completely inactive analogue, J. Mol. Biol., 220, 425-433.

Devlin (1990). Science, 249, 404-406.

Emsley. P. & Cowtan, K. (2004). Coot: model-building tools for molecular graphics, Acta Crystallographica, Section D-Biological Crystallography, 60, 2126-2132.

Erb et al. (1994). Proc. Natl. Acad. Sci. USA, 91, 11422.

Evan. G.I.; Lewis, G.K.; Ramsay, G. & Bishop, J.M. (1985). Isolation of monoclonal antibodies specific for human c-myc proto-oncogene product, Mol. Cell Biol., 5, 3610-3616.

Ewing et al. (2001). J. Comput-Aid. Mol. Design, 15, 411.

Fabry. M., Schaefer, E., Ellis, L., Kojro, E., Fahrenholz, F. & Brandenburg, D. (1992). Detection of a new hormone contact site within the insulin receptor ectodomain by the use of a novel photoreactive insulin, J. Biol. Chem., 267, 8950-8956.

Felici (1991). J. Mol. Biol., 222, 301-310.

Florke, R.R., Schnaith, K., Passlack, W., Wichert, M., Kuehn, L., Fabry, M., Federwisch, M. & Reinauer, H. (2001). Hormone-triggered conformational changes within the insulin-receptor ectodomain: requirement for transmembrane anchors. Biochem. J., 360, 189-198.

Fodor (1993). Nature, 364, 555-556.

Frank et al. (1999). J. Struct. Biol., 116, 190-199.

Garrett, T.P.J., McKern, N.M., Lou M, Frenkel, M.J., Bentley, J.D., Lovrecz, G.O., Elleman T.C., Cosgrove, L.J. & Ward, C.W. (1998). Crystal structure of the first three domains of the type-1 insulin-like growth factor receptor, Nature, 394, 395-399.

Gallop et al. (1994). J. Med. Chem., 37, 1233.

Gilliland, L.K., Norris, N.A., Marquardt, H., Tsu, T.T., Hayden, M.S., Neubauer, M.G., Yelton, D.E., Mittler, R.S. & Ledbetter, J.A. (1996). Rapid and reliable cloning of antibody variable regions and generation of recombinant single chain antibody fragements, Tissue Antigens. 47, 1-20.

Goodford, P.J. (1985). A Computational Procedure for Determining Energetically Favorable Binding Sites on Biologically Important Macromolecules, J. Med. Chem., 28, 849-857 (1985).

Goodsell, D. S. & Olsen, A.J. (1990). Automated Docking of Substrates to Proteins by Simulated Annealing. Proteins: Structure, Function, and Genetics, 8, 195-202.

Grønskov, K., Vissing, H., Shymko, R.M., Tornqvist, H. & De Meyts, P. (1993). Mutation of arginine 86 to proline in the insulin receptor alpha subunit causes lack of transport of the receptor to the plasma membrane, loss of binding affinity and a constitutively activated tyrosine kinase in transfected cells, Biochem. Biophys. Res. Commun., 192, 905-911.

Guida, W.C. (1994). Software for Structure-Based Drug Design, Curr. Opin. Struct. Biology, 4, 777-781.

Gustafson, T.A. & Rutter, W.J. (1990). The cysteine-rich domains of the insulin and insulin-like growth factor 1 receptors are primary determinants of hormone binding specificity. J. Biol. Chem., 265, 18663-18667.

Houghten et al. (1991). Nature, 354, 84-86.

Houghten (1992). Biotechniques, 13, 412-421.

Hoyne, P.A., Elleman. T.C., Adams, T.E., Richards, K.M. & Ward, C.W. (2000). High affinity insulin binding by soluble insulin receptor extracellular domain fused to a leucine zipper. FEBS Letters, 479, 15-18.

Hua, Q.X., Shoelson, S.E., Kochoyan, M. & Weiss, M.A. (1991). Receptor binding redefined by a structural switch in a mutant human insulin, Nature, 354, 238-241.

Huang, K., Xu, B., Hu, S.Q., Chu, Y.C., Hua, Q.X., Qu, Y., Li, B., Wang, S., Wang, R.Y., Nakagawa, S.H., Theede, A.M., Whittaker, J., De Meyts, P., Katsoyannis, P.G. & Weiss, MA. (2004). How insulin binds: the B-chain alpha-helix contacts the L1 beta-helix of the insulin receptor, J. Moi. Biol., 341, 529-550.

Jancarik, J. & Kim. S.-H. (1991). Sparse matrix sampling: a screening method for crystallization of proteins, J. Appl. Cryst., 24, 409-411.

Jones, T.A., Zou. J.Y., Cowan, S.W. & Kjeldgaard (1991). Improved methods for finding protein models in electron density maps and the location of errors in these models, Acta Cryslallogr., A 47, 110-119.

Kadowaki, H., Kadowaki, T., Cama, A., Marcus-Samuels, B., Rovira, A., Bevins, C.L. & Taylor, S.I. (1990). Mutagenesis of Lysine 460 in the human insulin receptor: effects upon receptor recycling and cooperative interactions among binding sites, J. Biol. Chem., 265, 21285-21296.

Kitamura, T., Kahn, C.R. & Accili, D. (2003). Insulin receptor knockout mice. Annu Rev Physiol., 65, 313-332.

Kjeldsen. T., Andersen, A.S., Wiberg F.C., Rasmussen J.S., Schaffer L., Balschmidt P., Moller, K.B. & Moller N.P. (1991). The ligand specificities of the insulin receptor and the insulin-like growth factor I receptor reside in different regions of a common binding site, Proc. Natl. Acad. Sci. USA, 88, 4404-4408.

Kjeldsen T., Wiberg, F.C. & Andersen, A.S. (1994). Chimeric receptors indicate that phenylalanine 29 is a major contributor to insulin specificity of the insulin receptor, J. Biol. Chem., 269, 32942-32946.

Kleywegt, G.J. & Jones, T.A. (1994). A super position. CCP4/ESF-EACBM, Newsletter on Protein Crystallography, 31, 9-14.

Kobayashi, M., Takata. Y., Ishibashi, O., Sasaoka, T., Iwasaki, T.M., Shigeta, Y. & Inouye, K. (1986). Receptor binding and negative cooperativity of a mutant insulin, Biochem. Biophys. Res. Commun., 137, 250-257.

Kristensen, C., Kjeldsen, T., Wiberg, F.C., Schaffer, L., Hach, M., Havelund, S., Bass. J., Steiner, D.F. & Andersen, A.S. (1997). Alanine scanning mutagenesis of insulin. J. Biol, Chem., 272, 12978-12983.

Kristensen, C., Wiberg, P. C. & Andersen, A. S. (1999). Specificity of insulin and insulin-like growth factor I receptors investigated using chimeric mini-receptors—Role of C-terminal of receptor alpha subunit, J. Biol. Chem., 274, 37351-37356.

Kristensen, C., Wiberg, F.C., Schäffer, L. & Andersen, A.S. (1998). Expression and characterization of a 70-kDa fragment of the insulin receptor that binds insulin, J. Biol. Chem., 273, 17780-17786.

Kuntz, I.D., Blaney, J.M., Oatley, S.J., Langridge, R. & Ferrin, T.E. (1982). A Geometric Approach to Macromolecule-Ligand Interactions, J. Mol. Biol., 161, 269-288.

Kurose, T., Pashmforoush, M., Yoshima,Y., Carroll, R., Schwartz, G.P., Burke, G.T., Katsoyannis. P.G. & Steiner, D.F. (1994). Cross-linking of a B25 azidophenylalanine insulin derivative to the carboxy-terminal region of the alpha-subunit of the insulin receptor, identification of a new insulin-binding domain in the insulin receptor, J. Biol. Chem., 269, 29190-29197.

Jones, T.A., Zou, J.Y., Cowan, S.W. & Kjeldgaard (1991). Improved methods for binding protein models in electron density maps and the location of errors in these models. Acta Crystallogr. A., 47, 110-119.

Laemmli, U.K. (1970). Cleavage of structural proteins during the assembly of the head of bacteriophage T4, Nature, 227, 680-685.

Lam et al. (1991). Nature, 354, 82-84.

Lam, K.S. (1997). Anticancer Drug Des., 12, 145.

Lattman (1985). Use of the Rotation and Translation Functions, Meth. Enzymol., 115, 55-77.

Lee, J., Pilch, P.F., Shoelson, S.E. & Scarlata, S.F. (1997). Conformational changes of the insulin receptor upon insulin binding and activation as monitored by fluorescence spectroscopy, Biochemistry, 36, 2701-2708.

Liu J.P., Baker, J., Perkins. A.S., Robertson, E.J., & Efstratiadis, A. (1993). Mice carrying null mutations of the genes encoding insulin-like growth factor I (Igf-1) and type 1 IGF receptor (Igf1r), Cell 75, 59-72.

Ludvigsen. S., Olsen, H.B. & Kaarsholm, N.C. (1998). A structural switch in a mutant insulin exposes key residues for receptor binding, J. Mol. Biol., 279, 1-7.

Luo, R.Z.T., Beniac, D.R., Fernandes, A., Yip, C.C. & Ottensmeyer, F.P. (1999). Quaternary structure of the insulin-insulin receptor complex, Science, 285, 1077-1080.

Lütteke, T, Frank, M. & von der Leith, C.W. (2005). Carbohydrate Structure Suite (CSS): analysis of carbohydrate 3D structures derived from the PDB.

Lütteke, T., Bohne-Lang, A., Loss, A., Goetz, T,, Frank, M. & von der Lieth, C.W. (2006). Glycosciences de: an Internet portal to support glycomics and glycobiology research., Glycobiology 16, 71R-81R.

Marino-Buslje, C., Mizuguchi, K., Siddle, K. & Blundell, T.L. (1998). A third fibronectin type III domain in the extracellular region of the insulin receptor family, FEBS Lett. 441, 331-336.

Marino-Buslje, C., Martin-Martinez, M., Mizuguchi, K., Siddle, K. & Blundell, T.L. (1999). The insulin receptor: from protein sequence to structure, Biochem. Soc. Trans., 27, 715-726.

Marsh BJ., Alm, R.A., Mcintosh S.R. & James, D.E. (1995). Molecular regulation of GLUT-4 targeting in 3T3-L1 adipocytes, *J. Cell Biol.*, 130, 1081-1091.

Martin (1992). 3D Database Searching in Drug Design, J. Med. Chem., 35, 2145-2154.

McCoy, A.J., Grosse-Kunstleve, R.W., Storoni, L.C. & Read, R.J. (2005). Likelihood-enhanced fast translation functions, Acta Crystallogr. D. Biol. Crystallogr., 61, 458-464.

McKern, N.M., Lou, M., Frenkel, M.J., Verkuylen, A., Bentley, J.D., Lovrecz, G.O., Ivancic. N., Elleman, T.C., Garrett, T.P.J., Cosgrove, L. & Ward, C.W. (1997). Crystallization of the first three domains of the human insulin-like growth factor-1 receptor, Protein Sci., 6, 2663-2666.

McRee, D.H. (1999). XtalView/Xfit—a versatile program for manipulating atomic coordinates and electron density, J. Struct. Biol., 125, 156-165.

Miranker, A. & Karplus, M. (1991). Functionality Maps of Binding Sites: A Multiple Copy Simultaneous Search Method, Proteins: Structure, Function and Genetics, 11, 29-34.

Moody et al. (1974). Horm. Metab. Res., 6(1), 12-6.

Morton, T.A. & Myszka, D.G. (1998). Kinetic analysis of macromolecular interactions using surface plasmon resonance biosensors, *Methods Enzymol.*, 295, 268-294.

Mulhern, T.D., Booker, G.W. & Cosgrove, L. (1998). A third fibronectin type-III domain in the insulin-family receptors. TIBS, 23, 465-466.

Murshudov, G.N., Vagin, A.A. & Dodson, E.J. (1997). Refinement of Macromolecular Structures by the Maximum-Likelihood, Method Acta Cryst., D53, 240-255.

Mynarcik, D.C., Yu, G.Q. & Whittaker. J. (1996). Alanine-scanning mutagenesis of a C-terminal ligand binding domain of the insulin receptor alpha subunit., J. Biol. Chem., 271, 2439-2442.

Mynarcik, D.C., Williams. P.F., Schaffer, L., Yu, G.Q. & Whittaker, J. (1997a). Analog binding properties of insulin receptor mutants—identification of amino acids interacting with the COOH terminus of the B-chain of the insulin molecule, J. Biol. Chem., 272, 2077-2081.

Mynarcik, D.C., Williams, P.F., Schaffer. L., Yu, G.Q. & Whittaker, J. (1997b). Identification of common ligand binding determinants of the insulin and insulin-like growth factor 1 receptors—insights into mechanisms of ligand binding, J. Biol. Chem., 272, 18650-18655.

Nakae, J., Morioka, H., Ohtsuka, E. & Fujieda, K. (1995). Replacements of leucine 87 in human insulin receptor alter affinity for insulin, J. Biol. Chem., 270, 22017-22022.

Nakagawa. S.H. & Tager, H.S. (1989). Perturbation of insulin-receptor interactions by intramolecular hormone cross-linking. Analysis of relative movement among residues A I. BI and B29. J. Biol. Chem., 264. 272-279.

Nakagawa, S.H. & Tager, H.S. (1992). Importance of aliphatic side-chain structure at positions 2 and 3 of the insulin A chain in insulin-receptor interactions, Biochemistry, 31, 3204-3214.

Nakagawa. S.H., Tager, H.S. & Steiner. D.F. (2000). Mutational analysis of invariant valine B12 in insulin: Implications for binding, Biochemistry 39, 15826-15835.

Nice, EC. & Catimel, B. (1999). Instrumental biosensors: new perspectives for the analysis of biomolecular interactions. Bioessays, 21, 339-352.

Nicholls. A., Sharp, K. & Honig. B. (1991). Protein Folding and Association: Insights from the Interfacial and thermodynamic properties of hydrocarbons, Proteins: Struct. Funct. Genet., 11, 281-295.

Navia & Murcko (1992). The Use of Structural Information in Drug Design, Curr. Opin. Struct. Biol., 2, 202-210.

Navaza & Saludjian (1997). Meth. Enzym., 276, 581-594.

O'Bryan, J.P., Frye, R.A., Cogswell, P.C., Neubauer, Z., Kitch, B., Prokop, C., Espinosa III, R., Le Beau, M.M., Earp, H.S. & Liu, L.T. (1991). Axl, a transforming gene isolated from primary human myeloid leukemia cells, encodes a novel receptor tyrosine kinase, Molec. Cell. Biol., 11, 5016-5031.

O'Donohue et al. (1995). Protein Sci., 4(10), 2191-2202).

Olefsky, J.M. (1978). Mechanisms of the ability of insulin to activate the glucose-transport system in rat adipocytes, Biochem. J., 172, 137-145.

Ottensmeyer, F.P., Beniac, D.R., Luo, R.Z.T. & Yip, C.C. (2000). Mechanism of transmembrane signaling: Insulin binding and the insulin receptor, Biochemistry, 39, 12103-12112.

Ottensmeyer, F.P:, Beniac. D.R., Luo, R.2.T. & Yip, C.C. (2001). Mechanism of transmembrane signaling: Insulin binding and the insulin receptor, Biochemistry, 40, 6988-6988.

Otwinowski, Z. & Minor, W. (1997). Processing of X-ray diffraction data collected in oscillation mode, Methods Enzymol., 276, 307-326.

Peng, K., Vucetic, S., Radivojac, P., Brown, C.J., Dunker, A.K. & Obradovic, Z. (2005). Optimizing long intrinsic disorder predictors with protein evolutionary information, J. Bioinformatics Comput. Biol., 3, 35-60.

Pflugrath, J.W. (1999). The finer things in X-ray diffraction data collection, Acta Crystallogr. D. Biol. Crystallogr., 55. 1718-1725.

Pillutla, R.C., Hsiao, K.C., Beasley, J.R., Brandt, J., Ostergaard, S., Hansen, P.H., Spetzler, J.C., Danielsen, G.M., Andersen, A.S., Brissette, R.E., Lennick, M., Fletcher, P.W., Blume. A.J., Schaffer, L. & Goldstein, N.I. (2002). Peptides identify the critical hotspots involved in the biological activation of the insulin receptor, J. Biol. Chem., 277, 22590-22594.

Pitt, J.J. & Gorman, J.J. (1996). Matrix-assisted laser desorption/ionization time-of-flight mass spectrometry of sialylated glycopeptides and proteins using 2,6-dihydroxyacetophenone as a matrix, Rapid Commun. Mass Spectrom., 10, 1786-1788.

Pitt, J.J. & Gorman, J.J. (1997). Oligosaccharide characterization and quantitation using 1-phenyl-3-methyl-5-pyrazolone derivatization and matrix-assisted laser desorption/ionization time-of-flight mass spectrometry, Anal. Biochem., 248, 63-75.

Prigent, S.A., Stanley, K.K. & Siddle, K. (1990). Identification of epitopes on the human insulin receptor reacting with rabbit polyclonal antisera and mouse monoclonal antibodies, J. Biol. Chem., 265, 9970-9977.

Pullen, R.A., Lindsay. D.G., Wood, S.P., Tickle, I.J., Blundell, T.L., Wollmer, A., Krail, G., Brandenburg, D., Zahn, H., Gliemann, J. & Gammeltoft, S. (1976). Receptor binding region of insulin, Nature, 259, 369-373.

Rarey, M. et al. (1996). J. Mol. Biol., 261, 470.

Robinson, L.J. & James, D.E. (1992). Insulin-regulated sorting of glucose transporters in 3T3-L1 adipocytes, Am. J. Physiol., 263, E383-E393.

Rouard, M., Bass. J., Grigorescu, F., Garrett, T.P.J., Ward, C.W., Lipkind, G., Jaffiole, C, Steiner, D. F. & Bell, G.I. (1999). Congenital insulin resistance associated with a conformational alteration in a conserved beta-sheet in the insulin receptor L1 domain, J. Biol. Chem., 274, 18487-18491.

Sali and Blundell (1993). J. Mol. Biol., 234, 779-815.

Schaefer, E.M., Erickson. H.P., Federwisch. M., Wollmer, A. & Ellis, L. (1992). Structural organization of the human insulin receptor ectodomain, J. Biol. Chem., 267, 23393-23402.

Schaffer, L. (1994). A model for insulin binding to the insulin receptor, Eur. J. Biochem., 221, 1127-1132.

Schaffer, L., Brissette, R.E., Spetzler, J.C., Pillutla, R.C., Ostergaard, S., Lennick, M., Brandt. J., Fletcher, P.W., Danielsen, G.M., Hsiao, K.C., Andersen, A.S., Dedova, O., Ribel, U., Hoeg-Jensen, T., Hansen, P.H., Blume, A.J., Markussen, J. & Goldstein, N.I. (2003). Assembly of high-affinity insulin receptor agonists and antagonists from peptide building blocks, Proc. Natl. Acad. Sci. USA, 100, 4435-4439.

Schaefer, E.M., Siddle K. & Ellis, L. (1990). Deletion analysis of the human insulin receptor ectodomain reveals independently folded soluble subdomains and insulin binding by a monomeric A-subunit, J. Biol. Chem., 265, 13248-13253.

Schlehuber, S. & Skerra, A. (2005). Lipocalins in drug discovery: from natural ligand-binding proteins to 'anticalins', Drug Disc. Today, 10, 23-33.

Schumacher, R., Mosthaf. L., Schlessinger, J., Brandenburg, D. & Ullrich, A. (1991). Insulin and insulin-like growth factor-1 binding specificity is determined by distinct regions of their cognate receptors, J. Biol. Chem, 266, 19288-19295.

Schumacher. R., Soos, M.A., Schlessinger, J., Brandenburg, D., Siddle, K. & Ullrich, A. (1993). A. Signaling-competent receptor chimeras allow mapping of major insulin receptor binding domain determinants., J. Biol. Chem., 268, 1087-1094.

Scott & Smith (1990). Science, 249, 386-390.

Silverman, J., Liu, Q., Bakker, A., To, W., Duguay, A., Alba, B.M., Smith, R., Rivas, A., Li, P., Le, H., Whitehorn, E., Moore, K.W., Swimmer, C, Periroth, V., Vogt, M., Kolkman. J. & Stemmer, W.P. (2005). Multivalent avimer proteins evolved by exon shuffling of a family of human receptor domains, Nature Biotechnology, 23, 1556-1561.

Sitkoff, D., Lockhari. DJ., Sharp, K.A. & Honig, B. (1994). Calculation of electrostatic effects at the amino terminus of an alpha helix, Biophys. J., 67, 2251-2260.

Smith et al. (1999). Nat. Med., 5, 1390-1395.

Songyang et al. (1993). Cell, 72, 767-778.

Soos, M.A., Siddle, K., Baron. M.D., Heward, J.M., Luzio, J.P., Bellatin, J. & Lennox, E.S. (1986). Monoclonal antibodies reacting with multiple epitopes on the human insulin receptor, Biochem. J., 235, 199-208.

Sparrow, L.G., McKern, N.M., Gorman, J.J., Strike, P.M., Robinson, C.P., Bentley, J.D. & Ward, C.W. (1997). The disulfide bonds in the C-terminal domains of the human insulin receptor ectodomain, J. Biol. Chem., 272, 29460-29467.

Sparrow, L.G., Gorman, J.J., Strike, P.M., Robinson, C.P., McKern, N.M., Epa, V.C., & Ward, C.W. (2006). The location and characterisation of the O-linked glycans of the human insulin receptor, Protein Sci., Submitted.

Spellman, M.W., Basa, L.J., Leonard, C.K., Chakel, J.A., O'Connor, J.V., Wilson, S. & van Halbeek, H. (1989). Carbohydrate structures of human tissue plasminogen activator expressed in Chinese hamster ovary cells, J. Biol. Chem., 264, 14100-14111.

Stanley, P. (1989). Chinese hamster ovary cell mutants with multiple glycosylation defects for the production of glycoproteins with minimal carbohydrate heterogeneity, Molec. Cellul. Biol., 9, 377-383.

Surinya, K.H., Molina, L, Soos, M. A., Brandt. J., Kristensen, C. & Siddle, K. (2002). Role of insulin receptor dimerization domains in ligand binding, cooperativity, and modulation by anti-receptor antibodies, J. Biol. Chem., 277, 16718-16725.

Terwilliger. T.C. (2000) Maximum-likelihood density modification, Acta Crystallogr D Biol Crystallogr, 56, 965-972.

Tong and Rossmann. (1997). Meth. Enzym., vol. 276, pp. 594-611.

Tulloch, P.A., Lawrence, L.J., Mckern, N.M., Robinson, C.P., Bentley, J.D., Cosgrove, L., Ivancic, N., Lovrecz, G.O., Siddle, K., and Ward, C.W. (1999). Single-molecule imaging of human insulin receptor ectodomain and its Fab complexes, J. Struct. Biol. 125, 11-18.

Ullrich, A., Bell, J.R., Chen, E.Y., Herrera, R., Petruzzelli, L.M., Dull, T.J., Gray, A., Coussens, L., Liao, Y.-C., Tsubokawa, Mason, A., Seeburg, P.H., Grunfeld, C., Rosen, O.M. & Ramachandran, J. (1985). Human insulin receptor and its relationship to the tyrosine kinase family of oncogenes, Nature, 313, 756-761.

Ullrich, A., Gray, A., Tam, A.W., Yang-Feng, T., Tsubokawa, M., Collins, C., Henzel W., Le Bon, T., Kathuria, S., Chen. E., Jacobs, S., Francke, U., Ramachandran, J. & Fujita-Yamaguchi, Y. (1986). Insulin-like growth factor 1 receptor primary structure: comparison with insulin receptor suggests structural determinants that define functional specificity. EMBO J, 5, 2503-2512.

van der Vorm, E.R., Kuipers, A., Kielkopfrenner, S., Krans, H.M.J., Moller, W. & Maassen, J.A. 1994. A mutation in the insulin receptor that impairs proreceptor processing but not insulin binding, *J. Biol. Chem.*, 269, 14297-14302.

Wada, A., Yokoo, H., Yanagita, T. & Kobayashi, H. (2005). New twist on neuronal insulin receptor signaling in health, disease, and therapeutics, J. Pharmacol Sci., 99, 128-143.

Wan Z., Xu, B., Huang, K., Chu, Y.C., Li, B., Nakagawa, S. H., Qu, Y., Hu, S. Q., Katsoyannis, P.G. & Weiss, M.A. (2004). Enhancing the activity of insulin at the receptor interface: crystal structure and photo-cross-linking of A8 analogues, Biochemistry, 2004; 43(51):16119-33.

Wan, Z. L., Huang, K., Xu, B., Hu, S.Q., Wang, S., Chu, Y.C, Katsoyannis, P.G. & Weiss, M.A. (2005). Diabetes-associated mutations in human insulin: crystal structure and photo-cross-linking studies of A-chain variant insulin Wakayama, Biochemistry, 44, 5000-5016.

Ward, C.W., Hoyne, P.A. & Flegg, R.H. (1995). Insulin and epidermal growth factor receptors contain the cysteine repeat motif found in the tumor necrosis factor receptor, Proteins: Struct. Funct. Genet., 22, 141-153.

Ward, C.W., (1999). Members of the insulin receptor family contain three fibronectin type III domains, Growth Factors, 16, 315-322.

Ward, C.W., & Garrett, T.P.J. (2001). The relationship between the L1 and L2 domains of the insulin and epidermal growth factor receptors and leucine-rich repeat modules, BMC Bioinformatics, 2:4 (http://www.biomedcentral.com/I471-2105/2/4).

Wedekind, F., Baer-Pontzen, K., Bala-Mohan, S., Choli, D., Zahn, H. & Brandenburg, D. (1989). Hormone binding site of the insulin receptor: analysis using photoaffinity-mediated avidin complexing, Biol. Chem. Hoppe Seyler, 370, 251-258.

Weiner. S.J., Kollman, P.A. Case, D.A. Singh, U.C. Ghio, C., Alagona, G. & Weiner. P. (1984). J. Am. Chem. Soc, 106, 765-784.

Whittaker, J., Garcia. P., Yu, G.Q. & Mynarcik. D.C. (1994). Transmembrane domain interactions are necessary for negative cooperativity of the insulin receptor, Mol. Endocrinol, 8, 1521-1527.

Whittaker, J., Groth, A.V., Mynarcik, D.C., Pluzek, L., Gadsboll, V.L. & Whittaker, L.J. (2001). Alanine scanning mutagenesis of a type 1 insulin-like growth factor receptor ligand binding site. J. Biol. Chem., 276, 43980-43986.

Whittaker, J., Sorensen, H., Gadsboll, V. & Hinrichsen, J. (2002). Comparison of the functional insulin binding epitopes of the A and B isoforms of the insulin receptor, J. Biol. Chem., 277, 47380-47384.

Williams. P.F., Mynarcik, D.C., Yu, G.Q. & Whittaker. J. (1995). Mapping of an NH2- terminal ligand binding site of the insulin receptor by alanine scanning mutagenesis, J. Biol. Chem., 270, 3012-3016.

Wood & Wetzel (1992). Int. J. Peptide Protein Res., 39, 533-39.

Xu, B., Hua, Q., Nakagawa, S.H., Jia, W., Chu, Y.-C., Katsoyannis, P.G. & Weiss, M.A. (2002). Chiral Mutagenesis of insulin's hidden receptor-binding surface: Structure of an allo-isolcucineA2 analogue, J. Mol. Biol., 316, 435-441.

Xu, B., Hu, S.Q., Chu, Y.C., Huang, K., Nakagawa, S.H., Whittaker, J., Katsoyannis, P.G. & Weiss, M.A. (2004). Diabetes-associated mutations in insulin; consecutive residues in the B chain contact distinct domains of the insulin receptor, Biochemistry, 43(26), 8356-72.

Yip, C.C., Hsu, H., Patel, R.G., Hawley, D.M., Maddux, B.A. & Goldfine, I.D. (1988). Localization of the insulin-binding site to the cysteine-rich region of the insulin receptor alpha-subunit, Biochem. Biophys. Res. Commun., 157, 321-329.

Yip, C.C. & Ottensmeyer, P. (2003). Three-dimensional structural interactions of insulin and its receptor, J. Biol. Chem., 278, 27329-27332.

Zhang, W., Gustafson, T.A., Rutter, WJ, & Johnson, J.D. (1994). Positively charged side chains in the insulin-like growth factor-1 C- and D-regions determine receptor binding specificity, J. Biol. Chem., 269, 10609-10613.

Zuckermann, et al. (1994). J. Med. Chem., 37, 2678.

Ward et al., "The Structure of the Type 1 Insulin-Like Growth Factor Receptor", *Insulin-Like Growth Factors, Medical Intelligence Unit*, LeRoith et al. (Eds.), Eurekah.com and Kluwer Academic / Plenum Publishers, pp. 1-21 (2003).

Lou et al., "The first three domains of the insulin receptor differ structurally from the insulin-like growth factor 1 receptor in the regions governing ligand specificity", *PNAS*, 103(33) pp. 12429-12434 (2006).

Garrett, et al., "Crystal structure of the first three domains of the type-1 insulin-like growth factor receptor", *Nature*, 394, pp. 395-399 (1998).

McKern et al., "Structure of the insulin receptor ectodomain reveals a folded-over conformation", *Nature*, 443, pp. 218-221 (2006).

* cited by examiner

83-7 kappa light chain

```
  M  D  S  Q  A  Q  V  L  M  L  L  L  W  I  S  G  T  C  G  D  I  V  M  S  Q  S  P  S  S   10
ATGGATTCACAGGCCCAGGTTCTTATGTTACTGCTGCTATGGATATCTGGTACCTGTGGGGACATTGTGATGTCACAGTCTCCATCCTCC
                                                      <-------------- CDR 1 ------------------>
  L  V  V  S  V  G  E  K  V  T  M  S  C  K  S  S  Q  S  L  L  Y  S  S  N  Q  K  N  F  L  A   40
CTAGTTGTGTCAGTTGGAGAGAAGGTTACTATGAGCTGTAAGTCCAGTCAGAGCCTTTTATATAGTAGCAATCAGAAGAACTTCTTGGCC
                                       <-- CDR 2 -->
  W  Y  Q  Q  K  P  G  Q  S  P  K  L  L  I  Y  W  A  S  T  R  E  S  G  V  P  D  R  F  T  G   70
TGGTACCAGCAGAAACCAGGGCAGTCTCCTAAACTGCTGATTTACTGGGCATCCACTAGGGAATCTGGGGTCCCTGATCGCTTCACAGGC
                                                                          <------- CDR 3 --
  S  G  S  G  T  D  F  T  L  T  I  S  S  V  K  A  E  D  L  A  V  Y  Y  C  Q  Q  Y  F  R  Y  100
AGTGGATCTGGGACAGATTTCACTCTCACCATCAGCAGTGTGAAGGCTGAAGACCTGGCAGTTTATTACTGTCAGCAATATTTTAGGTAT
------->
  R  T  E  G  G  G  T  K  L  E  I  K  R  A  D  A  A  P  T  V  S  I  F  P  P  S  S  E  Q  L  130
CGGACGTTCGAGGGAGGCACCAAGCTGGAAATCAAACGGGCTGATGCTGCACCAACTGTATCC

T  S  G  G  A  S  V  V  C  F  L  N  N  F  Y  P  K  D  I  N  V  K  W  K  I  D  G  S  E  R  160

Q  N  G  V  L  N  S  W  T  D  Q  D  S  K  D  S  T  Y  S  M  S  S  T  L  T  L  T  K  D  E  190

Y  E  R  H  N  S  Y  T  C  E  A  T  H  K  T  S  T  S  P  I  V  K  S  F  N  R  G  E  C      219
```

83-7 IgG1 heavy chain

```
  M  A  V  L  A  L  L  F  C  L  A  T  F  P  S  C  I  L  S  Q  V  Q  L  K  E  S  G  P  G  L   11
ATGGCTGTCCTGGCATTACTCTTCTGCCTGGCAACATTCCCCAGCTGTATCCTTTCCCAGGTGCAGCTGAAGGAGTCAGGACCTGGCCTG
                                                 <----- CDR 1 ------>
  V  A  P  S  Q  S  L  S  I  T  C  T  V  S  G  F  P  L  T  A  Y  G  V  N  W  V  R  Q  P  P   41
GTGGCGCCCTCACAGAGCCTGTCCATCACATGCACCGTCTCAGGGTTCCCATTAACCGCCTATGGTGTTAACTGGGTTCGCCAGCCTCCA
                                          <-- CDR 2 -->
  G  K  G  L  E  W  L  G  M  I  W  G  D  G  N  T  D  Y  N  S  A  L  K  S  R  L  S  I  S  K   71
GGAAAGGGTCTGGAGTGGCTGGGAATGATATGGGGTGATGGAAACACAGACTATAATTCAGCTCTCAAATCCAGACTGAGCATCAGCAAG
                                                                        <--------- CDR 3 ---
  D  N  S  K  S  Q  V  F  L  K  M  N  S  L  Q  T  D  D  T  A  R  Y  Y  C  A  R  D  P  Y  G  101
GACAACTCCAAGAGCCAAGTTTTCTTAAAAATGAACAGTCTGCAAACTGATGACACAGCCAGGTACTACTGTGCCAGAGACCCCTACGGT
---------------->
  S  K  P  M  D  Y  W  G  Q  G  T  S  V  T  V  S  S  A  K  T  T  P  P  S  V  Y  P  L  A  P  131
AGTAAGCCTATGGACTATTGGGGTCAAGGAACCTCGGTCACTGTCTCCTCAGCCAAAACGACACCCCCATCTGTCTATCCACTGGCCCCT

G  S  A  A  Q  T  N  S  M  V  T  L  G  C  L  V  K  G  Y  F  P  E  P  V  T  V  T  W  N  S  161
GGATCTGCTGCCCAAACTAAC

83-14 kappa light chain

```
        M  D  M  R  A  P  A  Q  I  F  G  F  L  L  L  L  F  P  G  T  R  C  D  I  Q  M  T  Q  S  P    8
        ATGGACATGAGGGCTCCTGCACAGATTTTTGGCTTCTTGTTGCTCTTGTTTCCAGGTACCAGATGTGACATCCAGATGACCCAGTCTCCA
                                                   <-------- CDR 1 -------->
        S  S  L  S  A  S  L  G  E  R  V  S  L  T  C  R  A  S  Q  D  I  G  G  N  L  Y  W  L  Q  Q   38
        TCCTCCTTATCTGCCTCTCTGGGAGAAAGAGTCAGTCTCACTTGTCGGGCAAGTCAGGACATTGGTGGTAACTTATACTGGCTTCAGCAG
                                      <-- CDR 2 -->
        G  P  D  G  T  I  K  R  L  I  Y  A  T  S  S  L  D  P  G  V  P  K  R  F  S  G  S  R  S  G   68
        GGACCAGATGGAACTATTAAACGCCTGATCTACGCCACATCCAGTTTAGATCCTGGTGTCCCCAAAAGGTTCAGTGGCAGTAGGTCTGGG
                                                                    <----- CDR 3 ----->
        S  D  Y  S  L  T  I  S  S  L  K  S  E  D  F  V  D  Y  Y  C  L  Q  Y  S  S  S  P  W  T  F   98
        TCAGATTATTCTCTCACCATCAGCAGCCTTAAGTCTGAAGATTTTGTAGACTATTACTGTCTACAGTATTCTAGTTCTCCGTGGACGTTC

G  G  G  T  K  L  E  E  I  K  R  A  D  A  A  P  T  V  S  A  A  P  T  V  S  I  F  P  P  S  128
        GGTGGAGGCACCAAGCTGGAAATCAAACGGGCTGATGCTGCACCAACTGTATCCAAG

S  E  Q  L  T  S  G  G  A  S  V  V  C  F  L  N  N  F  Y  P  K  D  I  N  V  K  W  K  I  D  158

G  S  E  R  Q  N  G  V  L  N  S  W  T  D  Q  D  S  K  D  S  T  Y  S  M  S  S  T  L  T  L  188

T  K  D  E  Y  E  R  H  N  S  Y  T  C  E  A  T  H  K  T  S  T  S  P  I  V  K  S  F  N  R  218

G  E  C                                                                                    221
```

83-14 IgG2a heavy chain

```
        M  G  W  R  W  I  F  L  F  L  L  S  G  T  A  G  V  H  C  Q  V  Q  L  Q  Q  S  G  P  E  L   11
        ATGGGATGGAGATGGATCTTTCTTTTCCTCCTGTCAGGAACTGCAGGTGTCCATTGCCAGGTTCAGCTGCAGCAGTCTGGACCTGAGCTG
                                                 <---- CDR 1 --->
        V  K  P  G  A  L  V  K  I  S  C  K  A  S  G  Y  T  F  T  N  Y  D  I  H  W  V  K  Q  R  P   41
        GTGAAGCCTGGGGCTTTAGTGAAGATATCCTGCAAGGCTTCTGGTTACACCTTCACAAACTACGATATACACTGGGTGAAGCAGAGGCCT
                                             <---- CDR 2 --->
        G  Q  G  L  E  W  I  G  W  I  Y  P  G  D  G  S  T  K  Y  N  E  K  F  K  G  K  A  T  L  T   71
        GGACAGGGACTTGAGTGGATTGGATGGATTTATCCTGGAGATGGTAGTACTAAGTACAATGAGAAATTCAAGGGCAAGGCCACACTGACT
                                                                           <-------- CDR 3 --
        A  D  K  S  S  S  T  A  Y  M  H  L  S  S  L  T  S  E  K  S  A  V  Y  F  C  A  R  E  W  A  101
        GCAGACAAATCCTCCAGCACAGCCTACATGCACCTCAGCAGCCTGACTTCTGAGAAATCTGCAGTCTATTTCTGTGCAAGAGAGTGGGCT
        ------------>
        Y  W  G  Q  G  T  L  V  T  V  S  A  A  K  T  T  A  P  S  V  Y  P  L  A  P  G  C  G  D  T  131
        TACTGGGGCCAAGGGACTCTGGTCACTGTCTCTGCAGCCAAAACAACAGCCCCATCGGTCTATCCACTGGCCCCTGGG

SEQUENCE LISTING

<160> NUMBER OF SEQ ID NOS: 15

<210> SEQ ID NO 1
<211> LENGTH: 1355
<212> TYPE: PRT

-continued

<213> ORGANISM: Homo sapiens

<400> SEQUENCE: 1

```
His Leu Tyr Pro Gly Glu Val Cys Pro Gly Met Asp Ile Arg Asn Asn
1               5                   10                  15

Leu Thr Arg Leu His Glu Leu Glu Asn Cys Ser Val Ile Glu Gly His
            20                  25                  30

Leu Gln Ile Leu Leu Met Phe Lys Thr Arg Pro Glu Asp Phe Arg Asp
        35                  40                  45

Leu Ser Phe Pro Lys Leu Ile Met Ile Thr Asp Tyr Leu Leu Leu Phe
    50                  55                  60

Arg Val Tyr Gly Leu Glu Ser Leu Lys Asp Leu Phe Pro Asn Leu Thr
65                  70                  75                  80

Val Ile Arg Gly Ser Arg Leu Phe Phe Asn Tyr Ala Leu Val Ile Phe
                85                  90                  95

Glu Met Val His Leu Lys Glu Leu Gly Leu Tyr Asn Leu Met Asn Ile
            100                 105                 110

Thr Arg Gly Ser Val Arg Ile Glu Lys Asn Asn Glu Leu Cys Tyr Leu
        115                 120                 125

Ala Thr Ile Asp Trp Ser Arg Ile Leu Asp Ser Val Glu Asp Asn His
    130                 135                 140

Ile Val Leu Asn Lys Asp Asp Asn Glu Glu Cys Gly Asp Ile Cys Pro
145                 150                 155                 160

Gly Thr Ala Lys Gly Lys Thr Asn Cys Pro Ala Thr Val Ile Asn Gly
                165                 170                 175

Gln Phe Val Glu Arg Cys Trp Thr His Ser His Cys Gln Lys Val Cys
            180                 185                 190

Pro Thr Ile Cys Lys Ser His Gly Cys Thr Ala Glu Gly Leu Cys Cys
        195                 200                 205

His Ser Glu Cys Leu Gly Asn Cys Ser Gln Pro Asp Asp Pro Thr Lys
    210                 215                 220

Cys Val Ala Cys Arg Asn Phe Tyr Leu Asp Gly Arg Cys Val Glu Thr
225                 230                 235                 240

Cys Pro Pro Pro Tyr Tyr His Phe Gln Asp Trp Arg Cys Val Asn Phe
                245                 250                 255

Ser Phe Cys Gln Asp Leu His His Lys Cys Lys Asn Ser Arg Arg Gln
            260                 265                 270

Gly Cys His Gln Tyr Val Ile His Asn Asn Lys Cys Ile Pro Glu Cys
        275                 280                 285

Pro Ser Gly Tyr Thr Met Asn Ser Ser Asn Leu Leu Cys Thr Pro Cys
    290                 295                 300

Leu Gly Pro Cys Pro Lys Val Cys His Leu Leu Glu Gly Glu Lys Thr
305                 310                 315                 320

Ile Asp Ser Val Thr Ser Ala Gln Glu Leu Arg Gly Cys Thr Val Ile
                325                 330                 335

Asn Gly Ser Leu Ile Ile Asn Ile Arg Gly Gly Asn Asn Leu Ala Ala
            340                 345                 350

Glu Leu Glu Ala Asn Leu Gly Leu Ile Glu Glu Ile Ser Gly Tyr Leu
        355                 360                 365

Lys Ile Arg Arg Ser Tyr Ala Leu Val Ser Leu Ser Phe Phe Arg Lys
    370                 375                 380

Leu Arg Leu Ile Arg Gly Glu Thr Leu Glu Ile Gly Asn Tyr Ser Phe
385                 390                 395                 400
```

```
Tyr Ala Leu Asp Asn Gln Asn Leu Arg Gln Leu Trp Asp Trp Ser Lys
                405                 410                 415

His Asn Leu Thr Thr Thr Gln Gly Lys Leu Phe Phe His Tyr Asn Pro
            420                 425                 430

Lys Leu Cys Leu Ser Glu Ile His Lys Met Glu Glu Val Ser Gly Thr
        435                 440                 445

Lys Gly Arg Gln Glu Arg Asn Asp Ile Ala Leu Lys Thr Asn Gly Asp
    450                 455                 460

Lys Ala Ser Cys Glu Asn Glu Leu Leu Lys Phe Ser Tyr Ile Arg Thr
465                 470                 475                 480

Ser Phe Asp Lys Ile Leu Leu Arg Trp Glu Pro Tyr Trp Pro Pro Asp
                485                 490                 495

Phe Arg Asp Leu Leu Gly Phe Met Leu Phe Tyr Lys Glu Ala Pro Tyr
            500                 505                 510

Gln Asn Val Thr Glu Phe Asp Gly Gln Asp Ala Cys Gly Ser Asn Ser
        515                 520                 525

Trp Thr Val Val Asp Ile Asp Pro Pro Leu Arg Ser Asn Asp Pro Lys
    530                 535                 540

Ser Gln Asn His Pro Gly Trp Leu Met Arg Gly Leu Lys Pro Trp Thr
545                 550                 555                 560

Gln Tyr Ala Ile Phe Val Lys Thr Leu Val Thr Phe Ser Asp Glu Arg
                565                 570                 575

Arg Thr Tyr Gly Ala Lys Ser Asp Ile Ile Tyr Val Gln Thr Asp Ala
            580                 585                 590

Thr Asn Pro Ser Val Pro Leu Asp Pro Ile Ser Val Ser Asn Ser Ser
        595                 600                 605

Ser Gln Ile Ile Leu Lys Trp Lys Pro Pro Ser Asp Pro Asn Gly Asn
    610                 615                 620

Ile Thr His Tyr Leu Val Phe Trp Glu Arg Gln Ala Glu Asp Ser Glu
625                 630                 635                 640

Leu Phe Glu Leu Asp Tyr Cys Leu Lys Gly Leu Lys Leu Pro Ser Arg
                645                 650                 655

Thr Trp Ser Pro Pro Phe Glu Ser Glu Asp Ser Gln Lys His Asn Gln
            660                 665                 670

Ser Glu Tyr Glu Asp Ser Ala Gly Glu Cys Cys Ser Cys Pro Lys Thr
        675                 680                 685

Asp Ser Gln Ile Leu Lys Glu Leu Glu Glu Ser Ser Phe Arg Lys Thr
    690                 695                 700

Phe Glu Asp Tyr Leu His Asn Val Val Phe Val Pro Arg Lys Thr Ser
705                 710                 715                 720

Ser Gly Thr Gly Ala Glu Asp Pro Arg Pro Ser Arg Lys Arg Arg Ser
                725                 730                 735

Leu Gly Asp Val Gly Asn Val Thr Val Ala Val Pro Thr Val Ala Ala
            740                 745                 750

Phe Pro Asn Thr Ser Ser Thr Ser Val Pro Thr Ser Pro Glu Glu His
        755                 760                 765

Arg Pro Phe Glu Lys Val Val Asn Lys Glu Ser Leu Val Ile Ser Gly
    770                 775                 780

Leu Arg His Phe Thr Gly Tyr Arg Ile Glu Leu Gln Ala Cys Asn Gln
785                 790                 795                 800

Asp Thr Pro Glu Glu Arg Cys Ser Val Ala Ala Tyr Val Ser Ala Arg
                805                 810                 815

Thr Met Pro Glu Ala Lys Ala Asp Asp Ile Val Gly Pro Val Thr His
            820                 825                 830
```

-continued

```
Glu Ile Phe Glu Asn Asn Val Val His Leu Met Trp Gln Glu Pro Lys
    835                 840                 845

Glu Pro Asn Gly Leu Ile Val Leu Tyr Glu Val Ser Tyr Arg Arg Tyr
850                 855                 860

Gly Asp Glu Glu Leu His Leu Cys Val Ser Arg Lys His Phe Ala Leu
865                 870                 875                 880

Glu Arg Gly Cys Arg Leu Arg Gly Leu Ser Pro Gly Asn Tyr Ser Val
                885                 890                 895

Arg Ile Arg Ala Thr Ser Leu Ala Gly Asn Gly Ser Trp Thr Glu Pro
            900                 905                 910

Thr Tyr Phe Tyr Val Thr Asp Tyr Leu Asp Val Pro Ser Asn Ile Ala
        915                 920                 925

Lys Ile Ile Ile Gly Pro Leu Ile Phe Val Phe Leu Phe Ser Val Val
    930                 935                 940

Ile Gly Ser Ile Tyr Leu Phe Leu Arg Lys Arg Gln Pro Asp Gly Pro
945                 950                 955                 960

Leu Gly Pro Leu Tyr Ala Ser Ser Asn Pro Glu Tyr Leu Ser Ala Ser
                965                 970                 975

Asp Val Phe Pro Cys Ser Val Tyr Val Pro Asp Glu Trp Glu Val Ser
            980                 985                 990

Arg Glu Lys Ile Thr Leu Leu Arg Glu Leu Gly Gln Gly Ser Phe Gly
        995                 1000                1005

Met Val Tyr Glu Gly Asn Ala Arg Asp Ile Ile Lys Gly Glu Ala
    1010                1015                1020

Glu Thr Arg Val Ala Val Lys Thr Val Asn Glu Ser Ala Ser Leu
    1025                1030                1035

Arg Glu Arg Ile Glu Phe Leu Asn Glu Ala Ser Val Met Lys Gly
    1040                1045                1050

Phe Thr Cys His His Val Val Arg Leu Leu Gly Val Val Ser Lys
    1055                1060                1065

Gly Gln Pro Thr Leu Val Val Met Glu Leu Met Ala His Gly Asp
    1070                1075                1080

Leu Lys Ser Tyr Leu Arg Ser Leu Arg Pro Glu Ala Glu Asn Asn
    1085                1090                1095

Pro Gly Arg Pro Pro Thr Leu Gln Glu Met Ile Gln Met Ala
    1100                1105                1110

Ala Glu Ile Ala Asp Gly Met Ala Tyr Leu Asn Ala Lys Lys Phe
    1115                1120                1125

Val His Arg Asp Leu Ala Ala Arg Asn Cys Met Val Ala His Asp
    1130                1135                1140

Phe Thr Val Lys Ile Gly Asp Phe Gly Met Thr Arg Asp Ile Tyr
    1145                1150                1155

Glu Thr Asp Tyr Tyr Arg Lys Gly Gly Lys Gly Leu Leu Pro Val
    1160                1165                1170

Arg Trp Met Ala Pro Glu Ser Leu Lys Asp Gly Val Phe Thr Thr
    1175                1180                1185

Ser Ser Asp Met Trp Ser Phe Gly Val Val Leu Trp Glu Ile Thr
    1190                1195                1200

Ser Leu Ala Glu Gln Pro Tyr Gln Gly Leu Ser Asn Glu Gln Val
    1205                1210                1215

Leu Lys Phe Val Met Asp Gly Gly Tyr Leu Asp Gln Pro Asp Asn
    1220                1225                1230

Cys Pro Glu Arg Val Thr Asp Leu Met Arg Met Cys Trp Gln Phe
    1235                1240                1245
```

```
Asn Pro Lys Met Arg Pro Thr Phe Leu Glu Ile Val Asn Leu Leu
    1250                1255                1260

Lys Asp Asp Leu His Pro Ser Phe Pro Glu Val Ser Phe Phe His
    1265                1270                1275

Ser Glu Glu Asn Lys Ala Pro Glu Ser Glu Leu Glu Met Glu
    1280                1285                1290

Phe Glu Asp Met Glu Asn Val Pro Leu Asp Arg Ser Ser His Cys
    1295                1300                1305

Gln Arg Glu Glu Ala Gly Gly Arg Asp Gly Gly Ser Ser Leu Gly
    1310                1315                1320

Phe Lys Arg Ser Tyr Glu Glu His Ile Pro Tyr Thr His Met Asn
    1325                1330                1335

Gly Gly Lys Lys Asn Gly Arg Ile Leu Thr Leu Pro Arg Ser Asn
    1340                1345                1350

Pro Ser
    1355

<210> SEQ ID NO 2
<211> LENGTH: 917
<212> TYPE: PRT
<213> ORGANISM: Homo Sapiens

<400> SEQUENCE: 2

His Leu Tyr Pro Gly Glu Val Cys Pro Gly Met Asp Ile Arg Asn Asn
1               5                   10                  15

Leu Thr Arg Leu His Glu Leu Glu Asn Cys Ser Val Ile Glu Gly His
            20                  25                  30

Leu Gln Ile Leu Leu Met Phe Lys Thr Arg Pro Glu Asp Phe Arg Asp
        35                  40                  45

Leu Ser Phe Pro Lys Leu Ile Met Ile Thr Asp Tyr Leu Leu Leu Phe
    50                  55                  60

Arg Val Tyr Gly Leu Glu Ser Leu Lys Asp Leu Phe Pro Asn Leu Thr
65                  70                  75                  80

Val Ile Arg Gly Ser Arg Leu Phe Phe Asn Tyr Ala Leu Val Ile Phe
                85                  90                  95

Glu Met Val His Leu Lys Glu Leu Gly Leu Tyr Asn Leu Met Asn Ile
            100                 105                 110

Thr Arg Gly Ser Val Arg Ile Glu Lys Asn Asn Glu Leu Cys Tyr Leu
        115                 120                 125

Ala Thr Ile Asp Trp Ser Arg Ile Leu Asp Ser Val Glu Asp Asn His
    130                 135                 140

Ile Val Leu Asn Lys Asp Asp Asn Glu Glu Cys Gly Asp Ile Cys Pro
145                 150                 155                 160

Gly Thr Ala Lys Gly Lys Thr Asn Cys Pro Ala Thr Val Ile Asn Gly
                165                 170                 175

Gln Phe Val Glu Arg Cys Trp Thr His Ser His Cys Gln Lys Val Cys
            180                 185                 190

Pro Thr Ile Cys Lys Ser His Gly Cys Thr Ala Glu Gly Leu Cys Cys
        195                 200                 205

His Ser Glu Cys Leu Gly Asn Cys Ser Gln Pro Asp Asp Pro Thr Lys
    210                 215                 220

Cys Val Ala Cys Arg Asn Phe Tyr Leu Asp Gly Arg Cys Val Glu Thr
225                 230                 235                 240

Cys Pro Pro Pro Tyr Tyr His Phe Gln Asp Trp Arg Cys Val Asn Phe
                245                 250                 255
```

```
Ser Phe Cys Gln Asp Leu His His Lys Cys Lys Asn Ser Arg Arg Gln
        260                 265                 270

Gly Cys His Gln Tyr Val Ile His Asn Asn Lys Cys Ile Pro Glu Cys
        275                 280                 285

Pro Ser Gly Tyr Thr Met Asn Ser Ser Asn Leu Leu Cys Thr Pro Cys
        290                 295                 300

Leu Gly Pro Cys Pro Lys Val Cys His Leu Leu Glu Gly Glu Lys Thr
305                 310                 315                 320

Ile Asp Ser Val Thr Ser Ala Gln Glu Leu Arg Gly Cys Thr Val Ile
                325                 330                 335

Asn Gly Ser Leu Ile Ile Asn Ile Arg Gly Gly Asn Asn Leu Ala Ala
                340                 345                 350

Glu Leu Glu Ala Asn Leu Gly Leu Ile Glu Glu Ile Ser Gly Tyr Leu
            355                 360                 365

Lys Ile Arg Arg Ser Tyr Ala Leu Val Ser Leu Ser Phe Phe Arg Lys
        370                 375                 380

Leu Arg Leu Ile Arg Gly Glu Thr Leu Glu Ile Gly Asn Tyr Ser Phe
385                 390                 395                 400

Tyr Ala Leu Asp Asn Gln Asn Leu Arg Gln Leu Trp Asp Trp Ser Lys
                405                 410                 415

His Asn Leu Thr Thr Thr Gln Gly Lys Leu Phe Phe His Tyr Asn Pro
                420                 425                 430

Lys Leu Cys Leu Ser Glu Ile His Lys Met Glu Glu Val Ser Gly Thr
            435                 440                 445

Lys Gly Arg Gln Glu Arg Asn Asp Ile Ala Leu Lys Thr Asn Gly Asp
        450                 455                 460

Lys Ala Ser Cys Glu Asn Glu Leu Leu Lys Phe Ser Tyr Ile Arg Thr
465                 470                 475                 480

Ser Phe Asp Lys Ile Leu Leu Arg Trp Glu Pro Tyr Trp Pro Pro Asp
                485                 490                 495

Phe Arg Asp Leu Leu Gly Phe Met Leu Phe Tyr Lys Glu Ala Pro Tyr
                500                 505                 510

Gln Asn Val Thr Glu Phe Asp Gly Gln Asp Ala Cys Gly Ser Asn Ser
            515                 520                 525

Trp Thr Val Val Asp Ile Asp Pro Pro Leu Arg Ser Asn Asp Pro Lys
        530                 535                 540

Ser Gln Asn His Pro Gly Trp Leu Met Arg Gly Leu Lys Pro Trp Thr
545                 550                 555                 560

Gln Tyr Ala Ile Phe Val Lys Thr Leu Val Thr Phe Ser Asp Glu Arg
                565                 570                 575

Arg Thr Tyr Gly Ala Lys Ser Asp Ile Ile Tyr Val Gln Thr Asp Ala
                580                 585                 590

Thr Asn Pro Ser Val Pro Leu Asp Pro Ile Ser Val Ser Asn Ser Ser
            595                 600                 605

Ser Gln Ile Ile Leu Lys Trp Lys Pro Pro Ser Asp Pro Asn Gly Asn
        610                 615                 620

Ile Thr His Tyr Leu Val Phe Trp Glu Arg Gln Ala Glu Asp Ser Glu
625                 630                 635                 640

Leu Phe Glu Leu Asp Tyr Cys Leu Lys Gly Leu Lys Leu Pro Ser Arg
                645                 650                 655

Thr Trp Ser Pro Pro Phe Glu Ser Glu Asp Ser Gln Lys His Asn Gln
                660                 665                 670

Ser Glu Tyr Glu Asp Ser Ala Gly Glu Cys Cys Ser Cys Pro Lys Thr
            675                 680                 685
```

```
Asp Ser Gln Ile Leu Lys Glu Leu Glu Glu Ser Ser Phe Arg Lys Thr
        690                 695                 700

Phe Glu Asp Tyr Leu His Asn Val Val Phe Pro Arg Pro Ser Arg
705                 710                 715                 720

Lys Arg Arg Ser Leu Gly Asp Val Gly Asn Val Thr Val Ala Val Pro
                725                 730                 735

Thr Val Ala Ala Phe Pro Asn Thr Ser Ser Thr Ser Val Pro Thr Ser
            740                 745                 750

Pro Glu Glu His Arg Pro Phe Glu Lys Val Val Asn Lys Glu Ser Leu
        755                 760                 765

Val Ile Ser Gly Leu Arg His Phe Thr Gly Tyr Arg Ile Glu Leu Gln
770                 775                 780

Ala Cys Asn Gln Asp Thr Pro Glu Glu Arg Cys Ser Val Ala Ala Tyr
785                 790                 795                 800

Val Ser Ala Arg Thr Met Pro Glu Ala Lys Ala Asp Asp Ile Val Gly
                805                 810                 815

Pro Val Thr His Glu Ile Phe Glu Asn Asn Val Val His Leu Met Trp
            820                 825                 830

Gln Glu Pro Lys Glu Pro Asn Gly Leu Ile Val Leu Tyr Glu Val Ser
        835                 840                 845

Tyr Arg Arg Tyr Gly Asp Glu Glu Leu His Leu Cys Val Ser Arg Lys
850                 855                 860

His Phe Ala Leu Glu Arg Gly Cys Arg Leu Arg Gly Leu Ser Pro Gly
865                 870                 875                 880

Asn Tyr Ser Val Arg Ile Arg Ala Thr Ser Leu Ala Gly Asn Gly Ser
                885                 890                 895

Trp Thr Glu Pro Thr Tyr Phe Tyr Val Thr Asp Tyr Leu Asp Val Pro
            900                 905                 910

Ser Asn Ile Ala Lys
        915

<210> SEQ ID NO 3
<211> LENGTH: 905
<212> TYPE: PRT
<213> ORGANISM: Homo Sapiens

<400> SEQUENCE: 3

Glu Ile Cys Gly Pro Gly Ile Asp Ile Arg Asn Asp Tyr Gln Gln Leu
1               5                   10                  15

Lys Arg Leu Glu Asn Cys Thr Val Ile Glu Gly Tyr Leu His Ile Leu
                20                  25                  30

Leu Ile Ser Lys Ala Glu Asp Tyr Arg Ser Tyr Arg Phe Pro Lys Leu
            35                  40                  45

Thr Val Ile Thr Glu Tyr Leu Leu Leu Phe Arg Val Ala Gly Leu Glu
        50                  55                  60

Ser Leu Gly Asp Leu Phe Pro Asn Leu Thr Val Ile Arg Gly Trp Lys
65                  70                  75                  80

Leu Phe Tyr Asn Tyr Ala Leu Val Ile Phe Glu Met Thr Asn Leu Lys
                85                  90                  95

Asp Ile Gly Leu Tyr Asn Leu Arg Asn Ile Thr Arg Gly Ala Ile Arg
            100                 105                 110

Ile Glu Lys Asn Ala Asp Leu Cys Tyr Leu Ser Thr Val Asp Trp Ser
        115                 120                 125

Leu Ile Leu Asp Ala Val Ser Asn Asn Tyr Ile Val Gly Asn Lys Pro
    130                 135                 140
```

```
Pro Lys Glu Cys Gly Asp Leu Cys Pro Gly Thr Met Glu Lys Pro
145                 150                 155                 160

Met Cys Glu Lys Thr Thr Ile Asn Asn Glu Tyr Asn Tyr Arg Cys Trp
                165                 170                 175

Thr Thr Asn Arg Cys Gln Lys Met Cys Pro Ser Thr Cys Gly Lys Arg
            180                 185                 190

Ala Cys Thr Glu Asn Asn Glu Cys Cys His Pro Glu Cys Leu Gly Ser
        195                 200                 205

Cys Ser Ala Pro Asp Asn Asp Thr Ala Cys Val Ala Cys Arg His Tyr
    210                 215                 220

Tyr Tyr Ala Gly Val Cys Val Pro Ala Cys Pro Pro Asn Thr Tyr Arg
225                 230                 235                 240

Phe Glu Gly Trp Arg Cys Val Asp Arg Asp Phe Cys Ala Asn Ile Leu
                245                 250                 255

Ser Ala Glu Ser Ser Asp Ser Glu Gly Phe Val Ile His Asp Gly Glu
            260                 265                 270

Cys Met Gln Glu Cys Pro Ser Gly Phe Ile Arg Asn Gly Ser Gln Ser
        275                 280                 285

Met Tyr Cys Ile Pro Cys Glu Gly Pro Cys Pro Lys Val Cys Glu Glu
    290                 295                 300

Glu Lys Lys Thr Lys Thr Ile Asp Ser Val Thr Ser Ala Gln Met Leu
305                 310                 315                 320

Gln Gly Cys Thr Ile Phe Lys Gly Asn Leu Leu Ile Asn Ile Arg Arg
                325                 330                 335

Gly Asn Asn Ile Ala Ser Glu Leu Glu Asn Phe Met Gly Leu Ile Glu
            340                 345                 350

Val Val Thr Gly Tyr Val Lys Ile Arg His Ser His Ala Leu Val Ser
        355                 360                 365

Leu Ser Phe Leu Lys Asn Leu Arg Leu Ile Leu Gly Glu Glu Gln Leu
    370                 375                 380

Glu Gly Asn Tyr Ser Phe Tyr Val Leu Asp Asn Gln Asn Leu Gln Gln
385                 390                 395                 400

Leu Trp Asp Trp Asp His Arg Asn Leu Thr Ile Lys Ala Gly Lys Met
                405                 410                 415

Tyr Phe Ala Phe Asn Pro Lys Leu Cys Val Ser Glu Ile Tyr Arg Met
            420                 425                 430

Glu Glu Val Thr Gly Thr Lys Gly Arg Gln Ser Lys Gly Asp Ile Asn
        435                 440                 445

Thr Arg Asn Asn Gly Glu Arg Ala Ser Cys Glu Ser Asp Val Leu His
    450                 455                 460

Phe Thr Ser Thr Thr Thr Ser Lys Asn Arg Ile Ile Ile Thr Trp His
465                 470                 475                 480

Arg Tyr Arg Pro Pro Asp Tyr Arg Asp Leu Ile Ser Phe Thr Val Tyr
                485                 490                 495

Tyr Lys Glu Ala Pro Phe Lys Asn Val Thr Glu Tyr Asp Gly Gln Asp
            500                 505                 510

Ala Cys Gly Ser Asn Ser Trp Asn Met Val Asp Val Asp Leu Pro Pro
        515                 520                 525

Asn Lys Asp Val Glu Pro Gly Ile Leu Leu His Gly Leu Lys Pro Trp
    530                 535                 540

Thr Gln Tyr Ala Val Tyr Val Lys Ala Val Thr Leu Thr Met Val Glu
545                 550                 555                 560

Asn Asp His Ile Arg Gly Ala Lys Ser Glu Ile Leu Tyr Ile Arg Thr
                565                 570                 575
```

-continued

```
Asn Ala Ser Val Pro Ser Ile Pro Leu Asp Val Leu Ser Ala Ser Asn
            580                 585                 590

Ser Ser Ser Gln Leu Ile Val Lys Trp Asn Pro Pro Ser Leu Pro Asn
        595                 600                 605

Gly Asn Leu Ser Tyr Tyr Ile Val Arg Trp Gln Arg Gln Pro Gln Asp
    610                 615                 620

Gly Tyr Leu Tyr Arg His Asn Tyr Cys Ser Lys Asp Lys Ile Pro Ile
625                 630                 635                 640

Arg Lys Tyr Ala Asp Gly Thr Ile Asp Ile Glu Glu Val Thr Glu Asn
                645                 650                 655

Pro Lys Thr Glu Val Cys Gly Gly Glu Lys Gly Pro Cys Cys Ala Cys
            660                 665                 670

Pro Lys Thr Glu Ala Glu Lys Gln Ala Glu Lys Glu Glu Ala Glu Tyr
        675                 680                 685

Arg Lys Val Phe Glu Asn Phe Leu His Asn Ser Ile Phe Val Pro Arg
    690                 695                 700

Pro Glu Arg Lys Arg Arg Asp Val Met Gln Val Ala Asn Thr Thr Met
705                 710                 715                 720

Ser Ser Arg Ser Arg Asn Thr Thr Ala Ala Asp Thr Tyr Asn Ile Thr
                725                 730                 735

Asp Pro Glu Glu Leu Glu Thr Glu Tyr Pro Phe Phe Glu Ser Arg Val
            740                 745                 750

Asp Asn Lys Glu Arg Thr Val Ile Ser Asn Leu Arg Pro Phe Thr Leu
        755                 760                 765

Tyr Arg Ile Asp Ile His Ser Cys Asn His Glu Ala Glu Lys Leu Gly
    770                 775                 780

Cys Ser Ala Ser Asn Phe Val Phe Ala Arg Thr Met Pro Ala Glu Gly
785                 790                 795                 800

Ala Asp Asp Ile Pro Gly Pro Val Thr Trp Glu Pro Arg Pro Glu Asn
                805                 810                 815

Ser Ile Phe Leu Lys Trp Pro Glu Pro Glu Asn Pro Asn Gly Leu Ile
            820                 825                 830

Leu Met Tyr Glu Ile Lys Tyr Gly Ser Gln Val Glu Asp Gln Arg Glu
        835                 840                 845

Cys Val Ser Arg Gln Glu Tyr Arg Lys Tyr Gly Gly Ala Lys Leu Asn
    850                 855                 860

Arg Leu Asn Pro Gly Asn Tyr Thr Ala Arg Ile Gln Ala Thr Ser Leu
865                 870                 875                 880

Ser Gly Asn Gly Ser Trp Thr Asp Pro Val Phe Phe Tyr Val Gln Ala
                885                 890                 895

Lys Thr Gly Tyr Glu Asn Phe Ile His
            900                 905

<210> SEQ ID NO 4
<211> LENGTH: 239
<212> TYPE: PRT
<213> ORGANISM: Artificial sequence
<220> FEATURE:
<223> OTHER INFORMATION: Synthetic construct: MAb 83-14 IgG2a heavy
      chain

<400> SEQUENCE: 4

Met Gly Trp Arg Trp Ile Phe Leu Phe Leu Leu Ser Gly Thr Ala Gly
1               5                   10                  15

Val His Cys Gln Val Gln Leu Gln Gln Ser Gly Pro Glu Leu Val Lys
            20                  25                  30
```

Pro Gly Ala Leu Val Lys Ile Ser Cys Lys Ala Ser Gly Tyr Thr Phe
        35                  40                  45

Thr Asn Tyr Asp Ile His Trp Val Lys Gln Arg Pro Gly Gln Gly Leu
 50                  55                  60

Glu Trp Ile Gly Trp Ile Tyr Pro Gly Asp Gly Ser Thr Lys Tyr Asn
 65                  70                  75                  80

Glu Lys Phe Lys Gly Lys Ala Thr Leu Thr Ala Asp Lys Ser Ser Ser
                 85                  90                  95

Thr Ala Tyr Met His Leu Ser Ser Leu Thr Ser Glu Lys Ser Ala Val
            100                 105                 110

Tyr Phe Cys Ala Arg Glu Trp Ala Tyr Trp Gly Gln Gly Thr Leu Val
        115                 120                 125

Thr Val Ser Ala Ala Lys Thr Thr Ala Pro Ser Val Tyr Pro Leu Ala
130                 135                 140

Pro Gly Cys Gly Asp Thr Thr Gly Ser Ser Val Thr Leu Gly Cys Leu
145                 150                 155                 160

Val Lys Gly Tyr Phe Pro Glu Pro Val Thr Leu Thr Trp Asn Ser Gly
                165                 170                 175

Ser Leu Ser Ser Gly Val His Thr Phe Pro Ala Val Leu Gln Ser Asp
            180                 185                 190

Leu Tyr Thr Leu Ser Ser Ser Val Thr Val Thr Ser Ser Thr Trp Pro
        195                 200                 205

Ser Gln Ser Ile Thr Cys Asn Val Ala His Pro Ala Ser Ser Thr Lys
    210                 215                 220

Val Asp Lys Lys Ile Glu Pro Arg Gly Pro Thr Ile Lys Pro Cys
225                 230                 235

<210> SEQ ID NO 5
<211> LENGTH: 438
<212> TYPE: DNA
<213> ORGANISM: Artificial Sequence
<220> FEATURE:
<223> OTHER INFORMATION: Synthetic construct: MAb 83-14 IgG2a heavy
      chain

<400> SEQUENCE: 5
atgggatgga gatggatctt tcttttcctc ctgtcaggaa ctgcaggtgt ccattgccag      60
gttcagctgc agcagtctgg acctgagctg gtgaagcctg ggctttagt gaagatatcc     120 tgcaaggctt ctggttacac cttcacaaac tacgatatac actgggtgaa gcagaggcct     180
ggacagggac ttgagtggat tggatggatt tatcctggag atggtagtac taagtacaat     240
gagaaattca agggcaaggc cacactgact gcagacaaat cctccagcac agcctacatg     300
cacctcagca gcctgacttc tgagaaatct gcagtctatt tctgtgcaag agagtgggct     360
tactggggcc aagggactct ggtcactgtc tctgcagcca aaacaacagc cccatcggtc     420
tatccactgg cccctggg                                                    438

<210> SEQ ID NO 6
<211> LENGTH: 243
<212> TYPE: PRT
<213> ORGANISM: Artificial sequence
<220> FEATURE:
<223> OTHER INFORMATION: Synthetic construct: MAb 83-14 kappa light
      chain -continued

```
<400> SEQUENCE: 6

Met Asp Met Arg Ala Pro Ala Gln Ile Phe Gly Phe Leu Leu Leu
1               5                   10                  15

Phe Pro Gly Thr Arg Cys Asp Ile Gln Met Thr Gln Ser Pro Ser
            20                  25                  30

Leu Ser Ala Ser Leu Gly Glu Arg Val Ser Leu Thr Cys Arg Ala Ser
        35                  40                  45

Gln Asp Ile Gly Gly Asn Leu Tyr Trp Leu Gln Gln Gly Pro Asp Gly
    50                  55                  60

Thr Ile Lys Arg Leu Ile Tyr Ala Thr Ser Ser Leu Asp Pro Gly Val
65                  70                  75                  80

Pro Lys Arg Phe Ser Gly Ser Arg Ser Gly Ser Asp Tyr Ser Leu Thr
                85                  90                  95

Ile Ser Ser Leu Lys Ser Glu Asp Phe Val Asp Tyr Tyr Cys Leu Gln
                100                 105                 110

Tyr Ser Ser Ser Pro Trp Thr Phe Gly Gly Gly Thr Lys Leu Glu Glu
                115                 120                 125

Ile Lys Arg Ala Asp Ala Ala Pro Thr Val Ser Ala Ala Pro Thr Val
130                 135                 140

Ser Ile Phe Pro Pro Ser Ser Glu Gln Leu Thr Ser Gly Gly Ala Ser
145                 150                 155                 160

Val Val Cys Phe Leu Asn Asn Phe Tyr Pro Lys Asp Ile Asn Val Lys
                165                 170                 175

Trp Lys Ile Asp Gly Ser Glu Arg Gln Asn Gly Val Leu Asn Ser Trp
                180                 185                 190

Thr Asp Gln Asp Ser Lys Asp Ser Thr Tyr Ser Met Ser Ser Thr Leu
                195                 200                 205

Thr Leu Thr Lys Asp Glu Tyr Glu Arg His Asn Ser Tyr Thr Cys Glu
210                 215                 220

Ala Thr His Lys Thr Ser Thr Ser Pro Ile Val Lys Ser Phe Asn Arg
225                 230                 235                 240

Gly Glu Cys

<210> SEQ ID NO 7
<211> LENGTH: 417
<212> TYPE: DNA
<213> ORGANISM: Artificial Sequence
<220> FEATURE:
<223> OTHER INFORMATION: Synthetic construct: MAb 83-14 kappa light
      chain

<400> SEQUENCE: 7
atggacatga gggctcctgc acagattttt ggcttcttgt tgctcttgtt tccaggtacc      60
agatgtgaca tccagatgac ccagtctcca tcctccttat ctgcctctct gggagaaaga     120
gtcagtctca cttgtcgggc aagtcaggac attggtggta acttatactg gcttcagcag     180
ggaccagatg gaactattaa acgcctgatc tacgccacat ccagtttaga tcctggtgtc     240
cccaaaaggt tcagtggcag taggtctggg tcagattatt ctctcaccat cagcagcctt     300
aagtctgaag attttgtaga ctattactgt ctacagtatt ctagttctcc gtggacgttc     360
ggtggaggca ccaagctgga aatcaaacgg gctgatgctg caccaactgt atccaag       417

<210> SEQ ID NO 8
<211> LENGTH: 239
<212> TYPE: PRT
<213> ORGANISM: Artificial sequence
```

```
<220> FEATURE:
<223> OTHER INFORMATION: Synthetic construct: MAb 83-7 IgG1 heavy chain

<400> SEQUENCE: 8

Met Ala Val Leu Ala Leu Leu Phe Cys Leu Ala Thr Phe Pro Ser Cys
1               5                   10                  15

Ile Leu Ser Gln Val Gln Leu Lys Glu Ser Gly Pro Gly Leu Val Ala
            20                  25                  30

Pro Ser Gln Ser Leu Ser Ile Thr Cys Thr Val Ser Gly Phe Pro Leu
        35                  40                  45

Thr Ala Tyr Gly Val Asn Trp Val Arg Gln Pro Pro Lys Gly Leu
    50                  55                  60

Glu Trp Leu Gly Met Ile Trp Gly Asp Gly Asn Thr Asp Tyr Asn Ser
65                  70                  75                  80

Ala Leu Lys Ser Arg Leu Ser Ile Ser Lys Asp Asn Ser Lys Ser Gln
                85                  90                  95

Val Phe Leu Lys Met Asn Ser Leu Gln Thr Asp Asp Thr Ala Arg Tyr
            100                 105                 110

Tyr Cys Ala Arg Asp Pro Tyr Gly Ser Lys Pro Met Asp Tyr Trp Gly
        115                 120                 125

Gln Gly Thr Ser Val Thr Val Ser Ser Ala Lys Thr Thr Pro Pro Ser
130                 135                 140

Val Tyr Pro Leu Ala Pro Gly Ser Ala Ala Gln Thr Asn Ser Met Val
145                 150                 155                 160

Thr Leu Gly Cys Leu Val Lys Gly Tyr Phe Pro Glu Pro Val Thr Val
                165                 170                 175

Thr Trp Asn Ser Gly Ser Leu Ser Ser Gly Val His Thr Phe Pro Ala
            180                 185                 190

Val Leu Gln Ser Asp Leu Tyr Thr Leu Ser Ser Ser Val Thr Val Pro
        195                 200                 205

Ser Ser Thr Trp Pro Ser Glu Thr Val Thr Cys Asn Val Ala His Pro
210                 215                 220

Ala Ser Ser Thr Lys Val Asp Lys Lys Ile Val Pro Arg Asp Cys
225                 230                 235

<210> SEQ ID NO 9
<211> LENGTH: 471
<212> TYPE: DNA
<213> ORGANISM: Artificial Sequence
<220> FEATURE:
<223> OTHER INFORMATION: Synthetic construct: MAb 83-7 IgG1 heavy chain

<400> SEQUENCE: 9
atggctgtcc tggcattact cttctgcctg gcaacattcc ccagctgtat cctttcccag    60
gtgcagctga aggagtcagg acctggcctg gtggcgccct cacagagcct gtccatcaca   120
tgcaccgtct cagggttccc attaaccgcc tatggtgtta actgggttcg ccagcctcca   180
ggaaagggtc tggagtggct gggaatgata tggggtgatg gaaacacaga ctataattca   240
gctctcaaat ccagactgag catcagcaag gacaactcca agagccaagt tttcttaaaa   300
atgaacagtc tgcaaactga tgacacagcc aggtactact gtgccagaga ccctacggt    360
agtaagccta tggactattg gggtcaagga acctcggtca ctgtctcctc agccaaaacg   420
acacccccat ctgtctatcc actggcccct ggatctgctg cccaaactaa c            471
```

<210> SEQ ID NO 10
<211> LENGTH: 239
<212> TYPE: PRT
<213> ORGANISM: Artificial Sequence
<220> FEATURE:
<223> OTHER INFORMATION: Synthetic construct: MAb 83-7 kappa light chain

<400> SEQUENCE: 10

```
Met Asp Ser Gln Ala Gln Val Leu Met Leu Leu Leu Trp Ile Ser
1               5                  10                  15

Gly Thr Cys Gly Asp Ile Val Met Ser Gln Ser Pro Ser Leu Val
            20                  25                  30

Val Ser Val Gly Glu Lys Val Thr Met Ser Cys Lys Ser Gln Ser
        35                  40                  45

Leu Leu Tyr Ser Ser Asn Gln Lys Asn Phe Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Lys Ala Glu Asp Leu Ala Val Tyr
            100                 105                 110

Tyr Cys Gln Gln Tyr Phe Arg Tyr Arg Thr Phe Gly Gly Gly Thr Lys
        115                 120                 125

Leu Glu Ile Lys Arg Ala Asp Ala Ala Pro Thr Val Ser Ile Phe Pro
    130                 135                 140

Pro Ser Ser Glu Gln Leu Thr Ser Gly Gly Ala Ser Val Val Cys Phe
145                 150                 155                 160

Leu Asn Asn Phe Tyr Pro Lys Asp Ile Asn Val Lys Trp Lys Ile Asp
                165                 170                 175

Gly Ser Glu Arg Gln Asn Gly Val Leu Asn Ser Trp Thr Asp Gln Asp
            180                 185                 190

Ser Lys Asp Ser Thr Tyr Ser Met Ser Ser Thr Leu Thr Leu Thr Lys
        195                 200                 205

Asp Glu Tyr Glu Arg His Asn Ser Tyr Thr Cys Glu Ala Thr His Lys
    210                 215                 220

Thr Ser Thr Ser Pro Ile Val Lys Ser Phe Asn Arg Gly Glu Cys
225                 230                 235
```

<210> SEQ ID NO 11
<211> LENGTH: 423
<212> TYPE: DNA
<213> ORGANISM: Artificial Sequence
<220> FEATURE:
<223> OTHER INFORMATION: Synthetic construct: Mab 83-7 kappa light chain

<400> SEQUENCE: 11

```
atggattcac aggcccaggt tcttatgtta ctgctgctat ggatatctgg tacctgtggg    60
gacattgtga tgtcacagtc tccatcctcc ctagttgtgt cagttggaga gaaggttact   120
atgagctgta agtccagtca gagccttttta tatagtagca atcagaagaa cttcttggcc   180
tggtaccagc agaaaccagg gcagtctcct aaactgctga tttactgggc atccactagg   240
gaatctgggg tccctgatcg cttcacaggc agtggatctg gacagatttt cactctcacc   300
atcagcagtg tgaaggctga agacctggca gtttattact gtcagcaata ttttaggtat   360
cggacgttcg agggaggcac caagctggaa atcaaacggg ctgatgctgc accaactgta   420
tcc                                                                  423
```

<210> SEQ ID NO 12
<211> LENGTH: 59
<212> TYPE: DNA
<213> ORGANISM: Artificial Sequence
<220> FEATURE:
<223> OTHER INFORMATION: Synthetic construct

<400> SEQUENCE: 12
gatctccgac gatgacgata aggaacaaaa actcatctca gaagaggatc tgaattagt    59

<210> SEQ ID NO 13
<211> LENGTH: 59
<212> TYPE: DNA
<213> ORGANISM: Artificial Sequence
<220> FEATURE:
<223> OTHER INFORMATION: Synthetic construct

<400> SEQUENCE: 13
ctagactaat tcacatcctc ttctgagatg agtttttgtt ccttatcgtc atcgtcgga    59

<210> SEQ ID NO 14
<211> LENGTH: 18
<212> TYPE: PRT
<213> ORGANISM: Artificial Sequence
<220> FEATURE:
<223> OTHER INFORMATION: Synthetic construct

<400> SEQUENCE: 14

Ile Ser Asp Asp Asp Asp Lys Glu Gln Lys Leu Ile Ser Glu Glu Asp
1               5                   10                  15

Leu Asn

<210> SEQ ID NO 15
<211> LENGTH: 898
<212> TYPE: PRT
<213> ORGANISM: Artificial Sequence
<220> FEATURE:
<223> OTHER INFORMATION: Synthetic construct

<400> SEQUENCE: 15

His Leu Tyr Pro Gly Glu Val Cys Pro Gly Met Asp Ile Arg Asn Asn
1               5                   10                  15

Leu Thr Arg Leu His Glu Leu Glu Asn Cys Ser Val Ile Glu Gly His
                20                  25                  30

Leu Gln Ile Leu Leu Met Phe Lys Thr Arg Pro Glu Asp Phe Arg Asp
            35                  40                  45

Leu Ser Phe Pro Lys Leu Ile Met Ile Thr Asp Tyr Leu Leu Leu Phe
        50                  55                  60

Arg Val Tyr Gly Leu Glu Ser Leu Lys Asp Leu Phe Pro Asn Leu Thr
65                  70                  75                  80

Val Ile Arg Gly Ser Arg Leu Phe Phe Asn Tyr Ala Leu Val Ile Phe
                85                  90                  95

Glu Met Val His Leu Lys Glu Leu Gly Leu Tyr Asn Leu Met Asn Ile
            100                 105                 110

Thr Arg Gly Ser Val Arg Ile Glu Lys Asn Asn Glu Leu Cys Tyr Leu
        115                 120                 125

Ala Thr Ile Asp Trp Ser Arg Ile Leu Asp Ser Val Glu Asp Asn His
    130                 135                 140

Ile Val Leu Asn Lys Asp Asp Asn Glu Glu Cys Gly Asp Ile Cys Pro
145                 150                 155                 160

Gly Thr Ala Lys Gly Lys Thr Asn Cys Pro Ala Thr Val Ile Asn Gly
                165                 170                 175

-continued

```
Gln Phe Val Glu Arg Cys Trp Thr His Ser His Cys Gln Lys Val Cys
            180                 185                 190

Pro Thr Ile Cys Lys Ser His Gly Cys Thr Ala Glu Gly Leu Cys Cys
            195                 200                 205

His Ser Glu Cys Leu Gly Asn Cys Ser Gln Pro Asp Asp Pro Thr Lys
            210                 215                 220

Cys Val Ala Cys Arg Asn Phe Tyr Leu Asp Gly Arg Cys Val Glu Thr
225                 230                 235                 240

Cys Pro Pro Pro Tyr Tyr His Phe Gln Asp Trp Arg Cys Val Asn Phe
                245                 250                 255

Ser Phe Cys Gln Asp Leu His His Lys Cys Lys Asn Ser Arg Arg Gln
            260                 265                 270

Gly Cys His Gln Tyr Val Ile His Asn Asn Lys Cys Ile Pro Glu Cys
            275                 280                 285

Pro Ser Gly Tyr Thr Met Asn Ser Ser Asn Leu Leu Cys Thr Pro Cys
            290                 295                 300

Leu Gly Pro Cys Pro Lys Val Cys His Leu Leu Glu Gly Glu Lys Thr
305                 310                 315                 320

Ile Asp Ser Val Thr Ser Ala Gln Glu Leu Arg Gly Cys Thr Val Ile
                325                 330                 335

Asn Gly Ser Leu Ile Ile Asn Ile Arg Gly Gly Asn Asn Leu Ala Ala
            340                 345                 350

Glu Leu Glu Ala Asn Leu Gly Leu Ile Glu Glu Ile Ser Gly Tyr Leu
            355                 360                 365

Lys Ile Arg Arg Ser Tyr Ala Leu Val Ser Leu Ser Phe Phe Arg Lys
            370                 375                 380

Leu Arg Leu Ile Arg Gly Glu Thr Leu Glu Ile Gly Asn Tyr Ser Phe
385                 390                 395                 400

Tyr Ala Leu Asp Asn Gln Asn Leu Arg Gln Leu Trp Asp Trp Ser Lys
                405                 410                 415

His Asn Leu Thr Thr Thr Gln Gly Lys Leu Phe Phe His Tyr Asn Pro
            420                 425                 430

Lys Leu Cys Leu Ser Glu Ile His Lys Met Glu Glu Val Ser Gly Thr
            435                 440                 445

Lys Gly Arg Gln Glu Arg Asn Asp Ile Ala Leu Lys Thr Asn Gly Asp
450                 455                 460

Lys Ala Ser Cys Glu Asn Glu Leu Leu Lys Phe Ser Tyr Ile Arg Thr
465                 470                 475                 480

Ser Phe Asp Lys Ile Leu Leu Arg Trp Glu Pro Tyr Trp Pro Pro Asp
                485                 490                 495

Phe Arg Asp Leu Leu Gly Phe Met Leu Phe Tyr Lys Glu Ala Pro Tyr
            500                 505                 510

Gln Asn Val Thr Glu Phe Asp Gly Gln Asp Ala Cys Gly Ser Asn Ser
            515                 520                 525

Trp Thr Val Val Asp Ile Asp Pro Pro Leu Arg Ser Asn Asp Pro Lys
            530                 535                 540

Ser Gln Asn His Pro Gly Trp Leu Met Arg Gly Leu Lys Pro Trp Thr
545                 550                 555                 560

Gln Tyr Ala Ile Phe Val Lys Thr Leu Val Thr Phe Ser Asp Glu Arg
                565                 570                 575

Arg Thr Tyr Gly Ala Lys Ser Asp Ile Ile Tyr Val Gln Thr Asp Ala
            580                 585                 590

Thr Asn Pro Ser Val Pro Leu Asp Pro Ile Ser Val Ser Asn Ser Ser
            595                 600                 605
```

-continued

```
Ser Gln Ile Ile Leu Lys Trp Lys Pro Pro Ser Asp Pro Asn Gly Asn
    610             615             620
Ile Thr His Tyr Leu Val Phe Trp Glu Arg Gln Ala Glu Asp Ser Glu
625             630             635             640
Leu Phe Glu Leu Asp Tyr Cys Leu Lys Gly Leu Lys Leu Pro Ser Arg
                645             650             655
Thr Trp Ser Pro Pro Phe Glu Ser Glu Asp Ser Gln Lys His Asn Gln
            660             665             670
Ser Glu Tyr Glu Asp Ser Ala Gly Glu Cys Cys Ser Cys Pro Lys Thr
        675             680             685
Asp Ser Gln Ile Leu Lys Glu Leu Glu Glu Ser Ser Phe Arg Lys Thr
    690             695             700
Phe Glu Asp Tyr Leu His Asn Val Val Phe Val Pro Arg Pro Ser Arg
705             710             715             720
Lys Arg Arg Ser Leu Gly Asp Val Gly Asn Ala Gly Asn Asn Glu Glu
                725             730             735
His Arg Pro Phe Glu Lys Val Val Asn Lys Glu Ser Leu Val Ile Ser
            740             745             750
Gly Leu Arg His Phe Thr Gly Tyr Arg Ile Glu Leu Gln Ala Cys Asn
        755             760             765
Gln Asp Thr Pro Glu Glu Arg Cys Ser Val Ala Ala Tyr Val Ser Ala
    770             775             780
Arg Thr Met Pro Glu Ala Lys Ala Asp Asp Ile Val Gly Pro Val Thr
785             790             795             800
His Glu Ile Phe Glu Asn Asn Val Val His Leu Met Trp Gln Glu Pro
                805             810             815
Lys Glu Pro Asn Gly Leu Ile Val Leu Tyr Glu Val Ser Tyr Arg Arg
            820             825             830
Tyr Gly Asp Glu Glu Leu His Leu Cys Val Ser Arg Lys His Phe Ala
        835             840             845
Leu Glu Arg Gly Cys Arg Leu Arg Gly Leu Ser Pro Gly Asn Tyr Ser
    850             855             860
Val Arg Ile Arg Ala Thr Ser Leu Ala Gly Asn Gly Ser Trp Thr Glu
865             870             875             880
Pro Thr Tyr Phe Tyr Val Thr Asp Tyr Leu Asp Val Pro Ser Asn Ile
                885             890             895
Ala Lys
```

STRUCTURE OF THE INSULIN RECEPTOR ECTODOMAIN

CROSS REFERENCE TO RELATED APPLICATIONS

This application is a 35 USC §371 National Stage application of International Application No. PCT/US2007/000869 filed Jun. 22, 2007, now pending; which claims the benefit under 35 USC §119(a) to Australia Patent Application No. 2006903378 filed Jun. 22, 2006. The disclosure of each of the prior applications is considered part of and is incorporated by reference in the disclosure of this application.

FIELD OF THE INVENTION

The present invention relates generally to structural studies of the insulin receptor. More particularly, the present invention relates to the crystal structure of the insulin receptor ectodomain, to the nature of its N-linked glycans and to methods of using the crystal and related structural information to screen for and design compounds that interact with or modulate the insulin receptor and/or the closely-related insulin-like growth factor receptors or variants thereof.

BACKGROUND TO THE INVENTION

The insulin receptor (IR) and its homologue the type 1 insulin-like growth factor 1 receptor (IGF-1R), are closely related members of the tyrosine kinase receptor family and are large, transmembrane, glycoprotein dimers consisting of several structural domains.

The key role of the insulin receptor (IR) is in glucose uptake and metabolism by muscle and fat. Mouse knockout studies have also shown IR to be important in adipogenesis, neovascularization, the regulation of hepatic glucose synthesis and glucose-induced pancreatic insulin secretion (Kitamura et al., 2003). IR signalling is also important in the brain, being involved in the regulation of food intake, peripheral fat deposition and the reproductive endocrine axis as well as in learning and memory (Wada et al., 2005). Dysfunctional IR signalling has been implicated in diseases including type I and type II diabetes, dementia and cancer.

IR exists as two splice variant isoforms, IR-A and IR-B, which respectively lack or contain the 12 amino acids coded by exon 11. The longer variant, IR-B, is the isoform responsible for signalling metabolic responses. In contrast, IR-A signals predominantly mitogenic responses, is the preferentially expressed isoform in several cancers (Denley et al., 2003) and is capable of binding insulin-like growth factor 2 (IGF-II) with high affinity (Denley et al., 2004).

The sequence of IR is highly homologous to the sequence of IGF-1R, indicating that the three-dimensional structures of both receptors may be similar. The mature human IR and IGF-1R molecules are each homodimers comprising two α-chains and two β-chains, the α-and β-chains arising from the post-translational cleavage at the furin cleavage site at residues 720-723 (IR-A numbering with the mature N-terminal residue numbered 1) or 707-710 (IGF-1R). The structural organization of IR and IGF-1R has been reviewed extensively (Adams et al., 2000; De Meyts & Whittaker, 2002; Ward et al., 2003) and is summarized schematically in FIG. 1

Each IR or IGF-1R monomer contains a leucine-rich repeat domain (L1), a cysteine-rich region (CR) and a second leucine-rich repeat domain (L2), followed by three fibronectin type III domains, (FnIII-1, -2 and -3). The FnIII-2 domain contains a large insert domain (ID) of approximately 120 residues, within which lies the α-β cleavage site. Intracellularly, each monomer contains a tyrosine kinase catalytic domain flanked by two regulatory regions that contain the phosphotyrosine binding sites for signalling molecules. Each α-chain is linked to its partner β-chain via a disulphide bond between residues Cys647 and Cys860 (Sparrow et al., 1997) in the case of IR and/or Cys633-Cys849 in the case of IGF-1R. The α-chains of both IR and IGF-1R are cross-linked by disulphide bonds in two places. The first is at Cys524 (IR) or Cys514 (IGF-1R) in the FnIII-1 domain, cross-linked to its counterpart in the opposite monomer, and the second involves one or more of the residues Cys682, Cys683 and Cys685 (IR) or Cys669, Cys670 and Cys672 (IGF-1R) in the insert region of each FnIII-2 domain, cross-linked to their counterparts in the opposite monomer (Sparrow et al., 1997).

The domains of IR and IGF-1R exhibit high (47-67%) amino acid identity indicative of high conservation of three-dimensional structure. The crystal structure of the first three domains of IGF-1R (L1-CR-L2) has been determined (Garrett et al., 1998) and revealed that the L domains consist of a single-stranded right-handed β-helix (a helical arrangement of β-strands), while the cysteine-rich region is composed of eight related disulfide-bonded modules. The structures of IR and IGF-1R are known to be very similar from: (i) electron microscopic analyses (Tulloch et al., 1999), (ii) the fact that hybrid receptors (heterodimers of one IR monomer disulphide-bonded to one of IGF-1R monomer) exist naturally and are commonly found in tissues expressing both receptors (Bailyes et al., 1997), and (iii) the fact that receptor chimeras can be constructed which have whole domains or smaller segments of polypeptide from one receptor replaced by the corresponding domain or sequence from the other (reviewed in Adams et al., 2000).

The current model for insulin binding proposes that, in the basal state, the IR homodimer contains two identical pairs of binding sites (referred to as Site 1 and Site 2) on each monomer (De Meyts & Whittaker, 2002; Schaffer, 1994; De Meyts, 1994; De Meyts 2004). Binding of insulin to a low affinity site (Site 1) on one α-subunit is followed by a second binding event between the bound insulin and a different region of the second IR α-subunit (Site 2). This ligand-mediated bridging between the two α-subunits generates the high affinity state that results in signal transduction. In contrast, soluble IR ectodomain, which is not tethered at its C-terminus, cannot generate the high affinity receptor-ligand complex. It can bind two molecules of insulin simultaneously at its two Site 1s, but only with low affinity (Adams et al., 2000). The model for IGF-I or IGF-II binding to IGF-1R is the same as that just described for insulin binding to IR and involves a low affinity site (Site 1) and a high affinity site (Site 2) on each monomer as described for the IR.

While similar in structure, IGF-1R and IR serve different physiological functions. IGF-1R is expressed in almost all normal adult tissue except for liver, which is itself the major site of IGF-I production (Buttel et al., 1999). A variety of signalling pathways are activated following binding of IGF-I or IGF-II to IGF-1R, including Src and Ras, as well as downstream pathways, such as the MAP kinase cascade and the P13K/AKT axis (Chow et al., 1998). IR is primarily involved in metabolic functions whereas IGF-1R mediates growth and differentiation. Consistent with this, ablation of IGF-I (i.e. in IGF-I knock-out mice) results in embryonic growth deficiency, impaired postnatal growth, and infertility. In addition, IGF-1R knock-out mice were only 45% of normal size and died of respiratory failure at birth (Liu et al., 1993). However, both insulin and IGF-I can induce both mitogenic and metabolic effects.

Various 3-D structural analyses of the IR and the interaction of insulin with the IR have been undertaken (Luo et al., 1999; Ottensmeyer et al., 2000, 2001; Yip & Ottensmeyer, 2001). However, these have all been based on non-crystallographic electron microscopic techniques of low resolution (>20 angstrom) and their conclusions have been questioned (De Meyts & Whittaker, 2002). The absence of high resolution data on the IR ectodomain and insulin/IR complex has hindered elucidation of the nature of ligand/IR interactions.

SUMMARY OF THE INVENTION

We have now determined the crystal structure of the first three domains (L1-CR-L2) of human IR. We have also successfully produced crystals of the intact homodimeric ectodomain fragment of human IR and elucidated the three dimensional (3-D) structure of this homodimer using X-ray crystallography.

This data allows direct comparison, for the first time, of the regions controlling ligand specificity in IR and the closely related homologue IGF-1R, and identifies critical regions of IR involved in the initial binding of insulin and in the subsequent formation of the high affinity insulin-IR complex that leads to signal transduction. Such information also indicates, by analogy, the corresponding regions in the closely related IGF-1R that are involved in insulin growth factor (IGF) binding and in the formation of the high affinity IGF/IGF-1R signalling complex.

The identification of molecular structures having a high degree of specificity for one or the other receptor is important in the development of efficacious and safe therapeutics. For example, a molecule developed as an insulin agonist should have little or no IGF-I activity in order to avoid the mitogenic activity of IGF-I and a potential for facilitating neoplastic growth. The determination of which regions of IR and IGF-1R have sufficient differences to confer selectivity for their respective ligands or for therapeutic molecules such as chemical entities or biological reagents is therefore an important and significant advancement. Similarly, it is believed that the ability to be able to identify molecular structures that mimic the active binding regions of insulin and/or IGF-I and which impart selective agonist or antagonist activity will also aid and advance the development of new drugs.

The region of IR ectodomain consisting essentially of the first three domains of the ectodomain is referred to herein as "LCL IR ectodomain".

Accordingly, the present invention provides a method of structure-based identification or design of a compound that interacts with IR, comprising performing structure-based identification or design of a compound that interacts with IR using the structure defined by the atomic coordinates of Appendix I and/or Appendix II.

To further assist in the design of such a compound, we have also used these structures to place a model of a modified insulin molecule in the binding site. This model, with coordinates in Appendix III, is oriented relative to atomic coordinates found in Appendix II and may be used in conjunction with atomic coordinates of Appendix I and/or Appendix II to design a compound which binds to IR.

In one embodiment the present invention provides a method for identifying or designing a compound that can potentially interact with IR, the method comprising designing or screening for a compound which interacts with the three-dimensional structure of; (i) IR ectodomain, the structure being defined by the atomic coordinates shown in Appendix I, a subset of the atomic coordinates shown in Appendix I in combination with the atomic coordinates shown in Appendix II or a subset of the atomic coordinates shown in Appendix I in combination with a subset of the atomic coordinates shown in Appendix II; (ii) a region of IR ectodomain, the structure being defined by the atomic coordinates shown in Appendix II, a subset of the atomic coordinates shown in Appendix I in combination with a subset of the atomic coordinates shown in Appendix II or a subset of the atomic coordinates shown in Appendix I or Appendix II; (iii) IR ectodomain as defined in (i) in combination with the atomic coordinates given in Appendix III and/or Appendix IV, or in combination with a subset of the atomic coordinates given in Appendix III and/or Appendix IV; or (iv) a region of IR ectodomain as defined in (ii) in combination with the atomic coordinates given in Appendix III and/or Appendix IV, or in combination with a subset of the atomic coordinates given in Appendix III and/or Appendix IV; wherein interaction of the compound with the structure is favoured energetically.

In a preferred embodiment, the method further comprises synthesising or obtaining a candidate compound designed or screened for in the first step and determining the ability of the candidate compound to interact with IR.

With regards to defining structures by combining subsets of coordinates from Appendix I and Appendix II, such combinations may be achieved by methods such as assembling combinations of complete domains from each set, assembling combinations of complete domains from each set wherein the coordinates and corresponding amino acid sequence from one structure are transposed onto those of the other, refining less resolved regions of one crystal using the corresponding coordinates of the other.

In a further embodiment, the invention provides a method of identifying or designing a compound which interacts with a target binding site of IR ectodomain.

In a preferred embodiment, the target binding site comprises one or more regions of IR ectodomain that governs specificity, i.e. one or more regions defining the low affinity binding site for insulin.

In a further embodiment, van der Waals and/or hydrophobic interactions account for the major portion of the binding energy between a compound and a low affinity binding site of IR.

In another preferred embodiment, the target binding site comprises one or more regions of IR ectodomain defining the high affinity binding site for insulin (which leads to the initiation of IR autophosphorylation).

The present invention also provides compounds that bind to IR ectodomain identified or designed using any suitable method of invention. In particular, the present invention provides compounds which bind to one or more regions of the low and/or high affinity binding site(s) for insulin identified or designed as described above.

The crystal structure of the first three domains of the ectodomain of IGF-1R has been previously reported (WO 99/028347). As will be evident to the skilled person, the structural data presented herein has now enabled, for the first time, direct comparison of the regions controlling ligand specificity in the closely related IGF-1R and IR. The crystal structure of the remaining regions of the IGF-1R ectodomain have yet to be elucidated. However, as will be evident to the skilled person, the findings presented herein on IR ectodomain structure, shape and orientation can be transposed onto the IGF-1R ectodomain structure, shape and orientation.

The present invention has also identified the critical regions of IR involved in the initial binding of insulin and in the subsequent formation of the high affinity insulin-IR complex that leads to signal transduction. Once again, it will be evident to the skilled person that these findings can be transposed onto IGF-1R.

The present invention is therefore also useful in the identification and/or design of compounds which bind to IGF-1R.

The present invention has enabled the identification of previously unrecognised target binding sites in IR ectodomain, i.e. regions of IR ectodomain involved in the initial docking of insulin and the subsequent high affinity binding leading to signal transduction. By analogy, the present invention also identifies the equivalent regions in the IGF-1R, given the structural organisation of domains in the two receptors is the same.

The present invention has also enabled the N-linked glycosylation sites of IR and IGF-1R ectodomains to be mapped onto the 3D structure of these molecules and for the glycan moieties at each site to be modeled based on the chemical compositions determined in this invention and the known structures of N-linked glycans from the protein data bank. Such mapping and modeling enables the identification of regions on the surface of these receptors that are devoid of such carbohydrate and as such more amenable to the selection and design of potential binding molecules, particularly antibody and nonimmunoglobulin binding proteins and aptamers. This allows compounds that specifically target these regions to be designed and manufactured.

Candidate compounds and compounds identified or designed using a method of the present invention may be any suitable compound, including naturally occurring compounds, de novo designed compounds, library generated compounds (chemically or recombinantly generated), mimetics etc., and include organic compounds, new chemical entities, antibodies, binding proteins other than antibody-based molecules (nonimmunoglobulin proteins) including, for example, protein scaffolds such as lipocalins, designed ankyrin repeat proteins (DARPins) and protein A domains (reviewed in Binz H K et al, 2005), avimers (Silverman et al., 2005), and other new biological entities such as nucleic acid aptamers (reviewed in Ulrich, 2006).

In another preferred embodiment, a compound is a new chemical entity.

The present invention provides a compound capable of binding to at least one target binding site and/or specific target molecule as defined by the present invention. Preferably, such compounds have an affinity ($K_d$) for IR of less than $10^{-5}$, preferably less than $10^{-7}$ M and more preferably less than $10^{-10}$ M.

Particularly preferred compounds are those capable of binding to a target binding site involved in the high affinity binding of insulin and/or a specific target molecule indicative of the capacity to bind to a target binding site.

In a preferred embodiment, such a compound is an antibody or antibody fragment.

In further embodiments, such a compound is a novel binding protein comprising nonimmunoglobulin domains such as avimers (Silverman et al., 2005), DARPins (Binz et al., 2005) or lipocalins (Schlehuber & Skerra, 2005) or a nucleic acid based binding entity such as an aptamer (reviewed in Ulrich, 2006).

The present invention is also useful in the identification and/or design of compounds which bind to IGF-1R. For example, known IGF-1R binding compounds can be screened against the 3D structure of IR ectodomain or a region of IR ectodomain based on the coordinates given in Appendix I and/or II or a portion thereof (optionally utilising the atomic coordinates given in Appendix III to further refine the screen and/or the assessment of the potential for binding to IR), and an assessment made of their potential for binding to IR. Alternatively, existing IGF-1R ligands which are known to bind to IR (i.e. which are non- or insufficiently selective) can be redesigned so as to be more selective for IGF-1R. For example, such ligands can be screened against a 3D structure of the IR ectodomain, those areas of energetically favoured interaction of the ligand with the IR ectodomain identified, and the ligands redesigned (i.e. modified) so as to reduce the potential to energetically interact with IR.

The present invention is also useful for improving the properties of known ligands for both IR and IGF-1R. For example, existing IR or IGF-1R ligands can be screened against the 3D structure of IR ectodomain or a region of IR ectodomain defined by the atomic coordinates of Appendix I and/or Appendix II or a portion thereof (optionally utilising the atomic coordinates given in Appendix III to further refine the screen and/or the assessment of the potential to energetically interact with IR), and an assessment made of the potential to energetically interact with IR. In the case of IR, the compound could be redesigned (e.g. chemically modified) so as to improve and/or impart one or more properties such as, for example: (i) improved affinity for the low affinity binding site of IR (i.e. the binding site governing selectivity), (ii) improved affinity for the high affinity binding site for IR (i.e. the binding site governing signal transduction) and (iii) lowered affinity for binding to IGF-1R. In the case of IGF-1R, the compound could be redesigned (i.e. chemically modified) so as to improve and/or impart one or more of the properties such as, for example: (i) reduced affinity for the low affinity binding site of IR (i.e. the binding site governing selectivity) and (ii) improved affinity for binding to IGF-1R.

When screening existing ligands or potential compounds for selectivity for binding to IR or IGF-1R, it will be important to concentrate on those areas of difference in the 3D structure between the ectodomains of IR and IGF-1R. Such areas are identified and described herein. In particular, it will be important to concentrate on those areas of difference which are identified as being potentially important in the binding of the respective ligands to the receptors.

The methods of the present invention may be used for either targeted or broad screening. Targeted screening involves the design and synthesis of chemical compounds that are analogs of some active compounds or that can specifically act with the biological target under investigation. Broad screening involves the design and synthesis of a large array of maximally diverse chemical compounds, leading to diverse libraries that are tested against a variety of biological targets.

The present invention also provides isolated molecules which represent or mimic regions of IR ectodomain to be targeted for the selection of binding molecules ("specific target molecules"), and which are identified and/or designed based on the 3D structure of a region of IR ectodomain defined by the atomic coordinates of Appendix I and/or Appendix II, or a subset thereof of both or either, optionally in combination with the atomic coordinates of Appendix IV or a subset of the atomic coordinates of Appendix IV. The specific target molecules may be conformationally constrained, for example, as in constrained peptide sequences, or may comprise domains or segments in an IR/IGF-1R chimera, or alternatively molecules which are not conformationally constrained such as, for example, non-constrained peptide sequences.

In a preferred embodiment, a molecule mimics a region of IR ectodomain which is involved in the binding of insulin, i.e. it mimics a target binding site. Those preferred regions described above in relation to the screening methods are equally applicable to the design of specific target molecules (i.e. target site binding comprising/mimicking molecules).

Molecules which mimic or represent a region of IR ectodomain involved in binding insulin can be used to screen for ligands, binding proteins or other binding entities which bind to IR. Additionally, such mimetics can be used to screen for ligands which selectively bind IR over IGF-1R.

In a preferred embodiment, the mimetic mimics, at least in part, the high affinity binding site of IR for insulin.

In a preferred embodiment, the mimetic is an isolated conformationally constrained peptide or peptidomimetic. In a preferred embodiment, the conformationally constrained peptide or peptidomimetic comprises at least one of the following: (i) the L1 binding face in general and the region governing specificity around Phe39 or the loop comprising residues 85-91 in the fourth LRR rung of L1 in particular, (ii) module 6 of the CR domain, (iii) the AB loop of FnIII-1, the CC' loop of FnIII-1 and the EF loop of FnIII-1 which comprise the high affinity binding site for ligand, and (iv) any other regions of the receptor implicated in ligand binding and signal transduction.

Preferably, the compound is a peptidomimetic that has fewer than 30 amino acids, more preferably fewer than 25 amino acids.

In one embodiment, the specific target molecule comprises at least one region from IR and at least one region from IGF-1R, i.e. it is a IR/IGF-1R chimera. Such chimeras are capable of presenting a target binding site in its native conformation. Furthermore, such chimeric specific target molecules may represent or mimic a first target binding site specific or at least more selective for binding of insulin and a second target binding site specific or more selective for binding insulin growth factor.

The present method further provides a method for preparing a pharmaceutical composition for treating diseases associated with aberrant IR or IGF-1R signalling in which the compound identified or designed according to the invention is incorporated into a pharmaceutical composition.

The present invention also provides a crystal of IR ectodomain polypeptide. In particular, the present invention provides a crystal of IR ectodomain polypeptide having a space group $C222_1$ with unit cell dimensions of a=123.0 Å, b=319.7 Å and c=204.9 Å with up to about 2% variation in any cell dimension.

The present invention also provides a crystal of LCL IR ectodomain polypeptide. In particular, the present invention provides a crystal of LCL IR ectodomain polypeptide having a space group $P2_12_12_1$ with unit cell dimensions a=103.86 Å, b=130.24 Å, c=160.92 Å with up to about 2% variation in any cell dimension.

The present invention also provides a crystalline composition comprising a crystal of IR ectodomain or LCL IR ectodomain. Such crystals may be used in X-ray diffraction studies for the screening of chemical fragments which may bind to the ectodomain of either receptor, such fragments then being assembled into compounds which may bind to the receptor with an affinity higher than that of the individual fragments.

The present invention also provides a computer system for identifying one or more compounds that can potentially interact with IR, the system containing data representing the structure of (i) IR ectodomain, the structure being defined by the atomic coordinates shown in Appendix I, a subset of the atomic coordinates shown in Appendix I in combination with the atomic coordinates shown in Appendix II or a subset of the atomic coordinates shown in Appendix I in combination with a subset of the atomic coordinates shown in Appendix II; (ii) a region of IR ectodomain, the structure being defined by the atomic coordinates shown in Appendix II, a subset of the atomic coordinates shown in Appendix I in combination with a subset of the atomic coordinates shown in Appendix II or a subset of the atomic coordinates shown in Appendix I or Appendix II; (iii) IR ectodomain as defined in (i) in combination with the atomic coordinates given in Appendix III and/or Appendix IV, or in combination with a subset of the atomic coordinates given in Appendix III and/or Appendix IV; or (iv) a region of IR ectodomain as defined in (ii) in combination with the atomic coordinates given in Appendix III and/or Appendix IV, or in combination with a subset of the atomic coordinates given in Appendix III and/or Appendix IV.

The present invention also provides a computer-readable media having recorded thereon data representing a model and/or the atomic coordinates of (i) an IR ectodomain crystal or (ii) an LCL IR ectodomain crystal.

Also provided is a computer-readable media having recorded thereon coordinate data according to Appendix I or Appendix II, or a subset thereof of either, where the coordinate data defines a three dimensional structure of IR ectodomain or a region of IR ectodomain.

Also provided is a computer-readable media having recorded thereon coordinate data according to Appendix III, or a subset thereof, where the coordinate data defines a three dimensional structure for insulin as it associates with IR as represented by atomic coordinates found in Appendix II.

The present invention also provides a set of coordinates as shown in Appendix I or Appendix II, or a subset thereof both or either, in which the coordinates define a three dimensional structure of IR ectodomain or a region of IR ectodomain.

The three-dimensional structure of IR ectodomain or a region thereof may be used to develop models useful for drug design and in silico screening of candidate compounds that interact with and/or modulate IR. Other physicochemical characteristics may also be used in developing the model, e.g. bonding, electrostatics etc.

Generally the term "in silico" refers to the creation in a computer memory, i.e., on a silicon or other like chip. Stated otherwise "in silico" means "virtual". When used herein the term "in silico" is intended to refer to screening methods based on the use of computer models rather than in vitro or in vivo experiments.

The present invention further provides a computer-based method of identifying a compound that potentially interacts with IR, which method comprises fitting the structure of (i) IR ectodomain having the atomic coordinates shown in Appendix I, a subset of the atomic coordinates shown in Appendix I in combination with the atomic coordinates shown in Appendix II or a subset of the atomic coordinates shown in Appendix I in combination with a subset of the atomic coordinates shown in Appendix II; (ii) a region of IR ectodomain having the atomic coordinates shown in Appendix II, a subset of the atomic coordinates shown in Appendix I in combination with a subset of the atomic coordinates shown in Appendix II or a subset of the atomic coordinates shown in Appendix I or Appendix II; (iii) IR ectodomain as defined in (i) in combination with the atomic coordinates given in Appendix III and/or Appendix IV, or in combination with a subset of the atomic coordinates given in Appendix III and/or Appendix IV; or (iv) a region of IR ectodomain as defined in (ii) in combination with the atomic coordinates given in Appendix III and/or Appendix IV, or in combination with a subset of the atomic coordinates given in Appendix III and/or Appendix IV; to the structure of a candidate compound.

The present invention further provides a computer-assisted method for identifying a compound able to interact with IR using a programmed computer comprising a processor, which method comprises the steps of: (a) generating, using computer methods, a set of atomic coordinates of a structure that possesses energetically favourable interactions with the atomic coordinates of: (i) IR ectodomain corresponding to the atomic coordinates shown in Appendix I, a subset of the atomic coordinates shown in Appendix I in combination with the atomic coordinates shown in Appendix II or a subset of the atomic coordinates shown in Appendix I in combination with a subset of the atomic coordinates shown in Appendix II; (ii) a region of IR ectodomain corresponding to the atomic coordinates shown in Appendix II, a subset of the atomic coordinates shown in Appendix I in combination with a subset of the atomic coordinates shown in Appendix II or a subset of the atomic coordinates shown in Appendix I or Appendix II; (iii) IR ectodomain as defined in (i) in combination with the atomic coordinates given in Appendix III and/or Appendix IV, or in combination with a subset of the atomic coordinates given in Appendix III and/or Appendix IV; or (iv) a region of IR ectodomain as defined in (ii) in combination with the atomic coordinates given in Appendix III and/or Appendix IV, or in combination with a subset of the atomic coordinates given in Appendix III and/or Appendix IV; which coordinates are entered into the computer, thereby generating a criteria data set; (b) comparing, using the processor, the criteria data set to a computer database of chemical structures; (c) selecting from the database, using computer methods, chemical structures which are complementary or similar to a region of the criteria data set; and, optionally, (d) outputting, to an output device, the selected chemical structures which are complementary to or similar to a region of the criteria data set.

Furthermore, the present invention provides a method for evaluating the ability of a chemical entity to interact with IR, the method comprising the steps of: (a) employing computational means to perform a fitting operation between the chemical entity and the binding surface of a computer model of at least one region of IR ectodomain using structure coordinates wherein the root mean square deviation between the structure coordinates and the structure coordinates set forth in Appendix I and/or Appendix II, or a subset thereof of both or either, is not more than 1.5 Å; and (b) analysing the results of the fitting operation to quantify the association between the chemical entity and the binding surface model.

Optionally, the atomic coordinates given in Appendix III and/or Appendix IV, or a subset of the atomic coordinates given in Appendix III and/or Appendix IV, may also be used to help define the binding surface of the computer model in step (a) and/or to analyse the fitting operation in step (b).

The model may be adaptive in a sense that it allows for slight surface changes to improve the fit between the candidate compound and the protein, e.g. by small movements in side chains or the main chain.

The IR ectodomain crystal structure and/or the LCL IR ectodomain crystal provided herein may also be used to model/solve the structure of a new crystal using molecular replacement.

Accordingly, the present invention provides a method of using molecular replacement to obtain structural information about a molecule or a molecular complex of unknown structure, comprising the steps of: (i) generating an X-ray diffraction pattern of the crystallized molecule or molecular complex; and (ii) applying at least a portion of the structure coordinates set forth in Appendix I and/or Appendix II to the X-ray diffraction pattern to generate a three-dimensional electron density map of at least a region of the molecule or molecular complex whose structure is unknown.

Preferably the molecule of unknown structure is IR or variant thereof.

In one embodiment, the molecular complex of unknown structure is a complex of IR, or variant thereof, and a ligand or candidate ligand.

In another embodiment the molecular complex of unknown structure is a complex of IR or IGF-1R and a monoclonal antibody or antibody fragment (Fab).

In another embodiment the molecular complex of unknown structure is a complex of IR or IGF-1R and a non-immunoglobulin binding protein such as an avimer, DARPin or lipocalin or an aptamer etc.

The present invention also provides a computer-assisted method for identifying potential mimetics of IR using a programmed computer comprising a processor, the method comprising the steps of: (a) generating a critria data set from a set of atomic coordinates of: (i) IR ectodomain corresponding to the atomic coordinates shown in Appendix I, a subset of the atomic coordinates shown in Appendix I in combination with the atomic coordinates shown in Appendix II or a subset of the atomic coordinates shown in Appendix I in combination with a subset of the atomic coordinates shown in Appendix II, or any of these preceding combinations in combination with the atomic coordinates shown in Appendix IV or a subset of the atomic coordinates shown in Appendix IV; or (ii) a region of IR ectodomain corresponding to the atomic coordinates shown in Appendix II, a subset of the atomic coordinates shown in Appendix I in combination with a subset of the atomic coordinates shown in Appendix II or a subset of the atomic coordinates shown in Appendix I or Appendix II, or any of these preceding combinations in combination with the atomic coordinates shown in Appendix IV or a subset of the atomic coordinates shown in Appendix IV; which coordinates are entered into the computer; (b) (i) comparing, using the processor, the criteria data set to a computer database of chemical structures stored in a computer data storage system and selecting from the database, using computer methods, chemical structures having a region that is structurally similar to the criteria data set; or (ii) constructing, using computer methods, a model of a chemical structure having a region that is structurally similar to the criteria data set; and, optionally, (c) outputting to the output device: (i) the selected chemical structures from step (b)(i) having a region similar to the criteria data set; or (ii) the constructed model from step (b)(ii).

A region of an IR ectodomain as referred to herein may be defined by a single amino acid (or side-chain thereof), by a continuous amino acid sequence or by two or more separate amino acids and/or stretches of amino acids. Such separate amino acids and/or stretches of amino acids may exist in close spatial proximity to one another in the three dimensional structure or may have the potential to be brought into close spatial proximity, for example, upon the binding of a suitable ligand. Suitably, regions of IR ectodomains comprise amino acid sequences involved in the binding of insulin, both the initial selective low affinity binding and the subsequent high affinity binding to the other monomer in the IR dimer.

Accordingly, the present invention provides a method for preventing or treating a disease associated with aberrant IR function which method comprises administering to a subject in need thereof a compound identified by a screening method of the invention.

Particular diseases associated with dysfunctional signalling by IR include obesity, type I and type II diabetes, cardiovascular disease, osteoporosis, dementia and cancer.

The present invention also provides a pharmaceutical composition comprising a compound identified by a screening method of the invention, which compound is able to interact (e.g. bind) with the ectodomain of IR and modulate an activity of the receptor, as well as a method of preventing or treating a disease associated with aberrant IR function (e.g. IR signalling) which method comprises administering to a subject in need thereof a composition of the invention.

The term "IR" as used herein includes wild-type IR and variants thereof including allelic variants and naturally occurring mutations and genetically engineered variants. The amino acid sequence of human IR is shown in Table 1. Reference to specific amino acid residue numbers or sequence numbering is with respect to the amino acid sequence as numbered in FIG. 2.

It will be readily apparent to the skilled person that IR ectodomains may be derived from other species not specifically disclosed herein. Furthermore, the skilled person will have no difficulties identifying such other suitable IR ectodomains or LCL IR ectodomains given the known conservation of IR sequences from primitive organisms through to mammals and humans. It will also be apparent to the skilled person through sequence alignment analysis of the respective amino acid sequences how the amino acid numbering system used herein can be applied to other IR ectodomains and where regions corresponding to those identified in the human IR ectodomain are found in other IR ectodomains.

As will be readily understood by those skilled in this field the methods of the present invention provide a rational method for designing and selecting compounds including antibodies and nonimmunoglobulin binding proteins which interact with IR ectodomain. In the majority of cases these compounds will require further development in order to increase activity. Such further development is routine in this field and will be assisted by the structural information provided in this application. It is intended that in particular embodiments the methods of the present invention includes such further developmental steps.

It is also intended that embodiments of the present invention include manufacturing steps such as incorporating the compound into a pharmaceutical composition in the manufacture of a medicament.

Throughout this specification, preferred aspects and embodiments apply, as appropriate, separately, or in combination, to other aspects and embodiments, mutatis mutandis, whether or not explicitly stated as such.

BRIEF DESCRIPTION OF THE FIGURES

FIG. 9: Nucleotide and derived amino acid sequences of the light (SEQ ID NO'S 11 & 10) and heavy chain (SEQ ID NO'S 9 & 8) variable regions of the Fab from the anti-insulin receptor monoclonal antibody 83-7. The translated amino acid sequence for the variable regions of the heavy (SE ID NO:8) and light (SEQ ID NO:10) chains of 83-7 was deduced from cDNA clones amplified from mRNA isolated from 83-7 hybridoma cells. For the light chain, the amplified region spanned the signal peptide (underlined), the variable region (residues 1-112) and proximal amino acids from the CH1 domain (113-121). For the heavy chain, the amplified region included the signal peptide (underlined), variable region (1-118) and proximal CH1 residues (119-138). The nucleotide sequence of the amplified cDNA is shown below the derived amino acid sequence. The three CDRs in each chain are indicated above the sequence. The additional CH1 amino acid sequences for both chains, together with hinge region residues down to the first cysteine, were obtained from published records.

FIG. 10: Nucleotide and derived amino acid sequences of the light (SEQ ID NO'S 7 & 6) and heavy chain (SEQ ID NO'S 5 & 4) variable regions of the Fab from the anti-insulin receptor monoclonal antibody 83-14. The translated amino acid sequence for the variable regions of the heavy (SEQ ID NO:4) and light (SEQ ID NO:6) chains of 83-14 was deduced from cDNA clones amplified from mRNA isolated from 83-14 hybridoma cells. For the light chain, the amplified region spanned the signal peptide (underlined), the variable region (residues 1-108) and proximal amino acids from the CH1 domain (109-117). For the heavy chain, the amplified region included the signal peptide (underlined), variable region (1-113) and proximal CH1 residues (113-127). The nucleotide sequence for the variable domains are shown below the derived amino acid sequence. The three CDRs in each chain are indicated above the sequence. The additional CH1 amino acid sequences for both chains, together with hinge region residues down to the first cysteine, were obtained from published records.

DETAILED DESCRIPTION OF THE INVENTION

Figure 1:
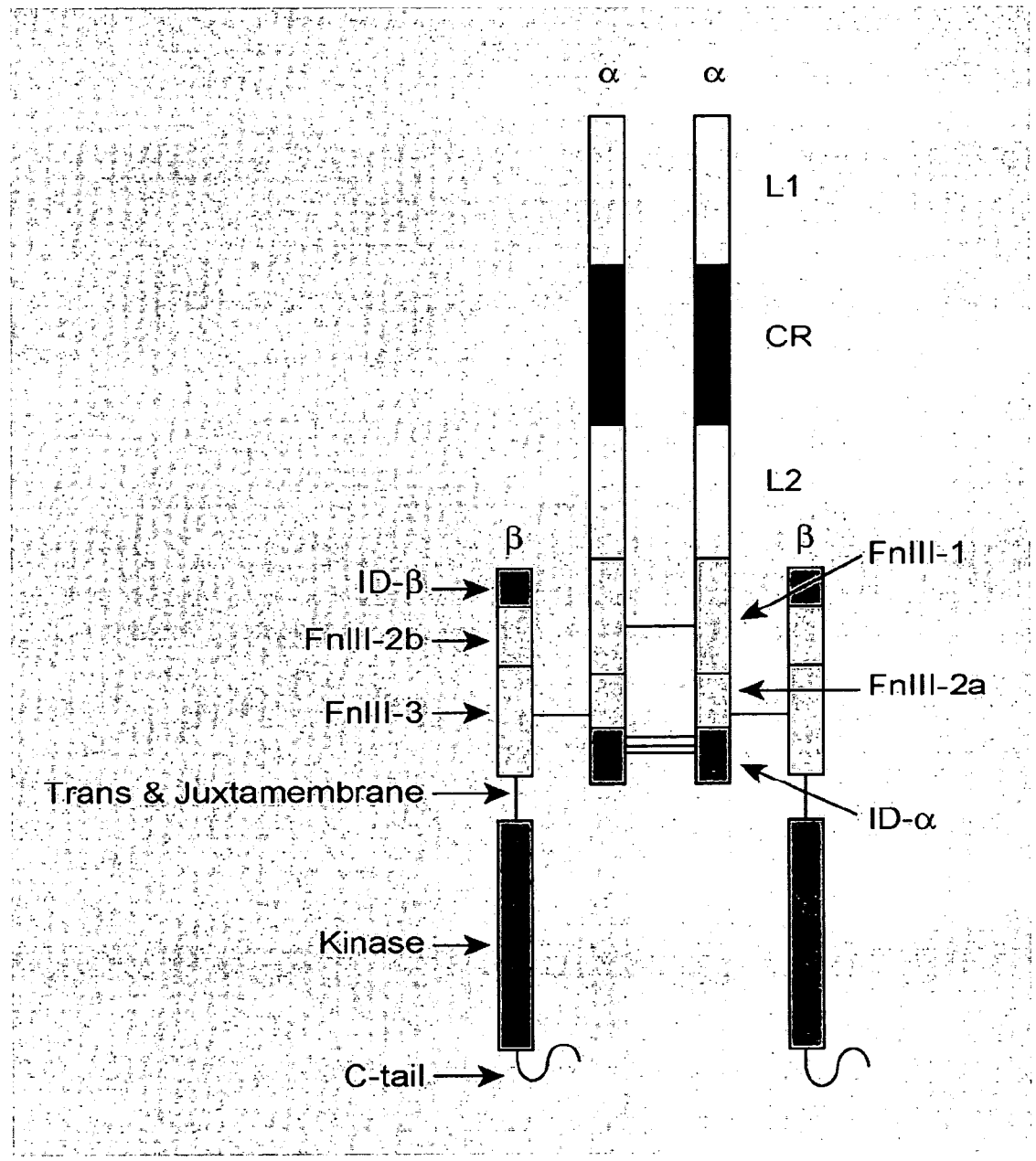
FIG. 1: Cartoon of the insulin receptor (IR) dimer showing the distribution of domains across the α-and β-chains and the approximate location of the α-β disulfides and the α-α dimer disulfide bonds. The leucine-rich repeat domains (L1 and L2), the cysteine-rich region (CR), the three fibronectin type III domains (FnIII-1, FnIII-2a and FnIII-2b, FnIII-3) and the insert region in the CC' loop of FnIII-2 (ID) are depicted. Inter-chain α-α disulphide bonds occur in two places (Cys524-Cys524 and at the triplet of Cys residues at 682, 683 and 685 in ID). There is only a single α-β disulphide (Cys647-Cys860) in each IR monomer.

Unless defined otherwise, all technical and scientific terms used herein have the same meaning as commonly understood by one of ordinary skill in the art (e.g. in molecular biology, biochemistry, structural biology, and computational biology). Standard techniques are used for molecular and biochemical methods (see generally, Sambrook et al., 2001, and Ausubel et al., 1999, which are incorporated herein by reference) and chemical methods.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

IR Ectodomain Crystals and Crystal Structures

The present invention provides a crystal comprising an IR (insulin receptor) ectodomain based on the IRΔβ construct (see Examples). Such crystals preferably are of the space group C222$_1$ with unit cell dimensions of a=123.0 Å, b=319.7 Å and c=204.9 Å.

The present invention also provides a crystal comprising an LCL IR ectodomain based on the IR485 (residues 1-485 of the insulin receptor as set forth in SEQ. ID. NO:1) construct (see Examples). Such crystals preferably are of space group P212121 with unit cell dimensions a=103.86 Å, b=130.24 Å, c=160.92 Å.

As used herein, the term "crystal" means a structure (such as a three dimensional (3D) solid aggregate) in which the plane faces intersect at definite angles and in which there is a regular structure (such as internal structure) of the constituent chemical species. The term "crystal" refers in particular to a solid physical crystal form such as an experimentally prepared crystal.

Crystals according to the invention may be prepared using any IR ectodomain, i.e. the IR polypeptide containing the extracellular domain and lacking the transmembrane domain and the intracellular tyrosine kinase domain. Typically, the extracellular domain comprises residues 1 to 917 (mature receptor numbering) of human IR, or the equivalent thereof together with any post-translational modifications of these residues such as N-or O-linked glycosylation.

In a preferred embodiment the IR polypeptide is human IR (GENBANK reference number NM_000208) or its exon 11-isoform. However, the IR polypeptide may also be obtained from other species, such as other mammalian, vertebrate or invertebrate species.

Crystals may be constructed with wild-type IR polypeptide ectodomain sequences or variants thereof, including allelic variants and naturally occurring mutations as well as genetically engineered variants. Typically, variants have at least 95 or 98% sequence identity with a corresponding wild-type IR ectodomain polypeptide.

Optionally, the crystal of IR ectodomain may comprise one or more molecules which bind to the ectodomain, or otherwise soaked into the crystal or cocrystallised with IR ectodomain. Such molecules include ligands or small molecules, which may be candidate pharmaceutical agents intended to modulate the interaction between IR and its biological targets. The crystal of IR ectodomain may also be a molecular complex with other receptors of the IGF receptor family such as IGF-1R. The complex may also comprise additional molecules such as the ligands to these receptors.

The production of IR ectodomain crystals is described below.

In a preferred embodiment, an IR ectodomain crystal of the invention has the atomic coordinates set forth in Appendix I. As used herein, the term "atomic coordinates" refer to a set of values which define the position of one or more atoms with reference to a system of axes. It will be understood by those skilled in the art that atomic coordinates may be varied, without affecting significantly the accuracy of models derived therefrom. Thus, although the invention provides a very precise definition of a preferred atomic structure, it will be understood that minor variations are envisaged and the claims are intended to encompass such variations.

It will be understood that any reference herein to the atomic coordinates or subset of the atomic coordinates shown in Appendix I or Appendix II shall include, unless specified otherwise, atomic coordinates having a root mean square deviation of backbone atoms of not more than 1.5 Å, preferably not more than 1 Å, when superimposed on the corresponding backbone atoms described by the atomic coordinates shown in Appendix I or Appendix II. Also, any reference to the atomic coordinates or subset of the atomic coordinates shown in Appendix III shall include, unless specified otherwise, atomic coordinates having a root mean square deviation of backbone atoms of not more than 2.5 Å when superimposed on the corresponding backbone atoms described by the atomic coordinates shown in Appendix III.

Preferred variants are those in which the root mean square deviation (RMSD) of the x, y and z co-ordinates for all backbone atoms other than hydrogen is less than 1.5 Å (preferably less than 1 Å, 0.7 Å or less than 0.3 Å) compared with the coordinates given in Appendix I. It will be readily appreciated by those skilled in the art that a 3D rigid body rotation and/or translation of the atomic coordinates does not alter the structure of the molecule concerned.

In a highly preferred embodiment, the crystal has the atomic coordinates as shown in Appendix I.

The present invention also provides a crystal structure of an IR ectodomain polypeptide, or a region thereof.

The atomic coordinates obtained experimentally for amino acids 4 to 655 and 755 to 909 (mature receptor numbering) of human IR ectodomain are shown in Appendix I. However, a person skilled in the art will appreciate that a set of atomic coordinates determined by X-ray crystallography is not without standard error. Accordingly, any set of structure coordinates for an IR ectodomain polypeptide that has a root mean square deviation of protein backbone atoms of less than 0.75 Å when superimposed (using backbone atoms) on the atomic coordinates listed in Appendix I shall be considered identical.

The present invention also comprises the atomic coordinates of an IR ectodomain region or polypeptide that substantially conforms to the atomic coordinates listed in Appendix I and/or Appendix II.

A structure that "substantially conforms" to a given set of atomic coordinates is a structure wherein at least about 50% of such structure has an RMSD of less than about 1.5 Å for the backbone atoms in secondary structure elements in each domain, and more preferably, less than about 1.3 Å for the backbone atoms in secondary structure elements in each domain, and, in increasing preference, less than about 1.0 Å, less than about 0.7 Å, less than about 0.5 Å, and most preferably, less than about 0.3 Å for the backbone atoms in secondary structure elements in each domain.

In a more preferred embodiment, a structure that substantially conforms to a given set of atomic coordinates is a structure wherein at least about 75% of such structure has the recited RMSD value, and more preferably, at least about 90% of such structure has the recited RMSD value, and most preferably, about 100% of such structure has the recited RMSD value.

In an even more preferred embodiment, the above definition of "substantially conforms" can be extended to include atoms of amino acid side chains. As used herein, the phrase "common amino acid side chains" refers to amino acid side chains that are common to both the structure which substantially conforms to a given set of atomic coordinates and the structure that is actually represented by such atomic coordinates.

The present invention also provides subsets of the atomic coordinates listed in Appendix I and/or Appendix II, preferably Appendix I, and subsets that conform substantially thereto. Preferred subsets define one or more regions of the human IR ectodomain selected from (i) the central β-sheet of L1, (ii) the central modules of CR, (iii) the AB loop of FnIII-1, (iv) the CC' loop of FnIII-1, (v) the EF loop of FnIII-1 and (vi) FnIII-2. Of the central β-sheet of L1, the region preferably defines at least the region including Phe39 in the $2^{nd}$ rung of the L1 face and the inserted loop comprising residues 86-91 in the 4th rung of the L1 face. Of the central modules of CR, the region preferably defines at least module 6.

The present invention also provides subsets of the atomic coordinates listed in Appendix III.

It will be appreciated that a set of structure coordinates for a polypeptide is a relative set of points that define a shape in three dimensions. Thus, it is possible that an entirely different set of coordinates could define a similar or identical shape. Moreover, slight variations in the individual coordinates will have little effect on overall shape.

The variations in coordinates may be generated due to mathematical manipulations of the structure coordinates. For example, the structure coordinates set forth in Appendix I could be manipulated by crystallographic permutations of the structure coordinates, fractionalisation of the structure coordinates, integer additions or subtractions to sets of the structure coordinates, inversion of the structure coordinates, or any combination thereof.

Alternatively, modification in the crystal structure due to mutations, additions, substitutions, and/or deletions of amino acids, or other changes in any of the components that make up the crystal could also account for variations in structure coordinates.

Various computational analyses are used to determine whether a molecular complex or a portion thereof is sufficiently similar to all or parts of the structure of the extracellular domain of IR described above. Such analyses may be carried out in current software applications, such as the Molecular Similarity program of QUANTA (Molecular Simulations Inc., San Diego, Calif.) version 4.1.

The Molecular Similarity program permits comparisons between different structures, different conformations of the same structure, and different parts of the same structure.

Comparisons typically involve calculation of the optimum translations and rotations required such that the root mean square difference of the fit over the specified pairs of equivalent atoms is an absolute minimum. This number is given in angstroms.

Accordingly, structural coordinates of an IR ectodomain within the scope of the present invention include structural coordinates related to the atomic coordinates listed in Appendix I by whole body translations and/or rotations. Accordingly, RMSD values listed above assume that at least the backbone atoms of the structures are optimally superimposed which may require translation and/or rotation to achieve the required optimal fit from which to calculate the RMSD value.

A three dimensional structure of an IR ectodomain polypeptide or region thereof which substantially conforms to a specified set of atomic coordinates can be modelled by a suitable modeling computer program such as MODELER (Sall & Blundell, 1993), as implemented in the Insight II Homology software package (Insight II (97.0), MSI, San Diego), using information, for example, derived from the following data: (1) the amino acid sequence of the human IR ectodomain polypeptide; (2) the amino acid sequence of the related portion(s) of the protein represented by the specified set of atomic coordinates having a three dimensional configuration; and, (3) the atomic coordinates of the specified three dimensional configuration. A three dimensional structure of an IR ectodomain polypeptide which substantially conforms to a specified set of atomic coordinates can also be calculated by a method such as molecular replacement, which is described in detail below.

Structure coordinates/atomic coordinates are typically loaded onto a machine readable-medium for subsequent computational manipulation. Thus models and/or atomic coordinates are advantageously stored on machine-readable media, such as magnetic or optical media and random-access or read-only memory, including tapes, diskettes, hard disks, CD-ROMs and DVDs, flash memory cards or chips, servers and the internet. The machine is typically a computer.

The structure coordinates/atomic coordinates may be used in a computer to generate a representation, e.g. an image, of the three-dimensional structure of the IR ectodomain crystal which can be displayed by the computer and/or represented in an electronic file.

The structure coordinates/atomic coordinates and models derived therefrom may also be used for a variety of purposes such as drug discovery, biological reagent (binding protein) selection and X-ray crystallographic analysis of other protein crystals.

"Target Binding Sites" for Compounds which Interact with IR

The three-dimensional structure of IR ectodomain and/or LCL IR ectodomain provided by the present invention can be used to identify potential target binding sites on IR ectodomain (i.e. to identify those regions of IR ectodomain involved in and important to the binding of insulin and signal transduction) as well as in methods for identifying or designing compounds which interact with potential target binding sites of IR ectodomain, e.g. potential modulators of IR.

Preferred target binding sites are those governing specificity, i.e. those regions of IR ectodomain involved in the initial "low affinity" binding of insulin (i.e. the initial docking of insulin to IR) and those governing signal transduction, i.e. those regions of the IR ectodomain involved in the "high affinity" binding of insulin which leads to the initiation of IR autophosphorylation.

In one embodiment, the target binding site is a "low affinity" binding site, i.e. a region of IR ectodomain involved in insulin docking to the receptor. Preferred low affinity target binding sites comprise one or more regions from the following: the L1 domain, the CT peptide and the CR domain of IR ectodomain. With regards to the L1 domain, the target binding site preferably comprises portions of the molecular surface of the central β-sheet of L1 and portions of the molecular surface of the second LRR which contain Phe39 or the loop in the fourth LRR rung of L1, or preferably both. With regards the CR domain, the target binding site preferably comprises module 6 of the CR domain.

Alternatively, the low affinity target binding site may comprise one or more amino acids from one or more of the following amino acid sequences: (i) amino acids 1-156; (ii) amino acids 704-719; and (iii) amino acids 157-310.

With regards to amino acids 1-156, the target binding site preferably comprises at least one amino acid from the amino acid sequence 1-68, preferably 1-55, and more preferably amino acid sequence 27-55. The target binding site preferably comprises at least one amino acid selected from Arg14, Asn15, Gln34, Leu36, Leu37, Phe39, Pro43-Phe46, Phe64, Leu87, Phe88, Asn90 and Phe89, more preferably at least one amino acid selected from Arg14, Asn15, Gln34, Leu37, Phe39, Pro43-Phe46, Phe64, yet more preferably at least one amino acid selected from Phe39 and Pro43-Phe46, and most preferably at least Phe39.

With regards to amino acids 157-310, the target binding site preferably comprises at least one amino acid from the amino acid sequence 192-310, more preferably at least one amino acid from the sequence 227-303, yet more preferably least one amino acid selected from the sequence 259-284.

In another embodiment, the target binding site is a "high affinity" binding site, i.e. a region of the IR ectodomain involved in binding to insulin already bound to one IR monomer and leading to signal transduction. Preferred high affinity target binding sites comprise one or more regions from the FnIII-1 domain. In particular, high affinity target binding sites comprise one or more of the AB loop of FnIII-1, the CC' loop of FnIII-1 and the EF loop of FnIII-1.

Alternatively, the high affinity binding site may comprise one or more amino acids from one or more of the following amino acid sequences: (i) 472-594; (ii)475-489; (iii) 508-536, and (iv) 550-569.

With regards to amino acids 475-489, the target binding site preferably comprises at least one amino acid from the amino acid sequence 478-486, and more preferably from amino acid sequence 481-483.

With regards to amino acids 508-536, the target binding site preferably comprises at least one amino acid selected from 517-534 and more preferably at least one amino acid selected from 525-534.

With regards to amino acids 550-569, the target binding site preferably comprises at least one amino acid selected from 552-562 and more preferably at least one amino acid selected from 555-558.

In a preferred embodiment, van der Waals and/or hydrophobic interactions account for the major portion of the binding energy between a compound and a low affinity binding site of IR.

The findings resulting from the three-dimensional structure of IR ectodomain and/or LCL IR ectodomain provided by the present invention can also be used to identify or more clearly elucidate potential target binding sites on IGF-1R ectodomain (i.e. to identify those regions, or at least more accurately elucidate those regions, of IGF-1R ectodomain involved in and important to the binding of IGF and signal transduction) as well as in methods used for identifying or designing compounds which interact with potential target binding sites of IGF-1R ectodomain, e.g. potential modulators of IGF-1R.

Preferred target binding sites are those governing specificity, i.e. those regions of IGF-1R ectodomain involved in the initial "low affinity" binding of IGF (i.e. the initial docking of IGF to IGF-1R) and those governing signal transduction, i.e. those regions of the IGF-1R ectodomain involved in the "high affinity" binding of IGF which leads to signal transduction.

In one embodiment, the target binding site is a "low affinity" binding site, i.e. a region of IGF-1R ectodomain involved in IGF-I docking to the receptor. Preferred low affinity target binding sites comprise one or more regions from the following: the L1 domain, the CT peptide and/or the CR domain of IGF-1R ectodomain. With regards to the L1 domain, the target binding site preferably comprises the central β-sheet of L1 in general and the top left hand corner of the $2^{nd}$ repeat containing Ser35 or the loop in the fourth LRR rung of L1, or preferably both. With regards the CR domain, the target binding site preferably comprises module 6 of the CR domain.

Alternatively, the "low affinity" target binding site may comprise one or more amino acids from one or more of the following amino acid sequences: (i) amino acids 1-149; (ii) amino acids 691-706; and (iii) amino acids 150-298.

With regards to amino acids 1-149, the target binding site preferably comprises at least one amino acid from the amino acid sequence 1-62, preferably 1-49, and more preferably amino acid sequence 23-49. The target binding site preferably comprises at least one amino acid selected from Arg10, Asn11, Tyr28, His30, Leu32, Leu33, Ile34, Ser35, Glu38, Leu56, Phe58, Arg59, Tyr61, Trp79, Leu81, Phe82, Tyr83, Asn84, Tyr85, Phe90, Glu91, more preferably at least one amino acid selected from Leu33, His20, Leu32, Asn84, Glu38, Tyr61, Tyr28, Leu56, Arg59 Trp79 and Phe90, yet more preferably at least one amino acid selected from Leu33, His 30, Tyr28, Leu56, Arg59, Trp79 and Phe 90, and most preferably at least Phe 90.

With regards to amino acids 1-149, the target binding site preferably comprises at least one amino acid from the amino acid sequence 185-298, more preferably at least one amino acid from the sequence 220-294, yet more preferably least one amino acid selected from the sequence 252-273.

In another embodiment, the target binding site is a "high affinity" binding site, i.e. a region of the IGF-1R ectodomain involved in binding to IGF already bound to one IGF-1R monomer and leading to signal transduction. Preferred "high affinity" target binding sites comprise one or more regions of the FnIII-1 domain. In particular, "high affinity target" binding sites comprise one or more of the AB loop of FnIII-1, the CC' loop of FnIII-1 and the EF loop of FnIII-1.

Alternatively, the "high affinity" binding site may comprise one or more amino acids from one or more of the following amino acid sequences: (i) 462-580, (ii) 465-479, (iii) 498-526 and (iv) 526-543.

With regards to amino acids 465-479, the target binding site preferably comprises at least one amino acid from the amino acid sequence 468-478 and more preferably from amino acid sequence 471-473.

With regards to amino acids 498-526, the target binding site preferably comprises at least one amino acid selected from 507-524 and more preferably at least one amino acid selected from 515-524.

With regards to amino acids 526-543, the target binding site preferably comprises at least one amino acid selected from 527-537 and more preferably at least one amino acid selected from 530-533.

In a preferred embodiment, van der Waals and/or hydrophobic interactions account for the major portion of the binding energy between a compound and a low affinity binding site of IGF-1R.

Additional preferred binding sites in the case of both IR and IGF-1R, particularly for biological macromolecules such as proteins or aptamers, are those that are devoid of glycosylation or devoid of steric hindrance from glycan covalently attached to the polypeptide at sites in the spatial vicinity.

Compounds According to the Invention

Compounds of the present invention include both those designed or identified using a screening method of the invention and those which are capable of recognising and binding to a target binding site as defined above. Compounds capable of recognising and binding to a target binding site may be produced using a screening method based on use of the atomic coordinates corresponding to the 3D structure of IR ectodomain or LCL IR ectodomain, or alternatively may be identified by screening against a specific target molecule which is indicative of the capacity to bind to a target binding site. Such a specific target molecule may, for example, be a short polypeptide defining an epitope (e.g. corresponding to a loop structure identified above as a target binding site) or a mimetic, e.g. a peptidomimetic, mimicking a target binding site.

The candidate compounds and/or compounds identified or designed using a method of the present invention may be any suitable compound, synthetic or naturally occurring, preferably synthetic. In one embodiment, a synthetic compound selected or designed by the methods of the invention preferably has a molecular weight equal to or less than about 5000, 4000, 3000, 2000 or 1000 daltons. A compound of the present invention is preferably soluble under physiological conditions.

The compounds (ligands) may encompass numerous chemical classes, though typically they are organic molecules, preferably small organic compounds having a molecular weight of more than 50 and less than about 2,500 daltons, preferably less than 1500, more preferably less than 1000 and yet more preferably less than 500. Such ligands can comprise functional groups necessary for structural interaction with proteins, particularly hydrogen bonding, and typically include at least an amine, carbonyl, hydroxyl or carboxyl group, preferably at least two of the functional chemical groups. Ligands often comprise cyclical carbon or heterocyclic structures and/or aromatic or polyaromatic structures substituted with one or more of the above functional groups. Ligands can also comprise biomolecules including peptides, saccharides, fatty acids, steroids, purines, pyrimidines, derivatives, structural analogs, or combinations thereof.

Ligands may include, for example: (1) Peptides such as soluble peptides, including Ig-tailed fusion peptides and members of random peptide libraries (see, e.g., Lam et al., 1991; Houghten et al., 1991) and combinatorial chemistry-derived molecular libraries made of D-and/or L-configuration amino acids; (2) Phosphopeptides (e.g., members of random and partially degenerate, directed phosphopeptide libraries, see, e.g., Songyang et al., 1993); (3) Antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); (4) Nonimmunoglobulin binding proteins such as but not restricted to avimers, DARPins and lipocalins; (5) Nucleic acid-based aptamers; and (6) Small organic and inorganic molecules.

Ligands can be obtained from a wide variety of sources including libraries of synthetic or natural compounds. Synthetic compound libraries are commercially available from, for example, Maybridge Chemical Co. (Trevillet, Cornwall, UK), Comgenex (Princeton, N.J.), Brandon Associates (Merrimack, N.H.), and Microsource (New Milord, Conn.).

Natural compound libraries comprising bacterial, fungal, plant or animal extracts are available from, for example, Pan Laboratories (Bothell, Wash.). In addition, numerous means are available for random and directed synthesis of a wide variety of organic compounds and biomolecules, including expression of randomized oligonucleotides.

Alternatively, libraries of natural compounds in the form of bacterial, fungal, plant and animal extracts can be readily produced. Methods for the synthesis of molecular libraries are readily available (see, e.g., DeWitt et al., 1993; Erb et al., 1994; Zuckermann et al., 1994; Cho et al., 1993; Carell et al., 1994a; Carell et al., 1994b; and Gallop et al., 1994). In addition, natural or synthetic compound libraries and compounds can be readily modified through conventional chemical, physical and biochemical means (see, e.g., Blondelle et al., 1996), and may be used to produce combinatorial libraries. In another approach, previously identified pharmacological agents can be subjected to directed or random chemical modifications, such as acylation, alkylation, esterification, amidification, and the analogs can be screened for IR-modulating activity.

Numerous methods for producing combinatorial libraries are known in the art, including those involving biological libraries; spatially addressable parallel solid phase or solution phase libraries; synthetic library methods requiring deconvolution; the "one-bead one-compound" library method; and synthetic library methods using affinity chromatography selection. The biological library approach is limited to polypeptide or peptide libraries, while the other four approaches are applicable to polypeptide, peptide, nonpeptide oligomer, or small molecule libraries of compounds (Lam, 1997).

Compounds also include compounds that may be synthesized from leads generated by fragment-based drug design, wherein the binding of such chemical fragments is assessed by soaking or co-crystallizing such screen fragments into crystals provided by the invention and then subjecting these to an X-ray beam and obtaining diffraction data. Difference Fourier techniques are readily applied by those skilled in the art to determine the location within the IR ectodomain structure at which these fragments bind, and such fragments can then be assembled by synthetic chemistry into larger compounds with increased affinity for the receptor.

Interaction of Compounds with IR and/or IGF-1R

A compound may interact with a specified region of IR or IGF-1R ectodomain (e.g. a target binding site) by binding either directly or indirectly to that region. A compound which binds directly, binds to the specified region. A compound which binds indirectly, binds to a region in close proximity to or adjacent to the specified region with the result that it interferes with the ability of the specified region to bind to insulin, either antagonistically or agonistically. Such interference may be steric, electrostatic, or allosteric. For example, compounds which bind to FnIII-2 can potentially sterically interfere with the binding of insulin to FnIII-1 (i.e. the high affinity binding site of IR), thus interfering with signal transduction. Preferably, a compound interacts with a specified region of the IR or IGF-1R ectodomain by binding directly to the specified region. In the case of compounds that bind to specific target molecules, such compounds bind directly to the specific target molecule.

Binding can be either by covalent or non-covalent interactions, or both. Examples of non-covalent interactions include electrostatic interactions, van der Waals interactions, hydrophobic interactions and hydrophilic interactions.

When a compound interacts with IR or IGF-1R, it preferably "modulates" IR or IGF-1R, respectively. By "modulate" we mean that the compound changes an activity of IR or IGF-1R by at least 10%. Suitably, a compound modulates IR or IGF-1R by increasing or decreasing signal transduction via IR or IGF-1R, respectively. The phrase "decreases signal transduction" is intended to encompass partial or complete inhibition of signal transduction via IR or IGF-1R. The ability of a candidate compound to increase or decrease signal transduction via IR or IGF-1R can be assessed by any one of the IR or IGF-1R cell-based assays described herein.

Compounds may act as antagonists or agonists for insulin binding to IR or as antagonists or agonists for IGF binding to IGF-1R.

Compounds of the present invention preferably have an affinity for IR or IGF-1R sufficient to provide adequate binding for the intended purpose. Suitably, such compounds and compounds which bind to specific target molecules of IR or IGF-1R have an affinity ($K_d$) of from $10^{-5}$ to $10^{-15}$ M. For use as a therapeutic, the compound suitably has an affinity ($K_d$) of from $10^{-7}$ to $10^{-15}$ M, preferably from $10^{-8}$ to $10^{-12}$ M and more preferably from $10^{-10}$ to $10^{-12}$ M. Where a compound is to be used as a reagent in a competitive assay to identify other ligands, the compound suitably has an affinity ($K_d$) of from $10^{-5}$ to $10^{-12}$ M.

As will be evident to the skilled person, the crystal structures presented herein have enabled, for the first time, direct comparison of the regions controlling ligand specificity in the closely related IGF-1R and IR, and the identification of critical regions of IR involved in the initial binding of insulin and in the subsequent formation of the high affinity insulin-IR complex that leads to signal transduction.

In one preferred embodiment, a compound has a high specificity for IR and/or a specific target molecule of IR but not for IGF-1R, i.e. a compound selectively binds to IR or has enhanced selectivity for IR over IGF-1R. In this respect, a compound suitably has an affinity ($K_d$) for IR and/or a specific target molecule of IR of no more than $10^{-5}$ M, preferably no more than $10^{-7}$ M, and an affinity for IGF-1R of at least $10^{-5}$ M, preferably at least $10^{-3}$ M. Such compounds are desirable as, for example, IR agonists where there propensity to interact with IGF-1R and thus, for example, promote undesirable cell proliferation, is reduced.

In a preferred embodiment, the (IR or specific target molecule of IR)/IGF-1R binding affinity ratio for a compound is at least 10 and preferably at least 100.

In another preferred embodiment, a compound has a high specificity for IGF-1R and/or a specific target molecule of IGF-1R but not for IR, i.e. a compound selectively binds to IGF-1R or has enhanced selectivity for IGF-1R over IR. In this respect, a compound suitably has an affinity ($K_d$) for IGF-1R and/or a specific target molecule of IGF-1R of no more than $10^{-5}$ M, preferably no more than $10^{-7}$ M, and an affinity for IR of at least $10^{-5}$ M, preferably at least $10^{-3}$ M. Such compounds are desirable as, for example, IGF-1R agonists where there propensity to interact with IR and thus, for example, promote glucose uptake and metabolism, is reduced.

In a preferred embodiment, the (IGF-1R or specific target molecule of IGF-1R)/(IR) binding affinity ratio for a compound is at least 10 and preferably at least 100.

Design, Selection, Fitting and Assessment of Chemical Entities that Bind IR Ectodomain Using a variety of known modelling techniques, the crystal structure of the present invention can be used to produce a model for at least part of IR ectodomain.

As used herein, the term "modelling" includes the quantitative and qualitative analysis of molecular structure and/or function based on atomic structural information and interaction models. The term "modelling" includes conventional numeric-based molecular dynamic and energy minimisation models, interactive computer graphic models, modified molecular mechanics models, distance geometry and other structure-based constraint models.

Molecular modelling techniques can be applied to the atomic coordinates of the IR ectodomain or a region thereof to derive a range of 3D models and to investigate the structure of binding sites, such as the binding sites of monoclonal antibodies, nonimmunoglobulin binding proteins and inhibitory peptides.

These techniques may also be used to screen for or design small and large chemical entities which are capable of binding IR and modulating the ability of IR to interact with extracellular biological targets, such as insulin or members of the IGF receptor family e.g. which modulate the ability of IR to heterodimerise. The screen may employ a solid 3D screening system or a computational screening system.

Such modelling methods are to design or select chemical entities that possess stereochemical complementarity to particular regions of IR ectodomain. By "stereochemical complementarity" we mean that the compound or a portion thereof makes a sufficient number of energetically favourable contacts with the receptor as to have a net reduction of free energy on binding to the receptor.

Such stereochemical complementarity is characteristic of a molecule that matches intra-site surface residues lining the groove of the receptor site as enumerated by the coordinates set out in Appendix I and/or Appendix II, optionally also utilising the coodinates set out in Appendix III. By "match" we mean that the identified portions interact with the surface residues, for example, via hydrogen bonding or by non-covalent Van der Waals and Coulomb interactions (with surface or residue) which promote desolvation of the molecule within the site, in such a way that retention of the molecule at the binding site is favoured energetically.

It is preferred that the stereochemical complementarity is such that the compound has a $K_d$ for the receptor site of less than $10^{-4}$M, more preferably less than $10^{-5}$M and more preferably $10^{-6}$M. In a most preferred embodiment, the $K_d$ value is less than $10^{-8}$M and more preferably less than $10^{-9}$M.

Chemical entities which are complementary to the shape and electrostatics or chemistry of the receptor site characterised by amino acids positioned at atomic coordinates set out in Appendix I and/or Appendix II will be able to bind to the receptor, and when the binding is sufficiently strong, substantially prohibit the interaction of the IR ectodomain with biological target molecules such as insulin.

It will be appreciated that it is not necessary that the complementarity between chemical entities and the receptor site extend over all residues of the receptor site in order to inhibit binding of a molecule or complex that naturally interacts with IR ectodomain.

A number of methods may be used to identify chemical entities possessing stereochemical complementarity to a region of the extracellular domain of IR. For instance, the process may begin by visual inspection of potential binding sites, for example, the binding sites for anti-IR antibodies, on the computer screen based on the IR ectodomain, or region thereof, coordinates in Appendix I and/or Appendix II generated from the machine-readable storage medium. Alternatively, selected fragments or chemical entities may then be positioned in a variety of orientations, or docked, within an individual binding site of IR ectodomain, as defined supra. Modelling software that is well known and available in the art may be used (Guida, 1994). These include QUANTA and InsightII [Molecular Simulations, Inc., San Diego, Calif., a division of Pharmacopiea, Inc., Princeton, N.J., 1992], SYBYL [Molecular Modeling Software, Tripos Associates, Inc., St. Louis, Mo., 1992]. This modelling step may be followed by energy minimization with standard molecular mechanics force fields such as AMBER (Weiner et al., 1984), and CHARMM (Brooks et al., 1983). In addition, there are a number of more specialized computer programs to assist in the process of selecting the binding moieties of this invention.

Specialised computer programs may also assist in the process of selecting fragments or chemical entities. These include, inter alia:

1. GRID (Goodford, 1985). GRID is available from Oxford University, Oxford, UK.

2. MCSS (Miranker & Karplus, 1991). MCSS is available from Molecular Simulations, Burlington, Mass.

3. AUTODOCK (Goodsell & Olsen, 1990). AUTODOCK is available from Scripps Research Institute, La Jolla, Calif.

4. DOCK (Kuntz et al., 1982). DOCK is available from University of California, San Francisco, Calif.

Once suitable chemical entities or fragments have been selected, they can be assembled into a single compound. In one embodiment, assembly may proceed by visual inspection of the relationship of the fragments to each other on the three-dimensional image displayed on a computer screen in relation to the structure coordinates of IR ectodomain. This is followed by manual model building using software such as Quanta or Sybyl. Alternatively, fragments may be joined to additional atoms using standard chemical geometry.

The above-described evaluation process for chemical entities may be performed in a similar fashion for chemical compounds.

Useful programs to aid one of skilled in the art in connecting the individual chemical entities or fragments include:
1. CAVEAT (Bartlett et al., 1989). CAVEAT is available from the University of California, Berkeley, Calif.
2. 3D Database systems such as MACCS-3D (MDL Information Systems, San Leandro, Calif.). This area is reviewed in Martin (1992).
3. HOOK (available from Molecular Simulations, Burlington, Mass.).

Other molecular modeling techniques may also be employed in accordance with this invention, see, e.g., Cohen et al. (1990) and Navia & Murcko (1992).

There are two preferred approaches to designing a molecule, according to the present invention, that complement the stereochemistry of IR. The first approach is to in silico directly dock molecules from a three-dimensional structural database, to the receptor site, using mostly, but not exclusively, geometric criteria to assess the goodness-of-fit of a particular molecule to the site. In this approach, the number of internal degrees of freedom (and the corresponding local minima in the molecular conformation space) is reduced by considering only the geometric (hard-sphere) interactions of two rigid bodies, where one body (the active site) contains "pockets" or "grooves" that form binding sites for the second body (the complementing molecule).

This approach is illustrated by Kuntz et al. (1982) and Ewing et al. (2001), the contents of which are hereby incorporated by reference, whose algorithm for ligand design is implemented in a commercial software package, DOCK version 4.0, distributed by the Regents of the University of California and further described in a document, provided by the distributor, which is entitled "Overview of the DOCK program suite" the contents of which are hereby incorporated by reference. Pursuant to the Kuntz algorithm, the shape of the cavity represented by a site on the IR or IGF-1R is defined as a series of overlapping spheres of different radii. One or more extant databases of crystallographic data, such as the Cambridge Structural Database System maintained by Cambridge University (University Chemical Laboratory, Lensfield Road, Cambridge, U.K.), the Protein Data Bank maintained by the Research Collaboratory for Structural Bioinformatics (Rutgers University, N.J., U.S.A.), LeadQuest (Tripos Associates, Inc., St. Louis, Mo.), Available Chemicals Directory (Molecular Design Ltd., San Leandro, Calif.), and the NCl database (National Cancer Institute, U.S.A) is then searched for molecules which approximate the shape thus defined.

Molecules identified on the basis of geometric parameters, can then be modified to satisfy criteria associated with chemical complementarity, such as hydrogen bonding, ionic interactions and Van der Waals interactions. Different scoring functions can be employed to rank and select the best molecule from a database. See for example Bohm & Stahl (1999). The software package FlexX, marketed by Tripos Associates, Inc. (St. Louis, Mo.) is another program that can be used in this direct docking approach (see Rarey et al., 1996).

The second preferred approach entails an assessment of the interaction of respective chemical groups ("probes") with the active site at sample positions within and around the site, resulting in an array of energy values from which three-dimensional contour surfaces at selected energy levels can be generated. The chemical-probe approach to ligand design is described, for example, by Goodford, (1985), the contents of which are hereby incorporated by reference, and is implemented in several commercial software packages, such as GRID (product of Molecular Discovery Ltd., West Way House, Elms Parade, Oxford OX2 9LL, U.K.).

Pursuant to this approach, the chemical prerequisites for a site-complementing molecule are identified at the outset, by probing the active site with different chemical probes, e.g., water, a methyl group, an amine nitrogen, a carboxyloxygen, or a hydroxyl. Favoured sites for interaction between the active site and each probe are thus determined, and from the resulting three-dimensional pattern of such sites a putative complementary molecule can be generated. This may be done either by programs that can search three-dimensional databases to identify molecules incorporating desired pharmacophore patterns or by programs which use the favoured sites and probes as input to perform de novo design. Suitable programs for determining and designing pharmacophores include CATALYST (including HypoGen or HipHop) (Molecular Simulations, Inc), and CERIUS2, DISCO (Abbott Laboratories, Abbott Park, Ill.) and ChemDBS-3D (Chemical Design Ltd., Oxford, U.K.).

The pharmacophore can be used to screen in silico compound libraries/three-dimensional databases, using a program such as CATALYST (Molecular Simulations, Inc); MACCS-3D and ISIS/3D (Molecular Design Ltd., San Leandro, Calif.), ChemDBS-3D (Chemical Design Ltd., Oxford, U.K.), and Sybyl/3 DB Unity (Tripos Associates, Inc., St. Louis, Mo.).

Databases of chemical structures are available from a number of sources including Cambridge Crystallographic Data Centre (Cambridge, U.K.), Molecular Design, Ltd., (San Leandro, Calif.), Tripos Associates, Inc. (St. Louis, Mo.), Chemical Abstracts Service (Columbus, Ohio), the Available Chemical Directory (MDL Inc), the Derwent World Drug Index (WDI), BioByteMasterFile, the National Cancer Institute database (NCl), and the Maybridge catalogue.

De novo design programs include LUDI (Biosym Technologies Inc., San Diego, Calif.), Leapfrog (Tripos Associates, Inc.), Aladdin (Daylight Chemical Information Systems, Irvine, Calif.), and LigBuilder (Peking University, China).

Once an entity or compound has been designed or selected by the above methods, the efficiency with which that entity or compound may bind to IR can be tested and optimised by computational evaluation. For example, a compound that has been designed or selected to function as an IR binding compound must also preferably traverse a volume not overlapping that occupied by the binding site when it is bound to the native IR. An effective IR binding compound must preferably demonstrate a relatively small difference in energy between its bound and free states (i.e., a small deformation energy of binding). Thus, the most efficient IR binding compound should preferably be designed with a deformation energy of binding of not greater than about 10 kcal/mole, preferably, not greater than 7 kcal/mole. IR binding compounds may interact with IR in more than one conformation that are similar in overall binding energy. In those cases, the deformation energy of binding is taken to be the difference between the energy of the free compound and the average energy of the conformations observed when the compound binds to the protein.

A compound designed or selected as binding to IR may be further computationally optimised so that in its bound state it would preferably lack repulsive electrostatic interaction with the target protein.

Such non-complementary (e.g., electrostatic) interactions include repulsive charge-charge, dipole-dipole and charge-dipole interactions. Specifically, the sum of all electrostatic interactions between the compound and the protein when the compound is bound to IR, preferably make a neutral or favourable contribution to the enthalpy of binding.

Once an IR-binding compound has been optimally selected or designed, as described above, substitutions may then be made in some of its atoms or side groups to improve or modify its binding properties. Generally, initial substitutions are conservative, i.e., the replacement group will have approximately the same size, shape, hydrophobicity and charge as the original group. It should, of course, be understood that components known in the art to alter conformation should be avoided. Such substituted chemical compounds may then be analysed for efficiency of fit to IR by the same computer methods described in detail above.

Specific computer software is available in the art to evaluate compound deformation energy and electrostatic interaction. Examples of programs designed for such uses include: Gaussian 92, revision C (Frisch, Gaussian, Inc., Pittsburgh, Pa.); AMBER, version 4.0 (Kollman, University of California at San Francisco); QUANTA/CHARMM (Molecular Simulations, Inc., Burlington, Mass.); and Insight II/Discover (Biosysm Technologies Inc., San Diego, Calif.).

The screening/design methods may be implemented in hardware or software, or a combination of both. However, preferably, the methods are implemented in computer programs executing on programmable computers each comprising a processor, a data storage system (including volatile and non-volatile memory and/or storage elements), at least one input device, and at least one output device. Program code is applied to input data to perform the functions described above and generate output information. The output information is applied to one or more output devices, in known fashion. The computer may be, for example, a personal computer, microcomputer, or workstation of conventional design.

Each program is preferably implemented in a high level procedural or object-oriented programming language to communicate with a computer system. However, the programs can be implemented in assembly or machine language, if desired. In any case, the language may be compiled or interpreted language.

Each such computer program is preferably stored on a storage medium or device (e.g., ROM or magnetic diskette) readable by a general or special purpose programmable computer, for configuring and operating the computer when the storage media or device is read by the computer to perform the procedures described herein. The system may also be considered to be implemented as a computer-readable storage medium, configured with a computer program, where the storage medium so configured causes a computer to operate in a specific and predefined manner to perform the functions described herein.

Screening Assays and Confirmation of Binding and Biological Activity

Compounds selected or designed in accordance with the in silico methods of the invention may be subjected to further confirmation of binding to IR by cocrystallization of the compound with IR and structural determination, as described herein.

Compounds designed or selected according to the methods of the present invention are preferably assessed by a number of in vitro and in vivo assays of IR and/or IGF-1R function to confirm their ability to interact with and modulate IR and/or IGF-IR activity. For example, compounds may be tested for their ability to bind to IR and/or IGF-1R and/or for their ability to modulate e.g. disrupt, IR and/or IGF-1R signal transduction.

Libraries may be screened in solution by methods generally known in the art for determining whether ligands competitively bind at a common binding site. Such methods may include screening libraries in solution (e.g., Houghten, 1992), or on beads (Lam, 1991), chips (Fodor, 1993), bacteria or spores (U.S. Pat. No. 5,223,409: Lardner), plasmids (Cull et al., 1992), or on phage (Scott & Smith, 1990; Devlin, 1990; Cwirla et al., 1990; Felici, 1991; U.S. Pat. No. 5,223,409: Lardner).

Where the screening assay is a binding assay, IR or IGF-1R may be joined to a label, where the label can directly or indirectly provide a detectable signal. Various labels include radioisotopes, fluorescent molecules, chemiluminescent molecules, enzymes, specific binding molecules, particles, e.g., magnetic particles, and the like. Specific binding molecules include pairs, such as biotin and streptavidin, digoxin and antidigoxin, etc. For the specific binding members, the complementary member would normally be labeled with a molecule that provides for detection, in accordance with known procedures.

A variety of other reagents may be included in the screening assay. These include reagents like salts, neutral proteins, e.g., albumin, detergents, etc., which are used to facilitate optimal protein-protein binding and/or reduce non-specific or background interactions. Reagents that improve the efficiency of the assay, such as protease inhibitors, nuclease inhibitors, antimicrobial agents, etc., may be used. The components are added in any order that produces the requisite binding. Incubations are performed at any temperature that facilitates optimal activity, typically between 4 and 40° C.

Direct binding of compounds to IR or IGF-1R can also be done by Surface Plasmon Resonance (BIAcore) (reviewed in Morton & Myszka, 1998). Here the receptor is immobilized on a CM5 or other sensor chip by either direct chemical coupling using amine or thiol-disulphide exchange coupling (Nice & Catimel, 1999) or by capturing the receptor ectodomain as an Fc fusion protein to an appropriately derivatised sensor surface (Morten & Myszka, 1998). The potential binding molecule (called an analyte) is passed over the sensor surface at an appropriate flow rate and a range of concentrations. The classical method of analysis is to collect responses for a wide range of analyte concentrations. A range of concentrations provides sufficient information about the reaction, and by using a fitting algorithm such as CLAMP (see Morton & Myszka, 1998), rate constants can be determined (Morton & Myszka, 1998; Nice & Catimel, 1999). Normally, the ligand surface is regenerated at the end of each analyte binding cycle. Surface regeneration ensures that the same number of ligand binding sites is accessible to the analyte at the beginning of each cycle.

Incubation periods are selected for optimum activity, but may also be optimized to facilitate rapid high-throughput screening. Normally, between 0.1 and 1 hour will be sufficient. In general, a plurality of assay mixtures is run in parallel with different test agent concentrations to obtain a differential response to these concentrations. Typically, one of these concentrations serves as a negative control, i.e. at zero concentration or below the level of detection.

The basic format of an in vitro competitive receptor binding assay as the basis of a heterogeneous screen for small organic molecular replacements for insulin may be as follows: occupation of the active site of IR or IGF-1R is quantified by time-resolved fluorometric detection (TRFD) as described by Denley et al. (2004). R⁻IR-A, R⁻IR-B and P6 cells are used as sources of IR-A, IR-B and IGF-1R respectively. Cells are lysed with lysis buffer (20 mM HEPES, 150 mM NaCl, 1.5 mM $MgCl_2$, 10% (v/v) glycerol, 1% (v/v) Triton X-100, 1 mM EGTA pH 7.5) for 1 hour at 4° C. Lysates are centrifuged for 10 minutes at 3500 rpm and then 100 µl is added per well to a white Greiner Lumitrac 600 plate previously coated with anti-insulin receptor antibody 83-7 or anti-IGF-1R antibody 24-31. Neither capture antibody interferes with receptor binding by insulin, IGF-I or IGF-II. Approximately 100,000 fluorescent counts of europium-labelled insulin or europium-labelled IGF-I are added to each well along with various amounts of unlabelled competitor and incubated for 16 hours at 4° C. Wells are washed with 20 mM Tris, 150 mM NaCl, 0.05% (v/v) Tween 20 (TBST) and DELFIA enhancement solution (100 µl/well) is added. Time-resolved fluorescence is measured using 340 nm excitation and 612 nm emission filters with a BMG Lab Technologies Polarstar™ Fluorimeter or a Wallac Victor II (EG & G Wallac, Inc.).

Examples of other suitable assays which may be employed to assess the binding and biological activity of compounds to and on IR are well known in the art. For example, suitable assays may be found in PCT International Publication Number WO 03/027246. Examples of suitable assays include the following:

(i) Receptor autophosphorylation (as described by Denley et al. (2004). R⁻ IR-A, R⁻IR-B cells or P6 cells are plated in a Falcon 96 well flat bottom plate at $2.5 \times 10^4$ cells/well and grown overnight at 37° C., 5% $CO_2$. Cells are washed for 4 hours in serum-free medium before treating with one of either insulin, IGF-I or IGF-II in 100 µl DMEM with 1% BSA for 10 minutes at 37° C., 5% $CO_2$. Lysis buffer containing 2 mM $Na_3VO_4$ and 1 mg/ml NaF is added to cells and receptors from lysates are captured on 96 well plates precoated with antibody 83-7 or 24-31 and blocked with 1×TBST/0.5% BSA. After overnight incubation at 4° C., the plates are washed with 1×TBST. Phosphorylated receptor is detected with europium-labelled antiphosphotyrosine antibody PY20 (130 ng/well, room temperature, 2 hours). DELFIA enhancement solution (100 µl/well) is added and time resolved fluorescence detected as described above.

(ii) Glucose uptake using 2-deoxy-[U-14C] glucose (as described by Olefsky, 1978). Adipocytes between days 8-12 post-differentation in 24-well plates are washed twice in Krebs-Ringer Bicarbonate Buffer (25 mM Hepes, pH 7.4 containing 130 mM NaCl, 5 mM KCl, $KH_2PO_4$, 1.3 mM $MgSO_4.7H_2O$, 25 mM $NaHCO_3$ and 1.15 mM $CaCl_2$) supplemented with 1% (w/v) RIA-grade BSA and 2 mM sodium pyruvate. Adipocytes are equilibrated for 90 min at 37° C. prior to insulin addition, or for 30 min prior to agonist or antagonist addition. Insulin (Actrapid, Novogen) is added over a concentration range of 0.7 to 70 nM for 30 min at 37° C. Agonist or antagonist (0 to 500 µM) is added to adipocytes for 90 min followed by the addition of insulin in the case of antagonists. Uptake of 50 µM 2-deoxy glucose and 0.5 µCi 2-deoxy-[U-¹⁴C] glucose (NEN, PerkinElmer Life Sciences) per well is measured over the final 10 min of agonist stimulation by scintillation counting.

(iii) Glucose transporter GLUT4 translocation using plasma membrane lawns (as described by Robinson & James (1992) and Marsh et al. (1995)).

(iv) GLUT4 translocation using plasma membrane lawns (as described by Marsh et al., 1995). 3T3-L1 fibroblasts are grown on glass coverslips in 6-well plates and differentiated into adipocytes. After 8-12 days post-differentiation, adipocytes are serum-starved for 18 hrs in DMEM containing 0.5% FBS. Cells are washed twice in Krebs-Ringer Bicarbonate Buffer, pH 7.4 and equilibrated for 90 min at 37° C. prior to insulin (100 nM) addition, or for 30 min prior to compound (100 µM) addition. After treatments, adipocytes are washed in 0.5 mg/ml poly-L-lysine in PBS, shocked hypotonically by three washes in 1:3 (v/v) membrane buffer (30 mM Hepes, pH 7.2 containing 70 mM KCl, 5 mM $MgCl_2$, 3 mM EGTA and freshly added 1 mM DTT and 2 mM PMSF) on ice. The washed cells are then sonicated using a probe sonicator (Microson) at setting 0 in 1:1 (v/v) membrane buffer on ice, to generate a lawn of plasma membrane fragments that remain attached to the coverslip. The fragments are fixed in 2% (w/v) paraformaldehyde in membrane buffer for 20 min at 22° C. and the fixative quenched by 100 mM glycine in PBS. The plasma membrane fragments are then blocked in 1% (w/v) Blotto in membrane buffer for 60 min at 22° C. and immunolabelled with an in-house rabbit affinity purified anti-GLUT4 polyclonal antibody (clone R10, generated against a peptide encompassing the C-terminal 19 amino acids of GLUT4) and Alexa 488 goat anti-rabbit secondary antibody (Molecular Probes; 1:200). Coverslips are mounted onto slides using FluoroSave reagent (Calbiochem), and imaged using an OptiScan confocal laser scanning immunofluorescence microscope (Optiscan, VIC., Australia). Data are analysed using ImageJ (NIH) imaging software. At least six fields are examined within each experiment for each condition, and the confocal microscope gain settings over the period of experiments are maintained to minimise between-experiment variability.

Insulin agonist activity may be determined using an adipocyte assay. Insulin increases uptake of ³H glucose into adipocytes and its conversion into lipid. Incorporation of ³H into a lipid phase is determined by partitioning of lipid phase into a scintillant mixture, which excludes water-soluble ³H products. The effect of compounds on the incorporation of ³H glucose at a sub-maximal insulin dose is determined, and the results expressed as increase relative to full insulin response. The method is adapted from Moody et al., (1974). Mouse epididymal fat pads are dissected out, minced into digestion buffer (Krebs-Ringer 25 mM HEPES, 4% HSA, 1.1 mM glucose, 0.4 mg/ml Collagenase Type 1, pH 7.4), and digested for up to 1.5 hours at 36.5 C. After filtration, washing (Krebs-Ringer HEPES, 1% HSA) and resuspension in assay buffer (Krebs-Ringer HEPES, 1% HSA), free fat cells are pipetted into 96-well Picoplates containing test solution and approximately an $ED_{20}$ insulin.

The assay is started by addition of ³H glucose (e.g. ex. Amersham TRK 239), in a final concentration of 0.45 mM glucose. The assay is incubated for 2 hours at 36.5° C., in a Labshaker incubation tower, 400 rpm, then terminated by the addition of Permablend/Toluene scintillant (or equivalent), and the plates sealed before standing for at least 1 hour and detection in a Packard Top Counter or equivalent. A full insulin standard curve (8 dose) is run as control on each plate.

Data are presented graphically, as the effect of the compound on an (approximate) $ED_{20}$ insulin response, with data normalized to a full insulin response. The assay can also be run at basal or maximal insulin concentration.

To test the in vivo activity of a compound, an intravenous blood glucose test may be carried out on Wistar rats as follows. Male Mol:Wistar rats, weighing about 300 g, are divided into two groups. A 10 µl sample of blood is taken from the tail vein for determination of blood glucose concentration. The rats are then anaesthetized (e.g. with Hypnorm/Dormicum) at t=30 min and blood glucose measured again at t=−20 mM and at t=0 mM. After the t=0 sample is taken, the rats are injected into the tail vein with vehicle or test substance in an isotonic aqueous buffer at a concentration corresponding to a 1 ml/kg volume of injection. Blood glucose is measured at times 10, 20, 30, 40, 60, 80, 120 and 180 mM. The anaesthetic administration is repeated at 20 min intervals.

Additional assays to determine the effect of binding molecules on IGF-1R activity are as follows:

(i) Cell Viability Assay on HT29 cells with induction of Apoptosis: The ability of compounds to inhibit IGF-mediated rescue from apoptosis is measured using the colorectal cell line HT29 cells (ATCC: HTB 38) after induction with Na Butyrate. The HT29 cells are plated out onto white Fluoronunc 96 well plates (Nunc) at 12,000 cells/ml and incubated at 37° C., 5% $CO_2$ for 48 hours. Media is aspirated and 100 µl/well of serum free DMEM/F12 is added for 2 hours to serum starve cells. IGF (100 ul/well 0.05-50 nM dilutions) in the presence and the absence of inhibitory compound is added in 0.1% BSA solution (Sigma) in DMEM/F12 (Gibco) in triplicate. A final concentration of 5 mM Butyrate (Sigma) is added to each well. Plates are incubated at 37° C., 5% $CO_2$ for a further 48 hours. Plates are brought to room temperature and developed (as per instructions for CTG Assay (Promega)). Luminescence signal is measured on the Polarstar plate reader and data is evaluated using table curve to obtain the specific ED50.

(ii) Cell Migration Assay: The migration assays are performed in the modified 96-well Boyden chamber (Neuroprobe, Bethesda, Mass.). An 8 µM polycarbonate filter, which is pre-soaked in 25 µg/ml of collagen in 10 mM acetic acid overnight at 4° C., is placed so as to divide the chamber into an upper & lower compartment. Varying concentrations of the IGF-I analogues (25 µl of 0-100 nM) diluted in RPMI (Gibco) with 0.5% BSA (Sigma) tested for their migration inducing ability, are placed in the lower compartment in quadruplicates. The wells of the upper chamber are seeded with 50 µl/well of $2 \times 10^5$ SW480 (ATCC:CCL 228) pre-incubated for 30 mins/37° C. with 1.1 µl of 2 µM Calcein (Molecular Probes). Cells migrate for 8 hours at 37° C., 5% $CO_2$. Unmigrated cells are removed by wiping the filter. The filter is then analysed in the Polarstar for fluorescence at excitation wavelength of 485 nm and emission wavelength of 520 nm. Data is evaluated using table curve to obtain the specific ED50 value.

(iii) Mouse Xenograft studies for anti-IGF-1R antibodies: In vivo studies are performed in 56-week-old female athymic BALBc nude mice, homozygous for the nunu allele. Mice are maintained in autoclaved micro-isolator cages housed in a positive pressure containment rack (Thoren Caging Systems Inc., Hazelton, Pa., USA. To establish xenografts, mice are injected subcutaneously into the left inguinal mammary line with $3 \times 10^6$ or $5 \times 10^6$ cells in 100 µl of PBS. Tumour volume (TV) is calculated by the formula (length× $width^2$)/2 (Clarke et al., 2000), where length is the longest axis and width the measurement at right angles to length.

Initial biodistribution of potential binding molecules are ascertained by injecting 40 BALBc nude mice with established xenografts with radiolabelled $^{111}$In-or $^{125}$I-anti-IGFR antibody (3 µg, 10 µCi) intravenously via the tail vein (total volume=0.1 ml). At designated time points after injection of the radioconjugates (t=4 h, days 1, 2, 3, 5 and 7), groups of mice (n=35) are killed by Ethrane anaesthesia. Mice are then exsanguinated by cardiac puncture, and tumours and organs (liver, spleen, kidney, muscle, skin, bone (femur), lungs, heart, stomach, brain, small bowel, tail and colon) are resected immediately. All samples are counted in a dual gamma scintillation counter (Packard Instruments). Triplicate standards prepared from the injected material are counted at each time point with tissue and tumour samples enabling calculations to be corrected for the physical decay of the isotopes. The tissue distribution data are calculated as the mean±s.d. percent injected dose per gram tissue (% ID $g^{-1}$) for the candidate molecule per time point.

Pharmacokinetics for the candidate compounds are ascertained as follows: Serum obtained from mice bearing xenografts, following infusion of radiolabelled-binding molecule as described above, is aliquoted in duplicate and counted in a gamma scintillation counter (Packard Instruments, Melbourne, Australia). Triplicate standards prepared from the injected material are counted at each time point with serum samples to enable calculations to be corrected for the isotope physical decay. The results of the serum are expressed as % injected dose per liter (% ID $l^{-1}$). Pharmacokinetic calculations are performed on serum data using a curve fitting program (WinNonlin, Pharsight Co., Mountain View, Calif., USA). A two-compartment model is used to calculate serum pharmacokinetic parameters of AUC (area under the serum concentration curve extrapolated to infinite time), CL (total serum clearance), $T_{12\alpha}$ and $T_{12\beta}$ (half-lives of the initial and terminal phases of disposition) for $^{125}$I-and $^{111}$In-labelled molecule.

(iv) Therapeutic in vivo studies: Tumour cells ($3 \times 10^6$) in 100 µl of media are inoculated subcutaneously into both flanks of 46-week-old female nude mice (n=5 $group^{-1}$). Candidate molecule treatment commences day 7 post-tumour cell inoculations (mean±s.e. tumour volume-60×15 $mm^3$) and consists of six intraperitoneal injections over 2 weeks of appropriate amounts of the candidate molecule or vehicle control. Tumour volume in $mm^3$ is determined as described previously. Data is expressed as mean tumour volume for each treatment group. Differences in tumour size between control and test groups are tested for statistical significance (P<0.05) by t-test.

Molecular Replacement/Binding

The structure coordinates of an IR ectodomain or a region of an IR ectodomain, such as those set forth in Appendix I and/or Appendix II, can also be used for determining at least a portion of the three-dimensional structure of a molecular complex which contains at least some structural features similar to at least a portion of IR. In particular, structural information about another crystallised molecular complex may be obtained. This may be achieved by any of a number of well-known techniques, including molecular replacement.

Methods of molecular replacement are generally known by those of skill in the art (generally described in Brunger, 1997; Navaza & Saludjian, 1997; Tong & Rossmann, 1997; Bentley, 1997; Lattman, 1985; Rossmann, 1972).

Generally, X-ray diffraction data are collected from the crystal of a crystallised target structure. The X-ray diffraction data is transformed to calculate a Patterson function. The Patterson function of the crystallised target structure is compared with a Patterson function calculated from a known structure (referred to herein as a search structure). The Patterson function of the crystallised target structure is rotated on the search structure Patterson function to determine the correct orientation of the crystallised target structure in the crystal. The translation function is then calculated to determine the location of the target structure with respect to the crystal axes. Once the crystallised target structure has been correctly positioned in the unit cell, initial phases for the experimental data can be calculated. These phases are necessary for calculation of an electron density map from which structural differences can be observed and for refinement of the structure. Preferably, the structural features (e.g., amino acid sequence, conserved di-sulphide bonds, and beta-strands or beta-sheets) of the search molecule are related to the crystallised target structure.

The electron density map can, in turn, be subjected to any well-known model building and structure refinement techniques to provide a final, accurate structure of the unknown crystallised molecular complex (eg see Jones et al., 1991; Brunger et al., 1998).

Obtaining accurate values for the phases, by methods other than molecular replacement, is a time-consuming process that involves iterative cycles of approximations and refinements and greatly hinders the solution of crystal structures. However, when the crystal structure of a protein containing at least a homologous portion has been solved, the phases from the known structure provide a satisfactory estimate of the phases for the unknown structure.

By using molecular replacement, all or part of the structure coordinates of IR ectodomain provided herein (and set forth in Appendix I and/or Appendix II) can be used to determine the structure of a crystallised molecular complex whose structure is unknown more rapidly and efficiently than attempting to determine such information ab initio. This method is especially useful in determining the structure of IR mutants and homologues.

The structure of any portion of any crystallised molecular complex that is sufficiently homologous to any portion of the extracellular domain of IR can be solved by this method.

Such structure coordinates are also particularly useful to solve the structure of crystals of IR co-complexed with a variety of molecules, such as chemical entities. For example, this approach enables the determination of the optimal sites for the interaction between chemical entities, and the interaction of candidate IR agonists or antagonists.

All of the complexes referred to above may be studied using well-known X-ray diffraction techniques and may be refined versus 1.5-3.5 Å resolution X-ray data to an R value of about 0.25 or less using computer software, such as X-PLOR (Yale University, distributed by Molecular Simulations, Inc.; see Brünger, 1996). This information may thus be used to optimize known IR agonist/antagonists, such as anti-IR antibodies, and more importantly, to design new or improved IR agonists/antagonists.

Antibodies and Nonimmunoglobulin Binding Proteins.

The term "antibody" as used in this invention includes intact molecules as well as fragments thereof, such as Fab, F(ab')$_2$, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')2, the fragment of the antibody that can be obtained by treating whole antibody with the enzyme pepsin without subsequent reduction; F(ab)$_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, Antibodies: A Laboratory Manual, Cold Spring Harbor Laboratory, New York (1988), incorporated herein by reference).

Antibodies of the present invention may be produced, for example, by immunizing mice with IR fragments, preferably purified fragments. After determining that the mice are producing anti-IR antibodies, hybridomas may be prepared and antibody specificity assayed by ELISA or Flow Cytometry.

The IR fragment suitably comprises at least one target binding site as defined herein. Such a target binding site may define a linear or non-linear epitope. In the case of a non-linear epitope, it is desirable to impart appropriate secondary and/or tertiary structure on the epitope. This may be achieved by using larger fragments, for example, of sufficient length to enable secondary structure or entire domains to form. Alternatively, in raising antibodies of the invention, it may be desirable to use derivatives of the peptides or loop structures which are conformationally constrained.

Conformational constraint refers to the stability and preferred conformation of the three-dimensional shape assumed by a peptide. Conformational constraints include local constraints, involving restricting the conformational mobility of a single residue in a peptide; regional constraints, involving restricting the conformational mobility of a group of residues, which residues may form some secondary structural unit; and global constraints, involving the entire peptide structure. For example, amino acids adjacent to or flanking the IR loop structures identified herein may be included in the construct to maintain conformation of the peptide used to raise antibodies.

In addition, the active conformation of the peptide may be stabilized by a covalent modification, such as cyclization or by incorporation of gamma-lactam or other types of bridges. For example, side chains can be cyclized to the backbone so as create a L-gamma-lactam moiety on each side of the interaction site, see, generally, Hruby et al. (1992). Cyclization also can be achieved, for example, by formation of cystine bridges, coupling of amino and carboxy terminal groups of respective terminal amino acids, or coupling of the amino group of a Lys residue or a related homolog with a carboxy group of Asp, Glu or a related homolog. Coupling of the alpha-amino group of a polypeptide with the epsilon-amino group of a lysine residue, using iodoacetic anhydride, can be also undertaken (see Wood & Wetzel, 1992).

Further the conformation of the peptide analogues may be stabilised by including amino acids modified at the alpha carbon atom (eg. α-amino-150-butyric acid) (Burgess & Leach, 1973a; Burgess & Leach, 1973b) or amino acids which lead to modifications on the peptide nitrogen atom (eg. sarcosine or N-methylalanine) (O'Donohue et al., 1995).

Another approach (described in U.S. Pat. No. 5,891,418) is to include a metal-ion complexing backbone in the peptide structure. Typically, the preferred metal-peptide backbone is based on the requisite number of particular coordinating groups required by the coordination sphere of a given complexing metal ion. In general, most of the metal ions that may prove useful have a coordination number of four to six. The nature of the coordinating groups in the peptide chain includes nitrogen atoms with amine, amide, imidazole, or guanidino functionalities; sulfur atoms of thiols or disulfides; and oxygen atoms of hydroxy, phenolic, carbonyl, or carboxyl functionalities. In addition, the peptide chain or individual amino acids can be chemically altered to include a coordinating group, such as for example oxime, hydrazino, sulfhydryl, phosphate, cyano, pyridino, piperidino, or morpholino. The peptide construct can be either linear or cyclic, however a linear construct is typically preferred.

Mimetics, Including Peptidomimetics

The present invention also provides isolated molecules which mimic one or more regions of an IR ectodomain ("mimetics"), which mimetics are identified and/or designed based on the 3D structure of a region of an IR ectodomain defined by the atomic coordinates of Appendix I and/or Appendix II, or portion thereof.

The present invention also provides isolated molecules which mimic one or more regions of an IGF-1R ectodomain, which mimetics are identified and/or designed using structural data from the 3D structure of the IR ectodomain defined by the atomic coordinates of Appendix I and/or Appendix II, or portion thereof.

The present invention also provides isolated molecules which mimic one or more regions of both an IR ectodomain and an IGF-1R ectodomain, i.e. chimeric mimetics.

The mimetics may be conformationally constrained molecules or alternatively molecules which are not conformationally constrained such as, for example, non-constrained peptide sequences.

In a preferred embodiment, a molecule mimics a region of an IR and/or IGF-1R ectodomain which is involved in the binding of insulin and/or IGF-1R, respectively, i.e. it mimics a target binding site. Molecules which mimic a region of an IR and/or IGF-1R ectodomain involved in binding insulin and/or IGF can be used to screen for ligands which bind to IR and/or IGF-1R, as the case may be. In other words, they can act as specific target molecules. Additionally, such mimetics can be used to screen for ligands which selectively bind IR over IGF-1R or vice versa.

In a preferred embodiment, the mimetic mimics, at least in part, the high affinity binding site of IR for insulin or IGF-1R for IGF.

The term "conformationally constrained molecules" means conformationally constrained peptides and conformationally constrained peptide analogues and derivatives.

The term "analogues" refers to molecules having a chemically analogous structure to the naturally occurring alpha-amino acids present in IR and/or IGF-1R. Examples include molecules containing gem-diaminoalkyl groups or alklylmalonyl groups.

The term "derivatives" includes alpha amino acids wherein one or more side groups found in the naturally occurring alpha-amino acids present in IR and/or IGF-1R have been modified. Thus, for example the naturally-occurring amino acids present in IR and/or IGF-1R may be replaced with a variety of uncoded or modified amino acids such as the corresponding D-amino acid or N-methyl amino acid. Other modifications include substitution of hydroxyl, thiol, amino and carboxyl functional groups with chemically similar groups.

The present invention encompasses the use of conformationally constrained peptidomimetics of fragments of IR and/or IGF-1R ectodomain that mimic the target binding sites defined herein (such as amino acid residues defining the second LRR rung of L1 and the fourth LRR rung of L1, module 6 of the CR domain, the AB loop of FnIII-1, the CC' loop of FnIII-1 and the EF loop of FnIII-1), i.e. analogues and derivatives which mimic the activity of IR (or one or more regions of IR) and/or IGF-1R (or one or more regions of IGF-1R) involved in binding insulin or IGF, respectively, and are therefore capable of modulating IR and/or IGF-1R activity in vivo. These peptidomimetics are preferably substantially similar in three-dimensional shape to the peptide structures (for example, loop structures) as they exist in native IR and/or IGF-1R. Substantial similarity means that the geometric relationship of groups in the IR and/or IGF-1R peptide fragment is preserved such that the peptidomimetic will mimic the activity of IR and/or IGF-1R in vivo.

A "peptidomimetic" is a molecule that mimics the biological activity of a peptide but is no longer peptidic in chemical nature. By strict definition, a peptidomimetic is a molecule that no longer contains any peptide bonds (that is, amide bonds between amino acids). However, the term peptide mimetic is sometimes used to describe molecules that are no longer completely peptidic in nature, such as pseudo-peptides, semi-peptides and peptoids. Whether completely or partially non-peptide, peptidomimetics for use in the methods of the invention provide a spatial arrangement of reactive chemical moieties that closely resembles the three-dimensional arrangement of active groups in the peptide on which the peptidomimetic is based. As a result of this similar active-site geometry, the peptidomimetic has effects on biological systems which are similar to the biological activity of the peptide.

There are clear advantages for using a mimetic of a given peptide rather than the peptide itself, because peptides commonly exhibit two undesirable properties: (1) poor bioavailability; and (2) short duration of action. Peptide mimetics offer an obvious route around these two major obstacles, since the molecules concerned are small enough to be both orally active and have a long duration of action. There are also considerable cost savings and improved patient compliance associated with peptide mimetics, since they can be administered orally compared with parenteral administration for peptides. Furthermore, peptide mimetics are generally cheaper to produce than peptides.

Suitable peptidomimetics based on, for example, IR residues 27-55 or 259-284, can be developed using readily available techniques. Thus, for example, peptide bonds can be replaced by non-peptide bonds that allow the peptidomimetic to adopt a similar structure, and therefore biological activity, to the original peptide. Further modifications can also be made by replacing chemical groups of the amino acids with other chemical groups of similar structure. The development of peptidomimetics derived from IR peptides based on residues 27-55 or 259-284 can be aided by reference to the three dimensional structure of these residues as provided in Appendix I and/or Appendix II. This structural information can be used to search three-dimensional databases to identify molecules having a similar structure, using programs such as MACCS-3D and ISIS/3D (Molecular Design Ltd., San Leandro, Calif.), ChemDBS-3D (Chemical Design Ltd., Oxford, U.K.), and Sybyl/3 DB Unity (Tripos Associates, St. Louis, Mo.).

Those skilled in the art will recognize that the design of a peptidomimetic may require slight structural alteration or adjustment of a chemical structure designed or identified using the methods of the invention. In general, chemical compounds identified or designed using the methods of the invention can be synthesized chemically and then tested for ability to modulate IR and/or IGF-1R activity using any of the methods described herein. The methods of the invention are particularly useful because they can be used to greatly decrease the number potential mimetics which must be screened for their ability to modulate IR and/or IGF-1R activity.

The peptides or peptidomimetics of the present invention can be used in assays for screening for candidate compounds which bind to regions of IR and/or IGF-1R and potentially interfere with the binding of insulin to IR and/or signal transduction and/or the binding of IGF to IGF-1R and/or signal transduction. Peptides or peptidomimetics which mimic target binding sites are particularly useful as specific target molecules for identifying potentially useful ligands for IR and/or IGF-1R.

Standard solid-phase ELISA assay formats are particularly useful for identifying compounds that bind to the receptor. In accordance with this embodiment, the peptide or peptidomimetic of the invention is immobilized on a solid matrix, such as, for example an array of polymeric pins or a glass support. Conveniently, the immobilized peptide or peptidomimetic is a fusion polypeptide comprising Glutathione-S-transferase (GST; e.g. a CAP-ERK fusion), wherein the GST moiety facilitates immobilization of the protein to the solid phase support. This assay format can then be used to screen for candidate compounds that bind to the immobilised peptide or peptidomimetic and/or interefere with binding of a natural binding partner of IR to the immobilised peptide or peptidomimetic.

Uses of Compounds which Interact with IR or IGF-1R

Compounds/chemical entities designed or selected by the methods of the invention described above may be used to modulate IR activity in cells, i.e. activate or inhibit IR activity. They may also be used to modulate homodimerisation of IR.

Modulation of homodimerisation of IR may be achieved by direct binding of the chemical entity to a homodimerisation surface of IR and/or by an allosteric interaction elsewhere in the IR extracellular domain.

Given that aberrant IR activity is implicated in a range of disorders, the compounds described above may also be used to treat, ameliorate or prevent disorders characterised by abnormal IR signalling. Examples of such disorders include malignant conditions including tumours of the brain, head and neck, prostate, ovary, breast, cervix, lung, pancreas and colon; and melanoma, rhabdomyosarcoma, mesothelioma, squamous carcinomas of the skin and glioblastoma.

The compounds designed to interact or identified as interacting with the extracellular domain of IR, and in particular to interact with the target binding sites, are useful as agonists or antagonists against the action of insulin on IR. The compounds are useful as assay reagents for identifying other useful ligands by, for example, competition assays, as research tools for further analysis of IR (and IGF-1R for that matter) and as potential therapeutics in pharmaceutical compositions.

Compounds provided by this invention are also useful as lead compounds for identifying other more potent or selective compounds. The mimetic compounds of the present invention are also potentially useful as inhibitors of the action of insulin and in the design of assay kits directed at identifying compounds capable of binding to the low affinity and/or high affinity binding site for insulin on IR. In particular, it is envisaged that compounds of the present invention will prove particularly useful in selecting/designing ligands which are specific for IR or IGF-1R.

In one embodiment, one or more of the compounds can be provided as components in a kit for identifying other ligands (e.g., small, organic molecules) that bind to IR or IGF-1R. Such kits may also comprise IR or IGF-1R, or functional fragments thereof. The compound and receptor components of the kit may be labeled (e.g., by radioisotopes, fluorescent molecules, chemiluminescent molecules, enzymes or other labels), or may be unlabeled and labelling reagents may be provided. The kits may also contain peripheral reagents such as buffers, stabilizers, etc. Instructions for use can also be provided.

IR and IGF-1R agonists and antagonists, and in particular antagonists, provided by this invention are potentially useful as therapeutics. For example, compounds are potentially useful as treatments for cancers, including, but not limited to, breast, prostate, colorectal, and ovarian cancers. Human and breast cancers are responsible for over 40,000 deaths per year, as present treatments such as surgery, chemotherapy, radiation therapy, and immunotherapy show limited success. Recent reports have shown that a previously identified IGF-1R antagonist can suppress retinal neovascularization, which causes diabetic retinopathy (Smith et al., 1999). IGF-1R agonist compounds (i.e. existing IGF-1R compounds which have been modified employing methods of the present invention) are useful for development as treatments for neurological disorders, including stroke and diabetic neuropathy. Reports of several different groups implicate IGF-1R in the reduction of global brain ischemia, and support the use of IGF-I for the treatment of diabetic neuropathy (reviewed in Auer et al., 1998; Apfel, 1999).

The IGF-1R agonist peptides of the invention may be useful for enhancing the survival of cells and/or blocking apoptosis in cells.

Administration

Compounds of the invention, i.e. ligands of the invention or modulators of IR or IGF-1R identified or identifiable by the screening methods of the invention, may preferably be combined with various components to produce compositions of the invention. Preferably the compositions are combined with a pharmaceutically acceptable carrier or diluent to produce a pharmaceutical composition (which may be for human or animal use).

The formulation will depend upon the nature of the compound and the route of administration but typically they can be formulated for topical, parenteral, intramuscular, oral, intravenous, intra-peritoneal, intranasal inhalation, lung inhalation, intradermal or intra-articular administration. The compound may be used in an injectable form. It may therefore be mixed with any vehicle which is pharmaceutically acceptable for an injectable formulation, preferably for a direct injection at the site to be treated, although it may be administered systemically.

The pharmaceutically acceptable carrier or diluent may be, for example, sterile isotonic saline solutions, or other isotonic solutions such as phosphate-buffered saline. The compounds of the present invention may be admixed with any suitable binder(s), lubricant(s), suspending agent(s), coating agent(s), solubilising agent(s). It is also preferred to formulate the compound in an orally active form.

In general, a therapeutically effective daily oral or intravenous dose of the compounds of the invention, including compounds of the invention and their salts, is likely to range from 0.01 to 50 mg/kg body weight of the subject to be treated, preferably 0.1 to 20 mg/kg. The compounds of the invention and their salts may also be administered by intravenous infusion, at a dose which is likely to range from 0.001-10 mg/kg/hr.

Tablets or capsules of the compounds may be administered singly or two or more at a time, as appropriate. It is also possible to administer the compounds in sustained release formulations.

Typically, the physician will determine the actual dosage which will be most suitable for an individual patient and it will vary with the age, weight and response of the particular patient. The above dosages are exemplary of the average case. There can, of course, be individual instances where higher or lower dosage ranges are merited, and such are within the scope of this invention.

For some applications, preferably the compositions are administered orally in the form of tablets containing excipients such as starch or lactose, or in capsules or ovules either alone or in admixture with excipients, or in the form of elixirs, solutions or suspensions containing flavouring or colouring agents.

The compositions (as well as the compounds alone) can also be injected parenterally, for example intravenously, intramuscularly or subcutaneously. In this case, the compositions will comprise a suitable carrier or diluent.

For parenteral administration, the compositions are best used in the form of a sterile aqueous solution which may contain other substances, for example enough salts or monosaccharides to make the solution isotonic with blood.

For buccal or sublingual administration the compositions may be administered in the form of tablets or lozenges which can be formulated in a conventional manner.

For oral, parenteral, buccal and sublingual administration to subjects (such as patients), the daily dosage level of the compounds of the present invention and their pharmaceutically acceptable salts and solvates may typically be from 10 to 500 mg (in single or divided doses). Thus, and by way of example, tablets or capsules may contain from 5 to 100 mg of active compound for administration singly, or two or more at a time, as appropriate. As indicated above, the physician will determine the actual dosage which will be most suitable for an individual patient and it will vary with the age, weight and response of the particular patient.

The routes of administration and dosages described are intended only as a guide since a skilled practitioner will be able to determine readily the optimum route of administration and dosage for any particular patient depending on, for example, the age, weight and condition of the patient.

The present invention will now be described further with reference to the following examples, which are illustrative only and non-limiting. The examples refer to the figures:

EXAMPLES

Experimental Procedures

Crystallisation, Structure Solution and Refinement of IR485

Construction of the IR485 Expression Vector

The expression plasmid pEE14/IR485 was constructed by inserting the double-stranded deoxyribonucleic cassette (SEQ ID Nos: 12 & 13):

```
Bgl II                                                           Xba I
5' GATCTCCGACGATGACGATAAGGAACAAAAACTCATCTCAGAAGAGGATCTGAATTAGT.... 3'
3' ....AGGCTGCTACTGCTATTCCTTGTTTTTGAGTAGAGTCTTCTCCTACACTTAATCAGATC 5'
     I (S)(D  D  D  K)(E  Q  K  L  I  S  E  E  D  L  N)*
``` encoding Ile485, a single Ser to reconstruct the BglII site, a five residue enterokinase cleavage site, the 11 residue c-myc epitope tag (SEQ ID NO: 14) (McKern et al., 1997) and a stop codon into the larger Bgl II/Xba I fragment generated by digestion of the mammalian expression plasmid vector pEE14 (Bebbington & Hentschel, 1987) containing human insulin receptor cDNA. The Bgl II site of insulin receptor cDNA lies within codon 484 of the mature insulin receptor sequence.

Cell Culture and Transfection

Plasmid pEE14/IR485 was transfected into Lec8 mutant CHO cells (Stanley, 1989) obtained from the American Tissue Culture Collection (CRL:1737) using LipofectAMINE (Gibco-BRL). Cell lines were maintained after transfection in glutamine-free medium (Glasgow modification of Eagle's medium [GMEM], ICN Biomedicals, Australia) and 10% dialysed FCS (Sigma, Australia) containing 25 µM methionine sulphoximine (MSX; Sigma, Australia) as described (Bebbington & Hentschel, 1987).

Transfectants were screened for protein expression by a dot-blot procedure using the anti-c-myc monoclonal antibody (Mab) 9E10 (Evan et al., 1985) or the anti-IR Mab 83.7 (gift from Ken Siddle, University of Cambridge, UK) as primary antibodies and sheep anti-mouse Ig-horseradish peroxidase conjugate (Silenus Laboratories, Australia) as the secondary antibody. Immunoprecipitates, generated from positive clones by treatment of culture supernatants with a combination of Mab 83.7 and Protein A Sepharose CL-4B (Pharmacia Biotech, Sweden), were examined by sodium dodecyl sulfate polyacrylamide gel electrophoresis and autoradiography after overnight growth of cell cultures in medium supplemented with 35S-cysteine and 35S-methionine (Express; Dupont NEN, U.S.A.). These autoradiographs indicated the presence of a predominant radiolabelled product of approximately 70 kDa in culture supernatants from the positive clones initially identified by dot-blotting.

Protein Production and Purification

Large-scale cultivation of selected clones expressing IR485 (residues 1-485 of the insulin receptor as set forth in SEQ. ID. NO:1) was carried out in a Celligen Plus bioreactor (New Brunswick Scientific, USA) containing 70 g Fibra-Cel Disks (Sterilin, UK) as carriers in a 1.25 L working volume. Continuous perfusion culture using GMEM medium supplemented with non-essential amino acids, nucleosides, 25 µM MSX and 10% FCS was maintained for 1 to 2 weeks followed by the more enriched DMEM/F 12 without glutamine, with the same supplementation, for the next 4-5 weeks. Cell growth was poor during the initial stages of the fermentation when GMEM medium was employed, but improved substantially following the switch to DMEM/F12. Target protein productivity was essentially constant during the period from ~100 to 700 h of the 760 h fermentation, as measured by ELISA using monoclonal antibody (Mab) to c-Myc (Mab 9E10) as the capture antibody and biotinylated Mab 83-7 as the developing antibody.

Soluble IR485 (residues 1-485 of the insulin receptor as set forth in SEQ. ID. NO:1) protein was recovered from harvested fermentation medium by affinity chromatography on columns of Mab 9E10 coupled to agarose beads (Mini Leak; Kern En Tec, Denmark) as previously described (McKern et al., 1997). Briefly, harvested culture medium containing secreted target protein at pH 8.0 was pumped through a 50 ml Mab 9E10 antibody column at 4° C., washed with at least ten column volumes of Tris-buffered saline containing 0.02% sodium azide (TBSA) and the bound protein eluted with a solution of 0.2-0.4 mg/ml of the c-myc peptide EQKLISEEDLN (residues 8 through 18 of SEQ ID NO: 14) in TBSA. Residual bound protein was eluted with sodium citrate buffer at pH 3.0 into sufficient 1M Tris HCl buffer (pH 8.0) to neutralize the eluant.

Further purification was effected by gel filtration on Superdex 200 HR (Pharmacia, Sweden) in TBSA, monitored at 280 nm. A dominant peak was observed together with small quantities (estimated <10% total) of aggregated protein (not shown). The apparent molecular weight of the main peak was ~68 kDa (presumed to be monomer) when the concentration of eluted protein was ~25 ug/ml. At higher concentrations IR485 (residues 1-485 of the insulin receptor as set forth in SEQ. ID. NO:1) began to form dimers and gave a single peak of ~140 kDa when the concentration of eluted protein loaded was ~800 ug/ml. SDS-PAGE (Laemmli, 1970) using BioRad Protean II Minigels gave a single broad monomeric band under reduced and non-reduced conditions for both the monomer and dimer fractions (not shown). An estimated overall yield of 156 mg of purified receptor protein was obtained from 150 L of harvested medium following 9E10 Mab affinity chromatography and size-exclusion chromatography.

Isoelectric focussing focusing polyacrylamide gel electrophoresis was carried out using either Novex pH 3-7 or BioRad pH 5-8 isoelectric focussing focusing minigels. Isoforms of purified IR485/myc protein were loaded onto a Uno QP Uno™ Q Polishing (commercially available from Bio-Rad) anion exchange column connected to a BioLogic liquid chromatography system (BioRad). Protein was eluted in 40 mM Tris-HCl buffer at pH 8.0 using either shallow gradients or specific concentrations of KCl.

IR485 Crystallization Trials and Isoform Heterogeneity

Purified IR485 (residues 1-485 of the insulin receptor as set forth in SEQ. ID. NO:1) was shown, by isoelectric focussing, to consist of multiple bands (pI range 5.7-6.8), with the proportion of the more basic bands increasing on storage. Partial purification of the isoforms was achieved by shallow KCl elution of protein bound to two connected Uno QP columns (BioRad). N-terminal sequence analysis using a Hewlett Packard G1005A sequencer (Sparrow et al., 1997), SDS-PAGE mobilities and the ability to react with mAb 9E10 indicated that the more basic isoforms were generated by progressive proteolytic degradation at the C-terminus resulting in partial or complete removal of the acidic c-myc tag and enterokinase cleavage site.

For optimal crystallization trials, it was desirable to have a stable isoform of IR485 (residues 1-485 of the insulin receptor as set forth in SEQ. ID. NO:1). Enterokinase was inefficient at effecting cleavage at the engineered DDDDK (residues 3 through 7 of SEQ ID NO: 14) site immediately upstream of the c-myc epitope and left an undesirable acidic C-terminus of —SDDDD (residues 2 through 6 of SEQ ID NO: 14) after cleavage (not shown). An alternative partial proteolysis treatment method using endoproteinase Asp-N (Boehringer) was found to be effective for production of a stable, major isoform that could be isolated. At an enzyme:protein ratio (w/w) of 1:1000 at ambient temperature, four major bands of pI ~6.6-7.0 were produced after two minutes, the pattern remaining largely unchanged up to the 60 minute limit of this digestion experiment (not shown). The most basic isoform (pI ~7.0) was present in greatest amount and was sufficiently separated from other isoforms to allow substantial enrichment by ion-exchange chromatography. Following scale-up, AspN treatment at ambient temperature on 5 mg of protein at an enzyme:protein ratio of 1:2500 for 3 h, the diluted incubation mixture was loaded onto a Uno Q2 column and eluted isocratically at a concentration of KCl just sufficient to displace the basic isoform (not shown). This procedure yielded a fraction that was enriched in the most basic species, and contained a second isoform in lesser abundance (not shown). Treatment with endoproteinase Asp-N was expected to progressively cleave the X-D peptide bonds within the 17 residue unstructured affinity tag and cleavage site, SDDDDKEQKLISEEDLN (residues 2 through 18 of SEQ ID NO:14), resulting in a series of protein species truncated at the C-terminus.

IR485 Crystallization and Data Collection

Crystallization trials were performed with a factorial screen (Jancarik & Kim, 1991) using the hanging drop method. Initially, small rod-shaped crystals grew within 4-5 days, which diffracted to ~4 Å. Further crystallization trials using seeding, led to the production of large-sized crystals (0.7 mm×0.1 mm×0.1 mm) that diffracted to 3.3 Å in the laboratory and 2.3 Å at the synchrotron. The best crystallization conditions were 1.5-1.65 M (NH4)2SO4, 2% PEG 400, pH 8.5. Crystals were cryo-cooled to −170° C. in 20% PEG, 20% glycerol. Diffraction data to 3.31 Å resolution were initially recorded as 130 1°-exposures on a Rigaku RAXIS IV area detector using RU-300 Rigaku generator (Cu Kα radiation) equipped with ellipsoidal glass capillary optics (AXCO). Data were integrated and scaled using DENZO/SCALEPACK (Otwinowski & Minor 1997) giving mosaic spread 0.37°, Rsym=0.211, <I/sigmaI>=5.3, multiplicity 4.6, completeness 99.9%. A second set of diffraction data were recorded to 2.3 Å resolution using a Mar 345 detector at the Advanced Photon Source (APS) beamline 14-BM-D (wavelength 1.037 Å) and integrated in a similar manner, with 116 0.75°-exposures, mosaic spread 0.27°, Rsym=0.072, <I/sigmaI>=12.0, multiplicity 3.4, completeness 98%. The space group is P212121 with unit cell dimensions a=103.86 Å, b=130.24 Å, c=160.92 Å. From the apparent molecular mass of 68 kDa per monomer and two molecules per asymmetric unit, the solvent content is estimated as 69%.

IR485 Structure Solution and Refinement

The structure was solved by molecular replacement with AMORE using data (8-4 Å resolution) from the initial data set and the structure of IGF-1R 1-300 (L1-CR) and 301-459 (L2) as search models. For L1-CR, solutions corresponded to the two highest peaks from translation functions. Using these solutions, one solution was found for L2 and a second L2 domain was placed by inspection from electron density maps. Four rigid bodies were refined with XPLOR (Brunger, 1996), giving R=0.462 for data 10-4 Å resolution. Despite the low predicted protein content of the crystals (25%, VM=4.9), electron density was only observed for two molecules of IR485 (residues 1-485 of the insulin receptor as set forth in SEQ. ID. NO:1) per asymmetric unit. With data from the APS, structure refinement proceeded with rounds of manual refitting with O (Jones et al., 1991), alternated with energy minimization, B factor refinement and sometimes simulated annealing, using XPLOR, CNS (Brunger et al., 1998) and REFMAC (Murshudov et al., 1997). The resolution was extended in a stepwise manner and a bulk solvent correction and overall anisotropic thermal parameters were applied. The final model contains 931 amino acids, 40 carbohydrate residues 1 PEG 400 molecule and 262 solvent molecules, giving R=0.194, Rfree=0.235 (data 40-2.317Å). For residues 1-3 of both molecules and 270-273 from IR-2, the electron density is unclear and there is no density for residues beyond residues 468 in IR-1 or 469 in IR-2.

Calculation of Electrostatic Potential

The electrostatic potential was calculated and mapped on to the molecular surface of each of the structures IGF-1R and IR-1 using PARSE charges (Sitkoff et al., 1994) for each atom, and performed with the GRASP v. 1.6 program (Nicholls et al., 1991), which computes the electrostatic potentials in a continuum representation of the electrostatics by numerically solving the finite difference Poisson-Boltzmann equation.

Crystallisation, Structure Solution and Refinement of IRΔβ.
IRA Ectodomain Protein Production and Purification The IR-A ectodomain construct (SEQ ID NO:2) was generated as described previously (Tulloch et al., 1999) and converted to the IRΔβ construct (SEQ ID NO:15) by oligonucleotide-directed in vitro mutagenesis using the USBT7 Gen™ kit. In IRΔβ, residues 731-734 (VTVA) near the start of the β-chain are replaced with the less hydrophobic sequence AGNN and the nucleotides coding for the 19 residues from 735-753 (VPTVAAFPNTSSTSVPTSP) are removed. IRΔβ lacks the two N-linked glycosylation sites at 730 and 743, all six IR O-glycosylation sites at T732, T737, S745, S746, T747 and T751 (Sparrow, 2006) and residue 917 (K917), the last residue of the ectodomain before the transmembrane region, which was removed in constructing the termination codon.

For mammalian cell expression, the IRΔβ cDNA was inserted into the pEE 14 vector and the resulting plasmid used to transfect Lec8 mutant CHO cells as described previously (McKern et al, 1997). IRΔβ protein was produced in spinner flasks and purified by affinity chromatography and gel-filtration chromatography as described previously (Tulloch et al., 1999). Final purification was by ion-exchange chromatography on Resource Q (Pharmacia, Sweden) using shallow salt gradients (McKern et al, 1997), which enabled the separation into three fractions corresponding to well-defined peaks.

Fab fragments for the monoclonal antibodies 83-7 and 83-14 (Soos et al, 1986) were prepared as previously described (Tulloch et al., 1999).

Cloning of Monoclonal Antibody Variable Region cDNA.

cDNA corresponding to the heavy and light chain variable regions of the monoclonal antibodies 83-7 and 83-14 (Soos et al., 1986) was prepared as described previously (Gilliland et al, 1996) and cloned using the Zero Blunt TOPO PCR Cloning Kit (Invitrogen). A minimum of three individual clones for each variable region was sequenced to establish the translated amino acid sequence.

IR-A Ectodomain Crystallization.

The complex of IRΔβ from the first fraction of the ion exchange chromatography with Fab 83-7, Fab 83-14 and the S519-N20 peptide (Pillutla et al., 2002; Schaffer et al., 2003) was prepared at a molar ratio of 3:8:8:10 respectively in 0.15M NaCl-40 mM TrisHCl (pH 7.9), 0.02% sodium azide and 10% D-trehalose. After at least 4 hours at 4° C., the complex was passed over a Superdex 200 column to remove excess reagents, and concentrated to 3 mg/ml in 10 mM HEPES (pH 7.5). Initial crystallization conditions were found by vapour diffusion using an in-house screen of 808 conditions. Subsequent refinement of these conditions led to crystals being obtained via vapour diffusion protocols with (0.24 M ammonium tartrate and 15% PEG 3350 at either 4° C. or 20° C. A di-t-iodobis(ethylenediamine) diplatinum (II) nitrate (PIP) derivatized crystal was generated by soaking a crystal in a solution consisting of the well solution plus 2 mM PIP.

IR-A Ectodomain X-ray Data Collection

A native data set and a PIP derivative data set were collected at the IMCA-CAT 17-ID undulator beamline at the Advanced Photon Source (Argonne, USA), each from single crystals which diffracted to 4.5 Å and 5.5 Å respectively. A further native data set was collected from a single crystal up to 3.8 Å resolution at the BL5A wiggler beamline at the Photon Factory (Tsukuba, Japan). These beamlines are equipped respectively with ADSC Quantum 210 and 315 CCD detectors. Data processing was conducted with the HKL suite (Otwinowski & Minor, 1997) and with D*trek (Pflugrath, 1999). Details of collection and processing are presented in Table 3. The space group was identified as $C222_1$ with unit cell dimensions (a=123.0 Å, b=319.7 Å, c=204.9 Å).

IRA Ectodomain Phasing, Model Building and Refinement

The initial structure solution was by molecular replacement using PHASER (McCoy et al., 2005) to address native data set 1 (Table 3). This process succeeded to locate in turn Fab domains, the L1-CR domain and the L2 domain. The Fab search model was that of the Hy-HEL5 antibody (PDB entry 1BQL) set at 5° hinge angle increments, whilst those of the L1-CR and L2 domain were derived from the earlier structure of the L1-CR-L2 fragment (examples 1-4). These results suggested that the solvent content of the unit cell was likely high (about 75%), with the asymmetric unit containing only one IRAQ monomer and its attached pair of Fabs.

Phase improvement then followed using both RESOLVE (Terwilliger, 2000) and BUSTER-TNT (Blanc et al., 2004) with the resultant electron density map revealing the likely location of three fibronectin type-3 like domains. At this stage it was clear that the CDRs of one Fab were positioned so as to interact with the CR region, identifying the Fab as 83-7, whilst the other was positioned to interact with one of the fibronectin domains, identifying it as 83-14 and the fibronectin domain as FnIII-1 [see Adams et al., 2000]. No electron density was visible for the insert domain nor for the constant domain of Fab 83-14.

At this stage, the second set of native data became available. The molecular replacement solution was verified afresh using a combination of single isomorphous replacement phases derived from the PIP-derivative data set (Table 3) processed with SHARP (Bricogne, 1997; de la Fortelle & Bricogne, 1997) and subsequent solvent-flattening using DM (Cowtan, 1994) and SOLOMON. Models of the FnIII domains were then built directly into the density using known FnIII domains 7, 8 and 9 of the fibronectin structure (PDB code 1FNF) to guide the building. Crystallographic refinement followed using iterative cycles of BUSTER-TNT (Blanc et al., 2004) and/or REFMAC5 manual model building using XtalView/Xfit (McRee, 1999) and/or O (Jones et al., 1991). Within BUSTER-TNT scattering from the missing atoms was modelled with a low resolution homographic exponential distribution and maximum entropy density completion was used at the end of each round of refinement to recover the density for missing parts of the structure.

During this process the sequences of Fabs 83-7 and 83-14 became available and were included in the model building. The loop (518-529) region of FnIII-1 was modelled with the C524-0524 disulphide bond included between 2-fold related α chains of homodimer. There was no convincing density for residues 656 to 754 from the insert domain. Significant continuous and extended electron density lay across the ligand binding face of L1 and was initially interpreted to be the S519N20 peptide. However, crystallographic data derived subsequently derived from crystals grown (under similar conditions to that described above) of the same Fab-complexed IRΔβ ectodomain construct but without the inclusion of the S519N20 peptide in the complex revealed a similar segment of electron density extending across the binding face of the L1. With out being bound, it is believed that this segment of electron density correspondes to a part of the insert domain ID, and most likely to the CT peptide or residues immediately upstream of this segment (Kristensen et al., 1998, 1999). Concomitantly, there appears to be no electron density present that can be associated definitively with the S519N20 peptide. It appears that this peptide did not bind to the Fab-complex IRΔβ receptor ectodomain. Electron density consistent with N-linked glycan was detected at 10 of the 16 potential N-linked sites within the modelled fragment but no sugar residues were built at these sites at this stage. The final model comprises 439 residues from Fab 83-7, 429 residues from Fab 83-14 and residues 4 to 655 and 755 to 909 of IRΔβ. Final refinement statistics are shown in Table 3.

Isolation and Chemical Characterisation of the N-linked Glycans of Human IR and Their Incorporation into the 3D Crystal Structure of IRΔβ.

Materials

Human IR ectodomain was expressed in CHO-K1 cells and in Lec8 cells and purified as previously described (Sparrow et al., 1997; Tulloch et al., 1999). PNGase F was obtained from New England Biolabs; O-Glycosidase (BSA-Free) and pepsin were from Boehringer Mannheim; *Staphylococcus aureus* V8 protease was from ICN; Streptococcal neuraminidase was obtained from Genzyme. The sources of all other reagents are listed in (Sparrow et al., 1997).

Protein Digestions and Peptide Purification

Digestions with pepsin were carried out in 1% (v/v) formic acid at 37° C. for 18 h and the reactions stopped by freezing. The conditions for other protease digestions were as follows: trypsin and endoproteinase Lys-C, 0.1 M Tris-HCl buffer, pH 8.5 at 37° C. for 16-18 h using an enzyme to substrate ratio of approximately 1:20; endoproteinase Asp-N, 50 mM sodium phosphate buffer, pH 8.0 at 37° C. for 16-18 h with an enzyme to substrate ratio of approximately 1:3; *S. aureus* V8 protease, 0.1 M ammonium bicarbonate, pH 8.2 at 37° C. for various times using an enzyme to substrate ratio of approximately 1:10. These protease digestions were stopped by acidification with 10% (v/v) trifluoracetic acid and fractionated by RP-HPLC. The methods used for all other protein cleavages are described in (Sparrow et al., 1997). Peptides were separated by RP-HPLC and identified by N-terminal amino acid sequence analysis. The presence of N-or O-linked carbohydrate was indicated by a blank cycle during sequencing instead of the expected PTH-asparagine or serine/threonine respectively. Glycopeptides were characterised by mass spectrometry thus allowing the glycan mass to be calculated and then used to assign the carbohydrate composition. O-Glycosidase digestions were carried out in 0.1 M sodium acetate, pH 6.0, at 37° C. for 16-18 h using 2.5 mU of enzyme, following a preliminary treatment for 4 h at 37° C. with neuraminidase (50 mU).

Reduction and Carboxymethylation

Peptides or peptide mixtures were reduced with 10 mM DTT for 2 h at 37° C. under argon in 6 M guanidine hydrochloride, 0.1 M Tris, 1 mM EDTA, pH 9.0; the mixture was then made 25 mM in iodoacetate and incubated for a further 30 min. Alkylation was stopped by the addition of excess DTT and the reduced, carboxymethylated peptides isolated by RP-HPLC.

Oligosaccharide Characterization Using 1-phenyl-3-methyl-5-pyrazolone (PMP) Derivatization The glycopeptides derived from the N-terminal tryptic peptide of CN11 (see Tables 3 and 4) contained both N-and O-linked glycans. The N-linked glycans from these peptides (sites 742 and 755) were investigated by derivatization with PMP following liberation with PNGase F; the resulting PMP derivatives were characterised by Matrix-assisted laser desorption/ionization time-of-flight mass spectrometry (MALDI-TOF MS) (Pitt and Gorman, 1997). Glycan masses were obtained by subtraction of 349 (the mass of the derivatising reagent) from the mass of the corresponding PMP derivative.

Other Techniques

The methods used for chromatography, polyacrylamide gel electrophoresis and protein analysis are described in (Sparrow et al., 1997). The buffers employed for RP-HPLC linear gradients were buffer A, ~0.1% (v/v) trifluoroacetic acid; buffer B, 0.1% (v/v) trifluoroacetic acid in 70% (v/v) acetonitrile. MALDI-TOF MS was performed with a Bruker Reflex mass spectrometer (Bruker-Franzen Analytik, Bremen) as described in (Sparrow et al., 1997; Pitt & Gorman, 1996; Pitt & Gorman 1997). From the masses obtained for each glycopeptide, the corresponding glycan masses were determined by subtraction of the peptide moiety. This allowed the calculation of the saccharide composition of each glycan in terms of the numbers of sialic acid, hexose, N-acetylhexosamine and deoxyhexose moieties present. Based on the known structures of N-linked glycans found on proteins expressed in CHO cells (see Spellman et al., 1989) these monosaccharides were assumed to be sialic acid, mannose, galactose, N-acetylglucosamine and fucose.

Molecular Modelling

The crystallographic electron density maps derived from the atomic model of the IR ectodomain (Appendix I) exhibits difference electron density consistent with the fourteen N-linked glycan at sites Asn16, Asn25, Asn111, Asn215, Asn255, Asn295, Asn337, Asn395, Asn418, Asn514, Asn606, Asn624, Asn881 and Asn894 (IR-A numbering).

The difference electron density discernible at the 1.0 σ level at each site was typically restricted to that associated with the first GlcNac residue of the glycan, with more diffuse and broken density extending outwards along the glycan stalk and into the volume occupied by the glycan antennae. Initial model structures for each N-linked glycan were built using the GLYPROT server (Bohne-Lang & von der Leith, 2005; Lütteke et al., 2006), followed by adjustment of the glycosidic torsion angles within the glycan so as to position the individual sugar residues as best as possible into available difference electron density. The atomic modelling of these glycans employed maps derived from preliminary phasing of data from a slightly better quality crystal of the receptor/Fab complex than that described above, the more detailed refinement of which is still in progress. In each instance, the model employed the most prevalent glycoform at each site based on the glycan composition data given in Table 5, except in the case of (i) the glycan at Asn881 (IR-A numbering), which was modelled as a complex carbohydrate, compatible with better mass spectroscopic data obtained from the same analysis of Lec8 derived protein, and (ii) the glycan at Asn894 (IR-A numbering), which was modelled as a complex carbohydrate in the absence of any data from the peptide digest. During this process reasonable stereochemistry, assessed using the CARP server (Lütteke et al., 2005), was maintained. This process was inevitably crude, given the low resolution of the diffraction data, the likely presence of more than one glycoform at each site and the torsional flexibility of the glycans themselves. Nevertheless, the stalks of the modelled glycan isoforms were directed away from the protein surface in a way that was compatible with the difference density, and that the antennae components of the model arguably lay within volume spanned by the disordered glycan species. In some instances small adjustment of the protein backbone conformation in the vicinity of the asparagine residue was needed to overcome the steric hindrance. All interactive graphics was conducted with O (Jones et al., 1991). As such these coordinates allow one to discern regions of the protein surface that should be excluded from consideration as target surface during the design of biologicals that target IR. These coordinates are listed in Appendix IV.

Examples 1-4 analyse the IR485 (residues 1-485 of the insulin receptor as set forth in SEQ. ID. NO:1) crystal structure, compare the structure with the corresponding structure for IGF-1R and analyse the interaction of insulin with the L1 domain. Examples 5-11 analyse the IRΔβ crystal structure, compare the structure with previously predicted structures, analyse the implications for signal transduction in the IR and analyse the distribution of the N-linked glycans over the surface of IR and by analogy the closely related IGF-1R and the impact of these oligosaccharide moieties on the accessibility of various regions of the insulin and IGF-1 receptors to binding macromolecules such as monoclonal antibodies and their fragments, nonimmunoglobulin binding proteins and nucleic acid aptamers.

Example 1

IR485 Structure

Figure 2:
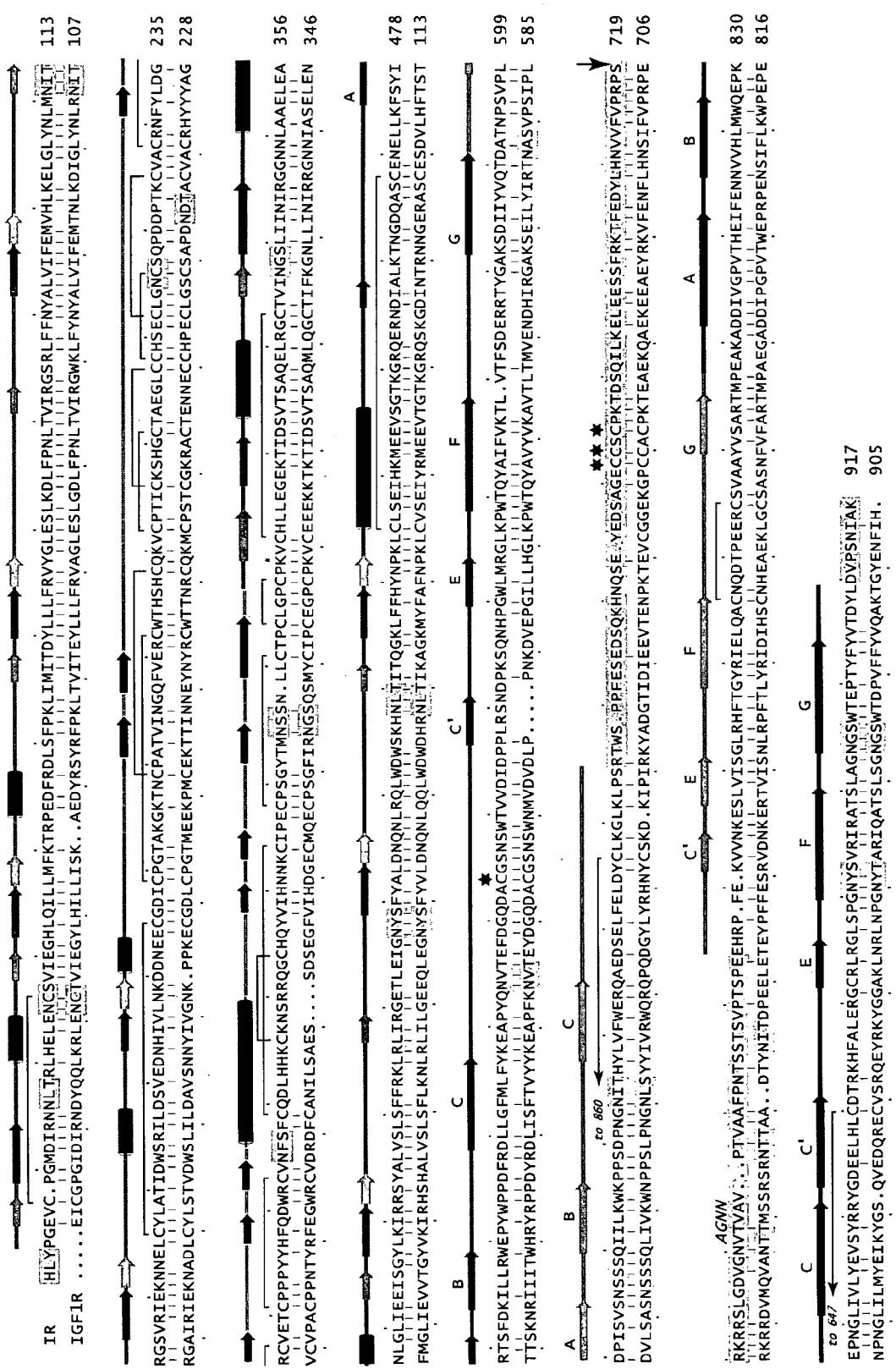
FIG. 2: Shows the sequence alignment of the ectodomains of human insulin receptor (IR, exon 11-isoform) (SEQ ID NO: 2) and human IGF1 receptor (IGF-1R) (SEQ ID NO: 3). Residues conserved between the sequences are indicated by vertical bars and potential N-linked glycosylation sites are indicated by shading. The location of secondary structure elements of the L1, CR and L2 domains of IR are indicated above the alignment. The approximate location of secondary structure elements within the FnIII domains of the IR structure are indicated and labelled according to the canonical strand nomenclature for such domains. Disulphide links are indicated by square braces above the alignment. The sites of glycosylation as well as the residues that are absent from the model, either because they were not included in the construct or because they were not discerned in the 25 crystallographic electron density maps, are shaded. Sequence sources were: IR (Ullrich et al., 1985), human type 1 IGF receptor (Ullrich et al., 1986).
Figure 3:
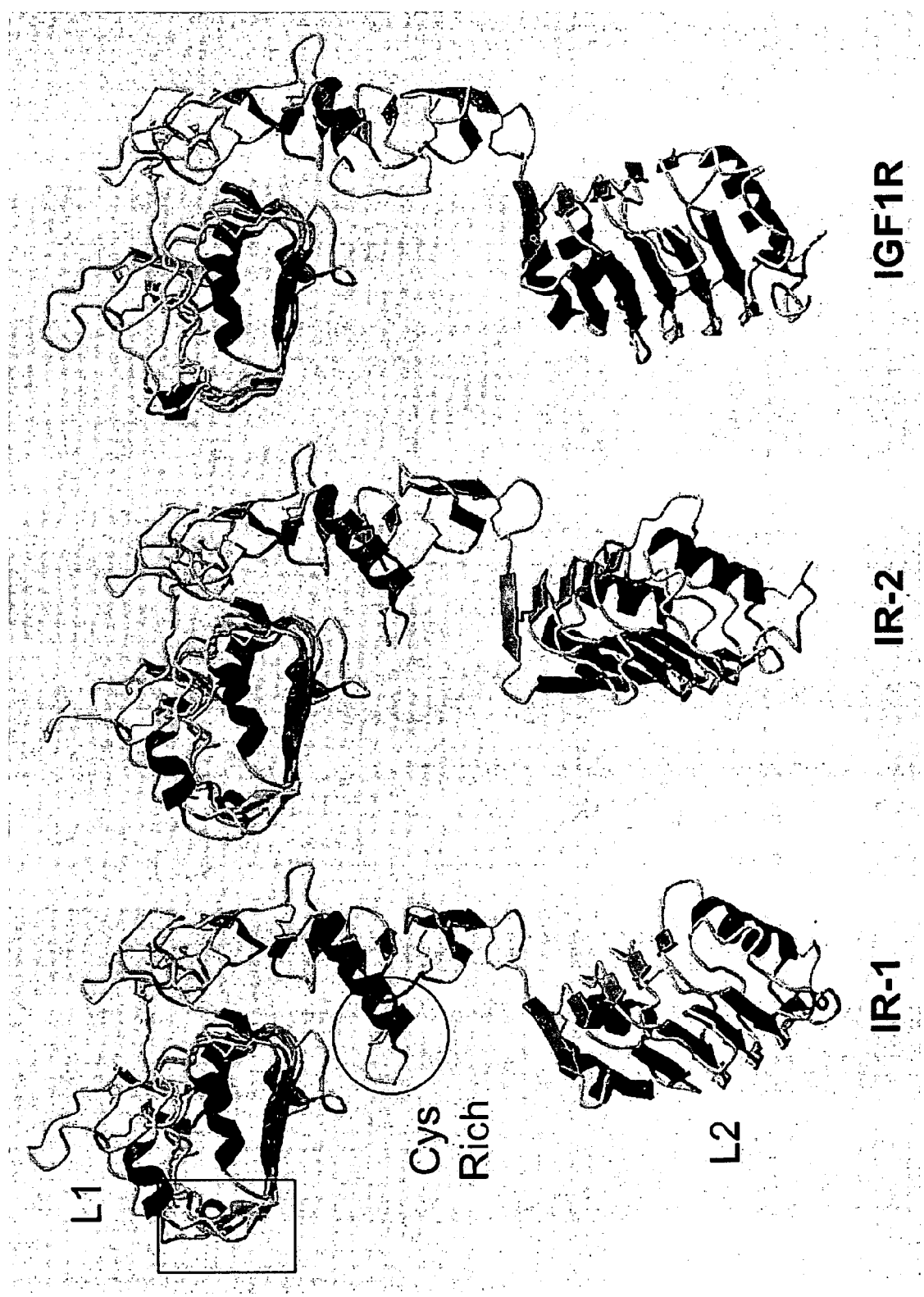
FIG. 3: Comparison of the structures of the L1-CR-L2 domain fragments of IR-1 (FIG. 3a), IR-2 (FIG. 3b) and IGF-1R (FIG. 3c). The L1 domains are depicted in the same orientation. Helices are indicated by curled ribbons and β-strands by broad arrows. The side-chains of disulfide-linked cysteine residues are depicted as sticks. The structure source for the L1-CR-L2 domains of IGF-1R is Protein Data Bank entry 1IGF (Garrett et al., 1998).

The truncated IR485 (residues 1-485 of the insulin receptor as set forth in SEQ. ID. NO:1) comprises the L1, CR and L2 domains (residues 1-469) plus the next 16 residues that include part of the first Fn III module. This fragment was previously shown to be stably expressed in mammalian cells (Schaefer et al., 1990). Unlike IGF-1R462, the IR485 (residues 1-485 of the insulin receptor as set forth in SEQ. ID. NO:1) crystals contain two receptor molecules in the unit cell, whose structures are very similar to each other but not identical. The comparative structures are shown in FIG. 3 and the amino acid sequences and secondary structural assignments in FIG. 2. Residues 470-485 at the C-terminus of the fragment, immediately after the end of the L2 domain, are disordered in both copies of IR485 (residues 1-485 of the insulin receptor as set forth in SEQ. ID. NO:1) in the crystal. As shown in FIG. 3 the IR fragment adopts an extended bilobal structure (40 Å×49 Å×110 Å) very similar to that seen for the corresponding IGF-1R462 fragment. Carbohydrate was detected at 8 of the 10 potential N-linked sites in the L1/CR/L2 fragment: at residues 16, 25 and 111 but not 78 in the L1 domain, 215 and 255 but not 295 in CR, and 337, 397 and 418 in the L2 domain. For the two sites with no visible carbohydrate attached, chemical analyses have shown that Asn78 is not glycosylated while Asn295 was shown to carry a complex, tetra-antennary glycan moiety (see Example 7).

The most notable differences in the overall structure are the relative orientations of the L2 domains, which are rotated 17° (molecule 1) and 32° (molecule 2) relative to IGF-1R462 (FIG. 3). While crystal packing is responsible for the relative orientations observed here, the structures do reveal that the L2 domain is capable of global movement with respect to the L1/CR domains as previously suggested (Garrett et al., 1998).

Example 2

IR and IGF-1R Domain Comparisons

Figure 4:
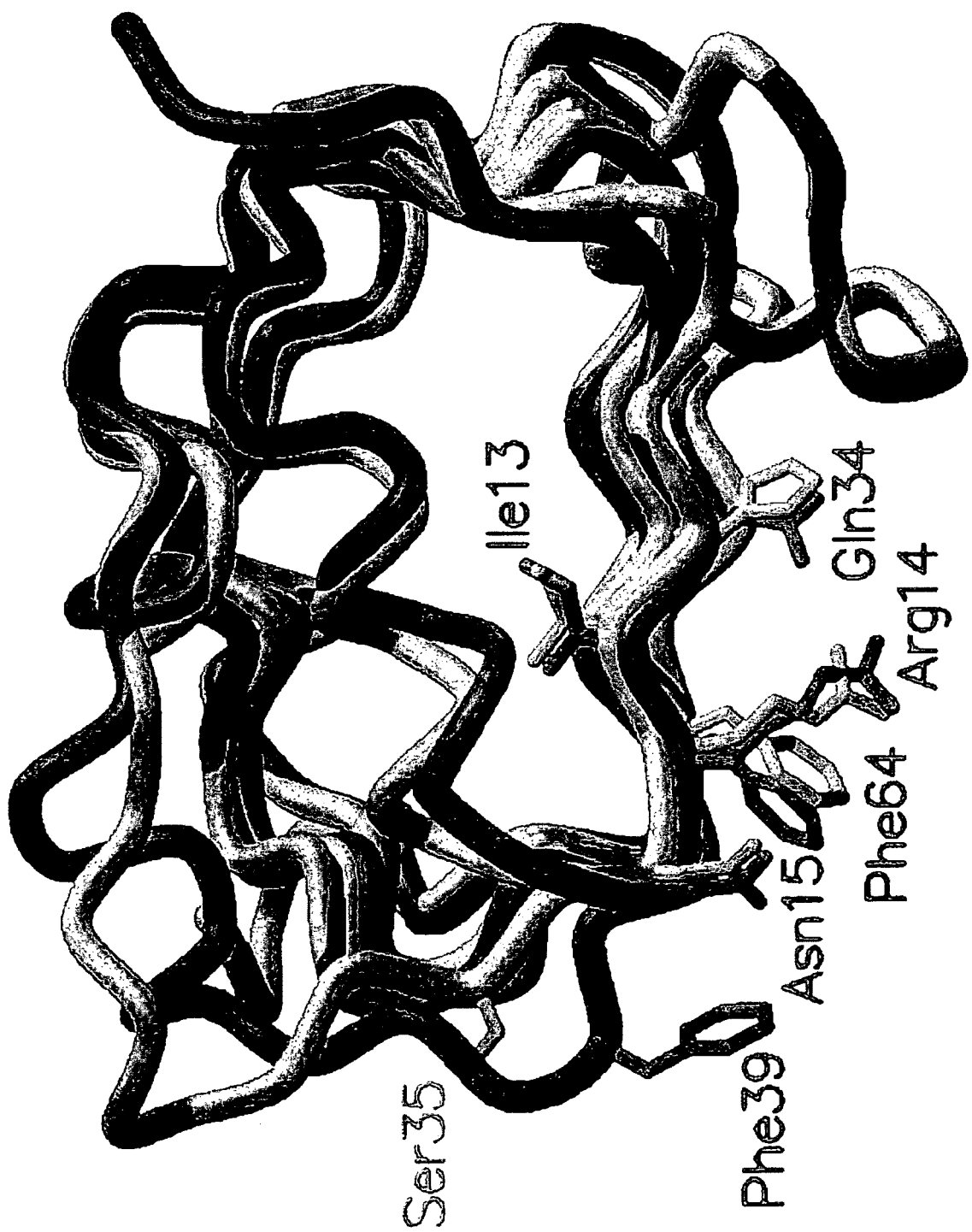
FIG. 4: Comparison of main chain traces for the L1 domains of IR (dark grey) and IGF-1R (light grey). Cα atoms from L1 domains have been superposed showing the major differences in the second half of the second leucine rich repeat of the L1 domain (left hand side). The side chains of key IR residues involved in insulin binding (Ile13, Arg14, Asn15, Gln34, Phe39 and Phe64) are depicted as sticks as is the side chain of IGF-1R residue Ser35, the homologue residue of Phe39 in IR.
Figure 5:
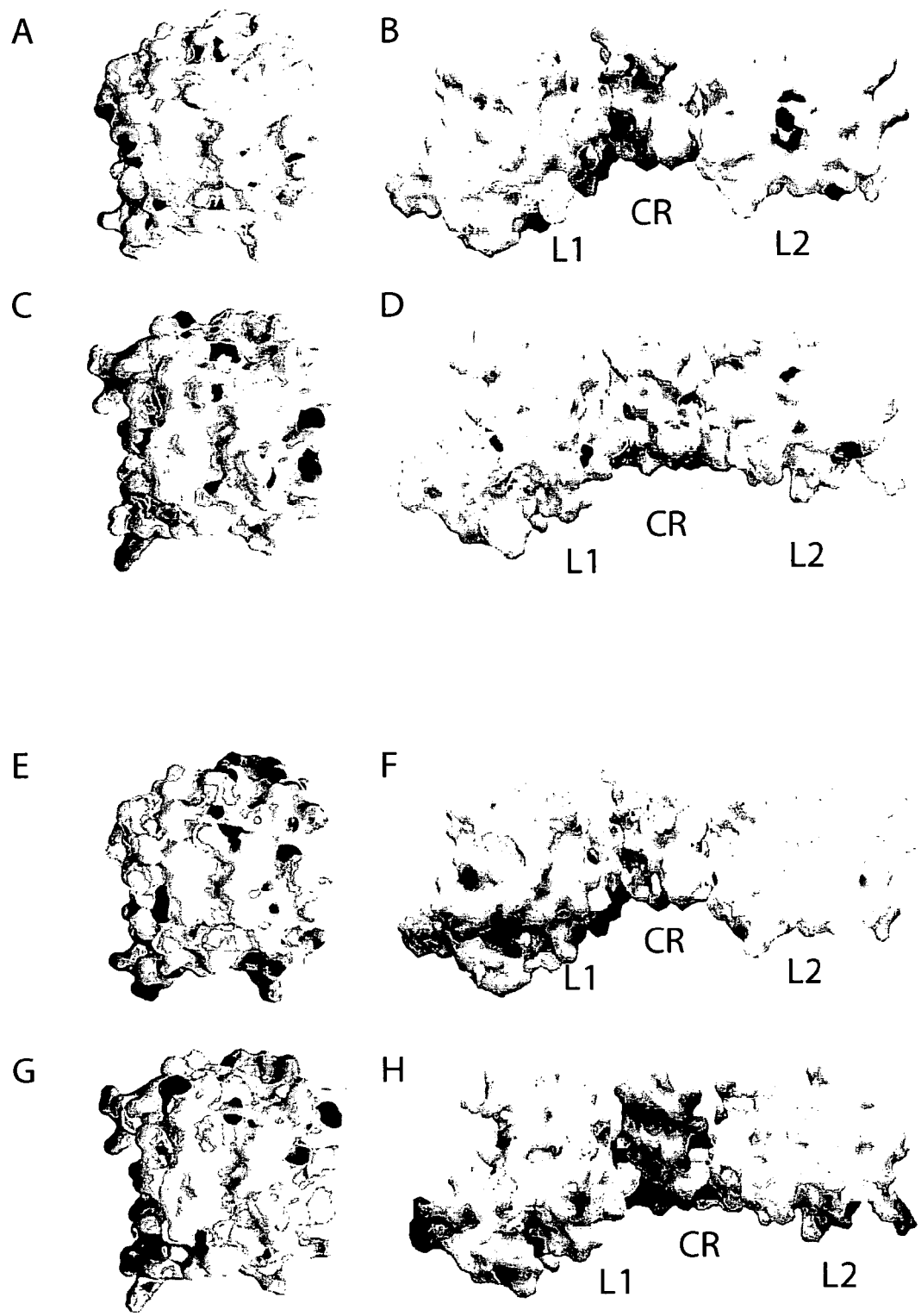
FIG. 5: Electrostatic potentials calculated for the L1, CR and L2 domains of IR and IGF-1R. Panels A and E: L1 of IR viewed into the face of sheet 2. Panels B and F: L1-CR-L2 of IR. Panels C and G: L1 of IGF-1R viewed into the face of sheet 2. Panels D and H: L 1-CR-L2 of IGF-1R. In Panels A to D the dark greyed surface indicates positive electrostatic potential >10 kT/e and in Panels E to H the dark greyed surface indicates negative electrostatic potential <−10 kT/e, with other shades of grey in both panels indicating either electrostatic potential closer to zero or molecular surface normals directed significantly away from the viewer, where k is the Boltzmann constant, T the temperature and e the magnitude of the electron charge. The atom charges used in the calculation were −0.5e for Asp OD1, Asp OD2, Glu OE1 and Glu OE2; +0.5e for Arg NE1 and NE2; and +1.0e for Lys NZ. The electrostatic potentials were calculated using GRASP (Nicholls et al., 1991).

The largest differences seen in the individual domain comparisons of IR and IGF-1R are in the two regions governing ligand specificity, the left hand side of the ligand binding surface of the L1 domain as viewed in FIG. 4, and the sixth module of the CR domain (FIGS. 3 and 5). The comparative backbone structures of the L1 domains of IR and IGF-1R generally follow each other closely owing to their high (70%) sequence identity (rmsd between Cα atoms of IR-1 and IGF-1R is 1.2 Å; and between IR-2 and IGF-1R is 1.3 Å). There is a major difference between the structures of IR residues 39-48 and the equivalent sequence in IGF-1R (residues 35-42) in the second leucine rich repeat of the L1 domain (FIG. 4), with the largest Cα deviations being near Lys40 (3.3 Å) and Pro43-Arg47 (3.5-4.2 Å). A striking feature is the disposition of the side chain of IR-Phe39 which can be seen to contribute to the ligand-binding surface (second β-sheet) of L1. This is in contrast to the corresponding residue, Ser35, at the end of the third β-sheet of IGF-1R, whose side chain extends in an orthogonal direction to that of IR-Phe39 (FIG. 4) and is thus in a position that is unlikely to contribute to low affinity ligand binding by the soluble ectodomain. As shown in FIG. 2, the IR sequence also has an insert of two amino acids in the region Lys40-Pro43 compared to IGF-1R. Phe39, and to a lesser extent Arg42 and Pro43, have been shown to be the key residues responsible for the increased insulin binding of IR/IGF-1R chimeras (Kjeldsen et al., 1994). The importance of Phe39 in insulin binding is further indicated by the data in Table 2 which show that five of the seven most important residues for insulin binding to IR, located in the region that governs specificity (first 68 residues of L1) are conserved in the IGF-1R and thus not responsible for this specificity difference. The two exceptions are Gln34 and Phe39, the importance of the latter being confirmed by site-specific mutagenesis analyses (Williams et al., 1995).

Other differences in L1 involve residues Pro43-Phe46 which form a short α-helix in IR-1 and IR-2, while the corresponding residues in IGF-1R do not (FIGS. 2 and 3), and the insertion of Gly4 at the start of the L1 domain in IGF-1R causes Pro5 in that structure to extend further (Cα deviation of 2.7 Å) into the central ligand-binding cavity than does the equivalent Pro9 in the IR-1 and IR-2 structures. The contribution, if any, of this difference to receptor binding specificity is not known. There is also a backbone deviation around Asn152 (4.1 Å) at the end of the L1 domain, a region of IR that also contains a single residue insertion compared to IGF-1R (see FIG. 2).

The other major difference in the two structures is seen in the CR domain (sequence identity 47%), which consists of 8 compact modules, and governs IGF specificity (Gustafson & Rutter, 1990; Schumacher et al., 1991; Kjeldsen et al., 1991; Hoyne et al., 2000) through its interaction with the C-domain of IGF (Zhang et al., 1994). The backbones of the third, fourth, and fifth modules in IR-1 and IGF-1R structures follow each other quite closely, while the backbones of the other modules deviate significantly. The largest difference is seen in module 6 in the region 260-276, corresponding to 253-265 in IGF-1R (FIG. 2). Here there is no sequence identity between the two receptors, and IR contains a 4 residue insertion and an extra disulfide bond (FIG. 2). Although the size of the insertion is modest, the new sequence forms an α-helix which extends further into the putative binding pocket (see FIG. 3) with the structure being maintained by the additional disulfide bond. Temperature factors in this region are relatively high and connected electron density was observed only in IR-1 and not in IR-2. However, this region is likely to be better ordered than in IGF-1R where the loop was ordered only by making a substantial crystal contact with an adjacent molecule (Garrett et al., 1998).

In addition to these structural differences (FIGS. 2 and 3), CR module 6 of IR shows very different electrostatic surface potential to IGF-1R (FIG. 5), reflecting the abundance of positively charged residues in the IR sequence compared to the acidic residues in the corresponding region of IGF-1R (FIG. 2). Both structures have electrostatic potentials that are dominantly negative in the L1 domains and dominantly positive in the L2 domains. However, the structures differ in the electrostatic potential in their CR domains, that of IR being predominantly positive while that of IGF-1R is overwhelmingly negative. The electronegative characteristics of the CR domain of IGF-1R are complementarity to the electropositive nature of the C-domain of IGF-I (that contains Arg36 and Arg37). The CR domain is the region in the receptor known to be important in governing IGF binding specificity (Gustafson & Ritter, 1990; Schumacher et al., 1991; Kjeldsen et al., 1991; Hoyne et al., 2000) and the region shown to be responsible for the recognition of IGF-1Residues Arg36 and Arg37 (Zhang et al., 1994). Alanine substitution of Arg36 and Arg37 leads not only to a 15-fold loss in binding potency for the IGF-1R but also to a 29-fold increase in binding potency to the IR (Zhang et al., 1994), consistent with the electrostatic differences discussed above.

In contrast to the differences seen between the L1 and CR domain structures in the two receptors, the L2 domains of IR and IGF-1R are very similar. There are no insertions or deletions in the L2 domain of IR relative to IGF-1R (FIG. 2) and the sequence identity for the L2 domains is high (65%). Consequently, the backbones of the L2 domains of IR-1 (0.9 Å) and IR-2 (0.8 Å) superimpose on the L2 domain of IGF-1R better than do the L1 domain comparisons, with only two significant deviations. The first deviation is in the vicinity of IR Glu316/IGF-1R Lys306 (3.0 Å) where a strong salt bridge between Glu304 and Lys309 in the case of IGF-1R facilitates the deviation of the IGF-1R backbone in this region compared to IR (residues Leu314 to Lys319). The other deviation is near Asn348/Asn338 (4.0 Å) in the loop between the third β-strand and the α-helix in the second repeat of L2. In both receptors this Asn residue is directed towards the external solvent. The L2 domain backbones of IR-1 and IR-2 also differ from each other most at these same regions (2.6 Å near Leu315 and 1.5 Å near Asn348).

Example 3

Ligand Binding Region of L1

The central (second) β-sheet of the L1 domain is a major contributor to ligand binding, based on studies of naturally-occurring receptor mutants and receptors subjected to alanine scanning mutagenesis (Table 2). Most of the mutant receptors from patients with defects in insulin binding (Taylor et al., 1994; Rouard et al., 1999) have mutations in this face. Similarly, of the 47 single site and six double site IR alanine mutations, the 14 mutations with defects in insulin binding (Williams et al., 1995) were all in this central β-sheet.

As illustrated in FIG. 5, the characteristic feature of this L1 face is a large hydrophobic patch with a cavity at the centre, formed by Q34, L36, L62, F64, F88, F89, V94, F96, R118 and E120 (FIG. 6B). Clearly this cavity can bind hydrophobic residues and two instances of this phenomenon have been observed. In the structure of IGF-1R, two residues, (L and I), from the c-myc purification tag sit in the L1 cavity on an adjacent molecule and in this study the side-chain of F89 in IR-2 is swung out and sits in the cavity of IR-1. The hydrophobic patch is ringed by hydrophilic amino acids and notably, charged residues, some of which are particularly important for insulin binding (FIG. 6D).

This L1 surface is highly conserved in IRs and is the largest conserved patch of surface in the L1-CR-L2 fragment in vertebrates (FIG. 6E). The most important residues for insulin binding in both the A and β isoforms of human IR are Arg14, Asn15 and Phe64, which, when replaced by alanine, resulted in receptors with negligible insulin binding ability (Table 2). The next most important set of L1 residues are Leu37 (20-fold reduction), Phe39 (10-to 25-fold) and Ile13, Gln34 and Lys121 (all 11-to 12-fold) followed by Asp12, Leu36, Leu87, Glu97 and Asn90 (6-to 9-fold reduction in affinity). Other residues Phe89, Tyr91, Met38, Glu44, Glu120, Tyr67 and Phe88 showed reductions in affinity ranging from 3-to 5-fold (Table 2). The mutation Leu87Ile increased binding four-fold (Nakae et al., 1995) while the Phe89 to Leu, Ile, Ser, Pro, Trp or H is mutations all abolished insulin binding (De Meyts et al., 1990). As shown in Table 2, the seven most important residues for insulin binding—Ile13, Arg14, Asn15, Gln34, Leu37, Phe39 and Phe64 plus five of the less important ones (Asp12, Leu36, Met38, Glu44, Tyr67) occur in the first 68 residues of IR, the region found to confer insulin binding specificity in IR/IGF-1R chimeras (Kjeldsen et al., 1991; Kjeldsen et al., 1994; Andersen et al., 1992). The distribution of these residues over the central (second) β-sheet of the L1 domain of IR is shown in FIG. 6D and can be seen to be a subset of the highly conserved residues found in the vertebrate IRs (FIG. 6C).

Example 4

Insulin-L1 Domain Binding Model

A possible model for the L1 domain-insulin interaction is shown in FIGS. 6E 6E and the atomic coordinates given in Appendix III and is based on fitting a hydrophobic surface of insulin (comprising residues from its dimer surface) onto the hydrophobic patch of the receptor described above. In the model presented here we have represented insulin in the R-state, (where the B-chain helix extends from B1 to B19), the more active conformation suggested to be adopted by insulin on binding to the receptor (Nakagawa et al., 2005). In addition, the B-chain has been truncated after residue GluB21, given the known mobility of the B-chain C-terminus (Hua et al., 1991; Ludvigsen et al., 1998; Wan et al., 2005), the increased binding affinity of B-chain despenta-amide insulins (Schaffer, 1994) and the low activity of the single-chain, B29-A 1 peptide-linked insulin despite its near native crystal structure (Derewenda et al., 1991). The B-chain C-terminus appears to not be essential for binding and is believed to rotate away from its close contact with residues A1 and A2 during the process of receptor interaction. This movement exposes the hydrophobic surface comprised of A1, A2, A3, A19, B24 B25 and B26 (Ludvigsen et al., 1998; Xu et al., 2004; Wan et al., 2005).

From the shape and size of these hydrophobic surfaces on the L1 face and the insulin dimer surface, the favoured orientation is with the B-chain helix running along the length of L1 from the bottom to the top, as viewed in FIG. 6E, with the critical insulin residue TyrA19 (Pullen et al., 1976; Kristensen et al., 1997) buried deep into the central hydrophobic cavity formed by Gln34, Leu36, Leu62, Phe64, Phe88 and Val94. The now-exposed GlyA1-ValA3 is placed up against residues Phe88 and Phe89 which are in the hydrophobic loop in the fourth LRR rung at the left hand edge of the L1 binding face (see FIGS. 2 and 3). Other key residues used to position insulin in the model are ValB12 and TyrB16, the contiguous residues from the B-chain helix, and PheB24 (Pullen et al., 1976; Kurose et al., 1994; Huang et al., 2004, Xu et al., 2004). Photoactivatable derivatives of TyrB 16 and TyrB24 have been shown to cross-link to the L1 domain of IR while ValB12 could not be derivatised without destroying its receptor binding ability (Huang et al., 2004; Xu et al., 2004). In this model, each of these three residues contacts the L1 binding face. ValB12 is buried in the interface and sits directly over Phe64 and the lower end of Arg65, with Phe96 underneath and Leu37 above, while TyrB 16, sits directly between Leu37 and Phe39, two of the residues which are highly sensitive to Ala substitution (Table 2). The residue equivalent to TyrB16 in IGF is Gln 15 and it is interesting to note that swapping IGF-1Residues Gln15 and Phe 16 with their counterparts TyrB16 and LeuB17 from insulin, increased the IR binding of the mutant IGF-I ten-fold but had no effect on its binding affinity for IGF-1R (Bayne et al., 1988). The atomic coordinates of the model are provided as Appendix III.

While not shown in the model, the mobile C-terminal tail of the insulin B-chain (residues 22-30) is envisaged to have moved away from the core of the ligand, to a position approximately 90° to the axis of the B-chain helix (see Hua et al., 1991). This movement places PheB24 in a position where it can still contact the top rungs of the L1 binding face to which it can be cross-linked (Xu et al., 2004); it places B25 in an exposed position to interact with the IR α-chain C-terminal 16 amino acids to which it can be cross-linked (Kurose et al., 1994) and has LysB29 extending over to the cleft between L1 and CR, a position consistent with the ability to label either of these receptor regions depending on the nature of the LysB29 side-chain derivative (Yip et al., 1988; Wedekind et al., 1989). Finally, in the model described, ValA3 and ThrA8, derivatives of which, like PheB25, can be cross-linked to the 13 kDa C-terminal fragment of the IR α-chain, are positioned on the bottom left hand surface of insulin (FIG. 6E) in a semi-exposed position but well away from PheB25. This supports the suggestion (Wan et al., 2004) that ValA3 and ThrA8 may contact a region of the insert domain that is peripheral to the critical site involved in contacting PheB25. Such disparate contact points by the IR insert domain are possible given it appears to be intrinsically disordered based on predictions with the DisProt web server (Peng et al., 2005). Such an orientation of insulin on the L1 surface results in LeuB17 and LeuA 13 (Schaffer, 1994) and other residues from the hexamer face, the so-called second binding region (De Meyts, 2004), being positioned where they can readily interact with other parts of the receptor dimer and induced IR signaling.

Figure 6:
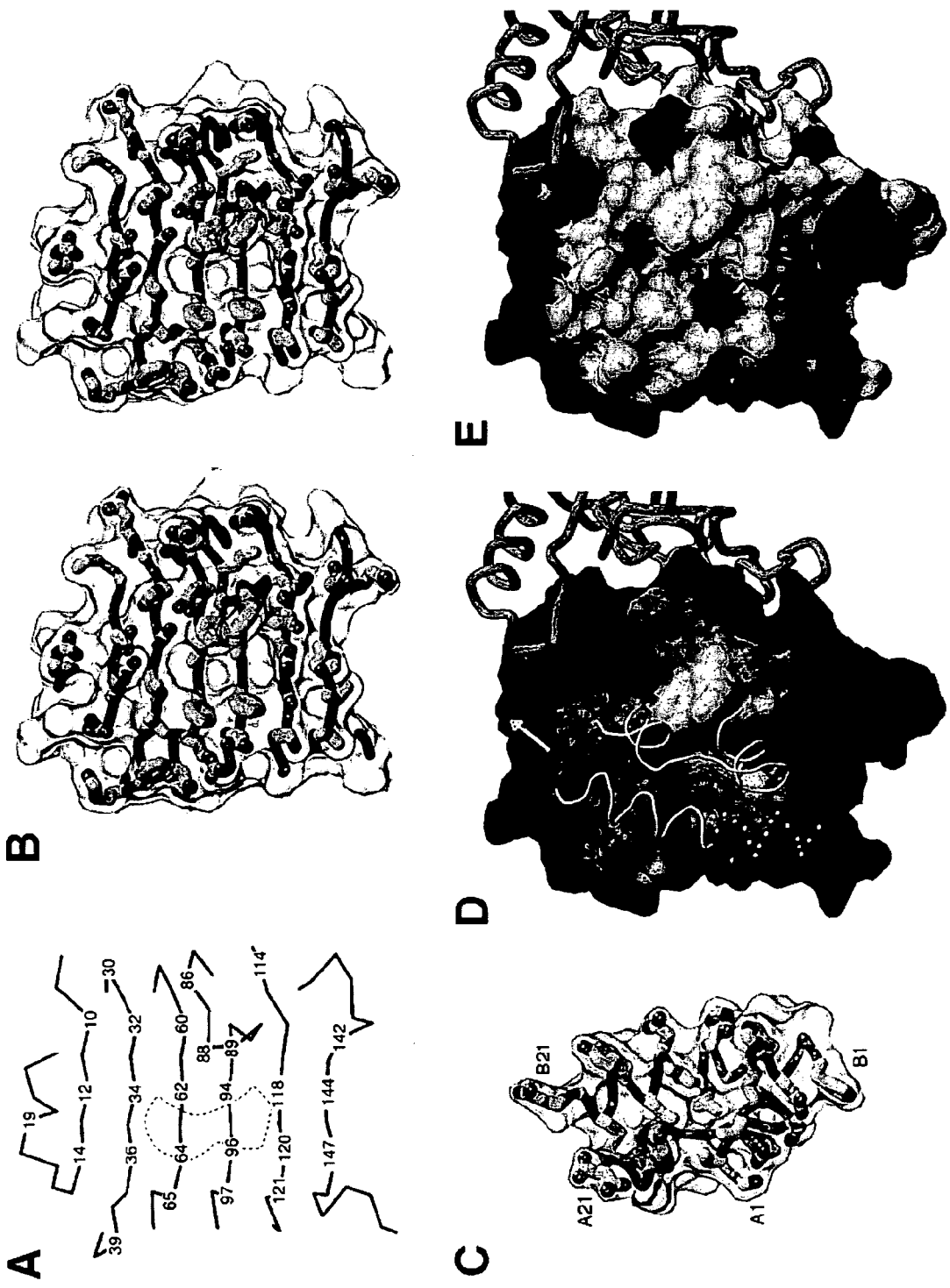
FIG. 6: The ligand binding face of the L1 domain of IR. (A) Cartoon showing the main chain trace and the location of key residues. The hydrophobic patch is indicated by the dashed trace when viewed in the same direction as panel B. (B) Stereo view of the L1 ligand-binding surface. (C) View of the surface of insulin that interacts with the binding face of the L1 domain of IR, rotated 180 degrees about a vertical axis relative to D. (D) Surface diagram of the L1 domain of IR. Residues are shaded according to relative affinity of insulin for alanine substitutions; in three grades: <5%; 5-15%; 15-50% and no expression (see Table 2). The potential location of bound insulin is depicted in white, with residues B1-B8 dotted, A1-A20 and B9-B21 as a thin trace and an arrow to indicate the approximate position of residues B22-B30. The view direction is the same direction as in panel B and part of the Cys-rich domain trace is in purple. (E) Surface conservation based on sequence alignment of vertebrate insulin receptors. The most conserved surface region in the L1-CR-L2 fragment is the putative ligand-binding site on L1, with strictly conserved residues lightly shaded. Thirteen sequences were used from mammals, birds, amphibians and fish (NCBI accession numbers: P06213, AAR04440, P15208, P15127, XP_542108, XP_418250, Q9PVZ4, XP_690534, XP_691069, BAB836677, BAB83668, CAG083667, CAG08022). View as in panel B.

As shown in FIG. 6, the hydrophobic patch on IR is ringed with charged residues as is the hydrophobic patch on insulin. A number of these hydrophilic residues—GluA4, AsnA21 and GluB 13 on the periphery of the insulin hydrophobic patch could form favourable interactions with Arg118, Gln34 and Arg65 on the IR L1 binding surface and the A chain N-terminus could salt link to Glu120. Clearly the central cavity in L1 binds hydrophobic residues and two instances of this phenomenon have been seen previously. In the structure of IGF-1R (Garrett et al., 1998), two residues, (Leu and Ile), from the c-myc purification tag sit in the L1 cavity on an adjacent molecule and in this study the side-chain of Phe89 in IR-2 is swung out and sits in the cavity of IR-1.

In the model described above for insulin binding, van der Waals or hydrophobic interactions contribute the major portion of the ligand-receptor binding energy. However, as discussed earlier with IGF-I binding to the IGF-1R, electrostatic complementarity between the electropositive C-domain and the electronegative sixth module of the CR domain would have an additional orientational effect and could be the driving force in binding in the IGF-1/IGF-1R complex. Binding of insulin to the insulin receptor appears to be less electrostatically driven.

Both IGF-I and IGF-II both can compete with insulin on either IR or IGF-1R (Adams et al., 2000) and, as receptors and ligands have homologous sequences, the preferred orientations of these ligands on IR and IGF-1R receptors is the same. A model for IGF-I or IGF II binding to IR can therefore be generated from the model of insulin binding to IR by taking the structures of IGF-I or IGF-II and superimposing C-alpha coordintes of identical residues as defined by the alignment in FIG. 11 of Adams et al. (2000). These models can then be used the same manner as that for insulin in the design of molecules which interact with IR or IGF-1R to modulate their actions.

Example 5

Quaternary Structure of the IR-A Ectodomain

Domain arrangements. The IR construct used in these studies comprises all of the residues within the mature IR-A polypeptide ectodomain except for the region of O-glycosylation, residues 735-753, in the insert domain, ID, near the N-terminal end of the β-chain. Also deleted is residue 917, the last residue before the transmembrane region, while residues 731-734 have been mutated. The construct lacks the N-linked sites at 730 and 743 and the six O-linked glycan sites at Thr732, Thr737, Thr745, Ser746, Thr747 and Thr751 (Sparrow, 2006).

Figure 7:
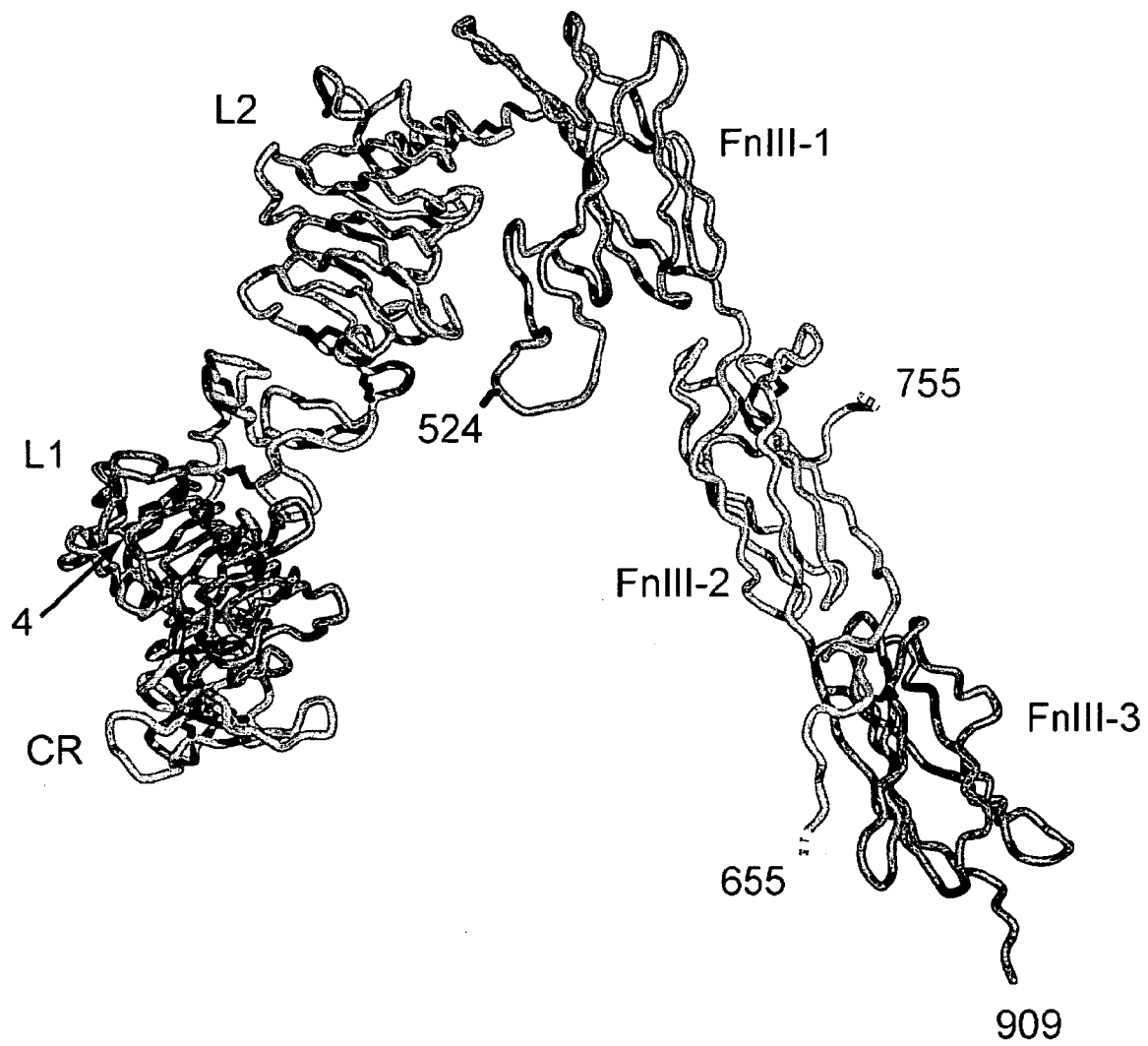
FIG. 7: Illustration of the polypeptide fold for the IRΔβ monomer showing the relative arrangement of the L1, CR, L2 and the three FnIII domains. Intra-monomer disulphides are shown in black stick representation, whilst the location of the inter-monomer disulphide at residue 524 is explicitly labelled. The observed termini of the α-and β-chains are indicated by residue numbers. Electron density was not seen for α-chain residues 1-3 and 656-719 or for β-chain residues 724-734, 754 and 910-916.

The crystallographic asymmetric unit structure comprised one IR ectodomain α-β-chain pair (i.e. the ectodomain monomer), one 83-7 Fab and one 83-14 Fab. The structure of the IR monomer is shown in FIG. 7 and the comparative sequences and secondary structure assignments in FIG. 2. The consecutive domains of each α-β-chain monomer have an "inverted V" layout with respect to the cell membrane. One leg of the V is formed by L1-CR-L2 and the other by an extended linear arrangement of FnIII-1, FnIII-2 and FnIII-3. The ID is mostly disordered in this structure with electron density visible only for the first 20 and the last 4 of the 104 residues in the construct. This is consistent with our predictions of secondary structure using the method of Peng et al. (2005), that the ID region is largely disordered. At the apex of the inverted V lies the connection between L2 and FnIII-1: these domains do not appear to be in extensive contact. The relative arrangement of the L1, CR and L2 domains observed here is similar, though not identical, to that observed for these domains in isolation for both human IR (see examples 1-4) and human IGFR-1 (Garrett et al., 1998). In particular, the centre-of-mass of the L2 domain is positioned 5 Å to 10 Å closer to the L1 domain here than is observed in the L1-CR-L2 fragment structures.

Figure 8:
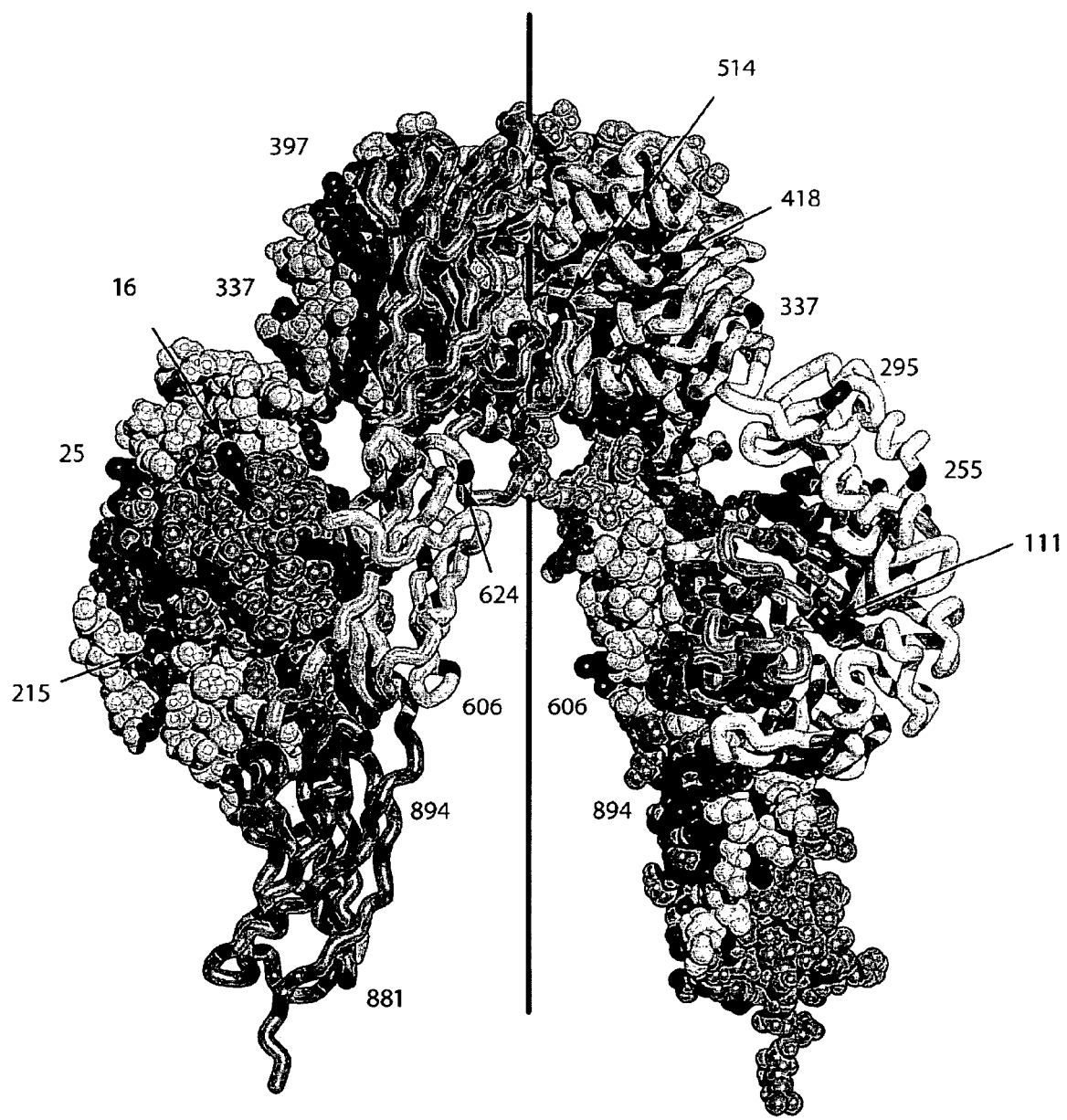
FIG. 8: Schematic diagram of the IRΔβ homodimer (SEQ ID NO:15) showing the juxtaposition of domains between the monomers. One monomer is shown in tube representation whilst the other is shown in CPK representation. The location of potential N-linked glycosylation sites are shown in black with the residue numbers indicated.

The above monomers pair unambiguously within the unit cell to form the IR ectodomain homodimer, with alternative pairings showing negligible interaction (see below). The homodimer arises from a two-fold rotation of the monomer about an axis running approximately parallel to, but displaced about 10 Å from, the axis of the inverted V (FIG. 8). The homodimer thus retains the inverted V conformation with the L2 domain of the first monomer in contact with the FnIII-1 domain of the second monomer at the apex and the L1 domain of the first monomer in contact with the FnIII-2 domain of the second monomer at the approximate midpoint of one of the two legs of the inverted V. The ligand-binding faces of the two L1 domains are thus located on opposite sides of the dimer some 65 Å from each other, a distance that is too great to allow insulin to contact both L1 domains simultaneously as previously suggested for the high affinity state of the insulin/IR complex (Luo et al., 1999; Ottensmeyer et al., 2000, 2001; Yip & Ottensmeyer, 1999). The C-termini of the two FnIII-3 domains are at the base of the inverted V structure where, in the intact IR, they would extend through the cell membrane to the tyrosine kinase domains (FIG. 1)

Located at the apex of the IR dimer, in close proximity to each other, is the pair of Lys460 residues in the last leucine-rich repeat in L2, residues that have been implicated in the regulation of co-operative interactions between the two monomers in the IR dimer and suggested to be the sites for chemical cross-linking of IR monomers with disuccinimidyl suberate (Kadowaki et al., 1990). The Lys460Glu mutation was found in a patient (leprechaun/Ark-1) with insulin resistance resulting from the effect of this mutation on increased stability of insulin binding at acid pH, impaired dissociation of the insulin-IR complex following internalization, impaired IR recycling and accelerated IR degradation (Kadowaki et al., 1990). The side chain of Lys460 is surrounded by three acidic residues Asp464, Asp574 and Glu575. While the Lys460Glu mutation would make this region considerably more electronegative, it is not clear why this leads to the phenotype described, nor why the Lys460Arg mutation markedly diminishes the ability of the mutant IR to display negative co-operativity (Kadowaki et al., 1990). The importance of the L2 domain in mediating signal transduction is further supported by the properties of two mutant receptors, Phe382Val (Accili et al., 1991) and Trp412Ser (van der Vorm et al., 1994) from human patients. These residues occur in equivalent positions in the third and fourth repeats of L2 (FIG. 2). Neither has a significant effect on insulin binding, but both inhibit the capacity of the IR to undergo insulin-mediated autophosphorylation, presumably by distorting the structure of the L2 domain and its interactions with the FnIII-1 domain of the other monomer.

Fab contacts. Previous studies with receptor chimeras have established that the epitope for the mouse monoclonal antibody 83-7 lies in the residue segment 191-297 (Adams et al., 2000) and the epitope for mouse monoclonal antibody 83-14 lies in the residue segment 469 to 592 (Prigent et al., 1990). The sequences for these Fabs are provided in FIGS. 9 and 10). Our structure supports these results (FIG. 11).

The 83-7 Fab is observed to interact via its CDRs with residues within the segment 233 to 281 of the CR domain. This epitope includes primarily the fifth module of the CR domain and also parts of the fourth and sixth CR modules. Of the eight sequence differences (Ser210Lys, Gln218Glu, Arg236Gln, His264Phe, Lys267Arg, Arg271Lys, Gln272Pro and Leu300Met) between the CR domains of human and mouse IR only 8236 is located in the 83-7 epitope.

Figure 11:
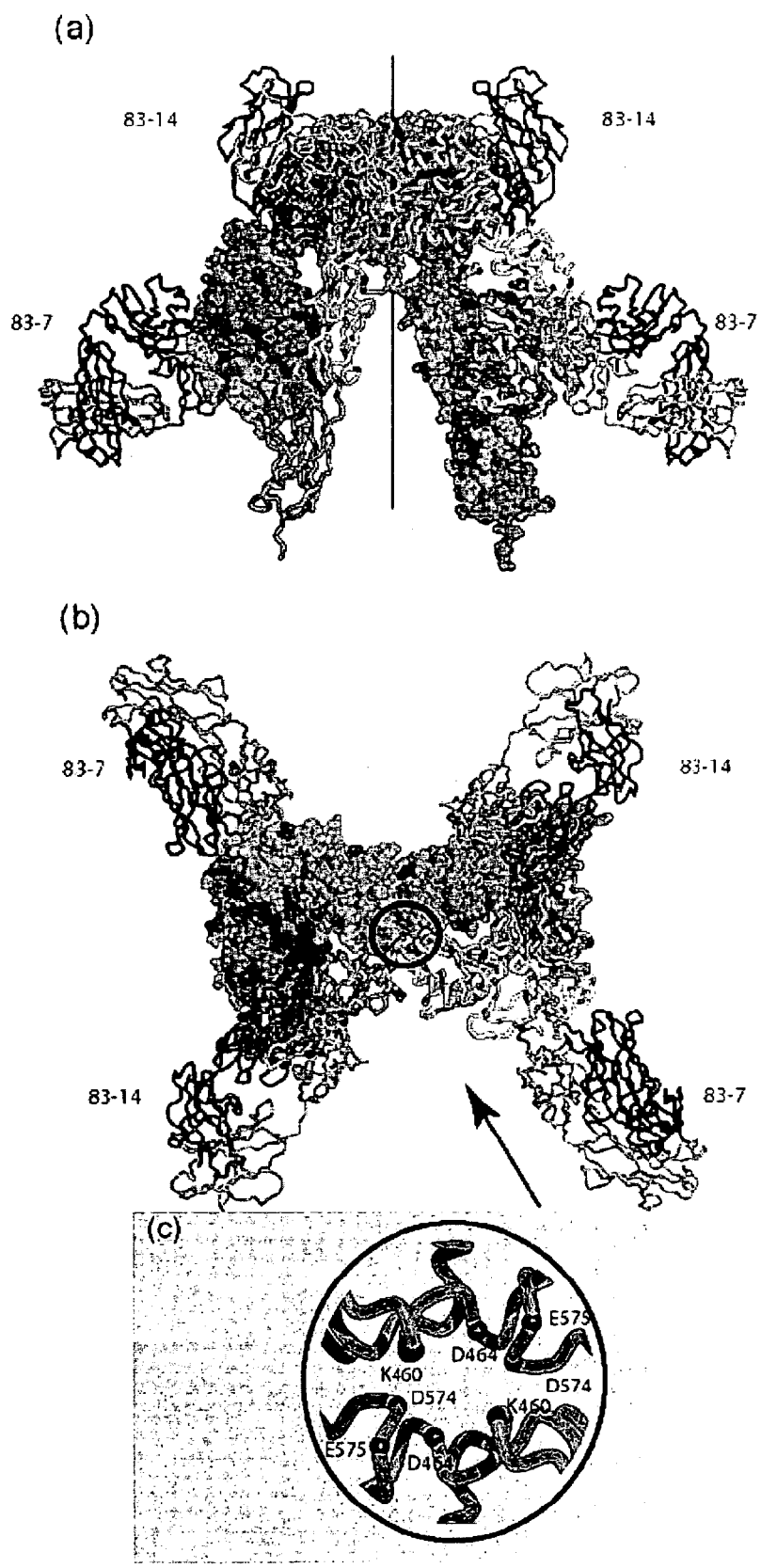
FIG. 11: Orthogonal views of the IRΔβ homodimer with the attached pairs of Fabs. The IRΔβ homodimer is represented and shaded as in FIG. 7. The Fab fragments are represented and coloured as follows:— 83-7 heavy chain: thin dark shaded tube, 83-7 light chain: thin light tube, 83-14 heavy chain: thin dark tube, and 83-14 light chain: thin light tube. (a) viewed orthogonal to the homodimer axis, (b) viewed down the homodimer axis (with the viewing direction of panel (a) being indicated by the arrow), (c) detailed zoom-in on the circled area of panel (b), showing the cluster of charged residues around the homodimer axis.

The 83-14 Fab in our structure interacts solely with FnIII-1 (FIG. 11). Portions of the A strand (residues 476-481) of FnIII-1 lie parallel to and on top of the cleft formed by the 83-14 heavy and light chain CDR3s, whilst portions of the B strand (residues 484 to 490) and E strand (residues 546 to 554) of FnIII-1 form contacts with the remaining molecular surface of the heavy chain CDRs. Of the five sequence differences (Tyr477Phe, Leu538Gln, a two residue insertion between 546-547 and N547S) between human and mouse IRs only Tyr477 is buried in the epitope. Residues 546 and 547 are on the periphery. The constant domain of the 83-14 Fab is somewhat disordered in our structure, lying in very poorly defined electron density and forming no crystal contact with any other domains within the crystal structure.

The psuedo two-fold axis of the variable domains of both Fabs lie approximately 45° to the two-fold axis of the IR ectodomain homodimer and protrude as extended "handles" to the IR ectodomain structure (FIG. 11). Interestingly, the overwhelming majority of the inter-molecular contacts within the crystal (i.e. between one Fab-complexed IR ectodomain and its neighbour) are Fab-to-Fab. The Fabs thus "shield" the heavily glycosylated IR ectodomain from direct involvement in crystal contacts and arguably play a key role in the success of crystallization. The only exception is the involvement of the FnIII-3 domain of the receptor in a crystal contact with the constant domain of the 83-7 Fab attached to a neighbouring receptor.

The segment of electron density extending across the ligand-binding face of the L1 domain. The different electron density maps revealed a tube of density lying across the ligand-binding face of L1 at an angle of approximately 45° to the β-strands (FIG. 12(a)). Without being bound, it is believed that this density may arise from the C-terminal region of the IR ectodomain (residues 704-719, the "CT peptide") or residues immediately upstream thereof. The CT peptide is known to be required for ligand binding (Kristensen et al., 1998, 1999) and lies in close juxtaposition to the L1 domain (Xu et al., 2004). In principle there are two possible connections for this putative CT segment in the dimer. It may belong to the same IR monomer as the L1 domain against which it is positioned, or it may belong to the ID of the second monomer. Without being bound, it is believed the latter arrangement in wild type receptor is more likely, given that pro-receptor cleavage occurs after receptor dimerisation (for a review of receptor biosynthesis see Adams et al., 2000) and that the crystal structure shows that dimerisation of the uncleaved IR would position the CT region of one monomer in the immediate vicinity of the ligand-binding surface of the L1 domain of the other. This arrangement has now been experimentally confirmed by complementation analysis (Chan et al., 2007).

Example 6

Secondary Structure of the Fibronectin Domains and Location of the Inter-Chain Disulphide Bonds The structure provides experimental confirmation of three fibronectin Type III domains in the IR. Whilst their existence has been predicted previously on the basis of sequence analysis (O'Bryan et al., 1991; Schaefer et al., 1992; Mulhem, et al., 1998; Marino-Buslje et al., 1999; Ward, 1999), the details of the location of the individual strands within these domains and the location of the insert domain (ID) within FnIII-2 have been unclear. These details are now presented in FIGS. 2 and 7.

Cys524 which forms one of the inter α-chain disulphide bonds with its corresponding Cys524 partner, lies within a large, 28 residue loop (Lys508-Asp535) linking the C and C' strands of the FnIII-1 domain. While the electron density associated with this segment is relatively weak and disjointed, the loop was built in to the density to show that the reported inter α-chain disulphide bond (Sparrow et al., 1997) is possible. The α-β disulphide Cys647-Cys860 is observed, with Cys647 lying in the ID in a long extension of the C strand of FnIII-2 that runs parallel to FnIII-3. Its partner, Cys860, is located close to the C-terminus of the C' strand of FnIII-3. An internal disulphide bridge links Cys786 and Cys795 at the base of the F-G loop in FnIII-2. The unpaired C872 (Sparrow et al., 1997) has its side chain partially buried in FnIII-3. It has no counterpart in the IGF-1R (FIG. 2) or the insulin receptor related receptor (Sparrow et al., 1997).

The structure reported here also reveals that the insert domain (ID), which contains the α-β cleavage site at Arg720-Arg723, is located in the C—C' loop of FnIII-2 and consists of 123 residues (A1a636 to Pro758). No convincing electron density is seen for 80 (Arg656-Ala734//Glu754) of the 104 residues that make up the truncated ID in our construct, implying that these segments are significantly disordered in our crystal. This disordered region contains the last 64 residues (Arg656-Ser719) of the IR α-chain including the three cysteine residues (Cys682, Cys683 and Cys685) involved in the second set of α-α disulphide bonds (Sparrow et al., 1997). This disordered region also contains the modified (see methods) N-terminus of the β-chain (Ser724 to 7Asn34//Glu754). As shown in FIG. 8, the N-terminal region of the α-chain ID region can be seen to extend down on the inside of the inverted V, almost to the bottom of the last FnIII domain, with the pair of Ser655 residues at the end of the visible density approximately 60 Å apart, sufficiently close to allow the cysteine triplet (Cys682, Cys683 and Cys685) to form the observed inter-chain disulphide bonds (Sparrow et al., 1997).

The previous predictions of the FnIII boundaries and strand locations (O'Bryan et al., 1991; Schaefer et al., 1992; Mulhern, et al., 1998; Marino-Buslje et al., 1999; Ward, 1999) are shown to be mostly correct. However, none positioned the FnIII-1 C' strand or the FnIII-2 C' strand correctly, and in each case only one of the predictions was correct for the E strands of FnIII-1 (Marino-Buslje et al., 1999) and FnIII-3 (Schaefer et al., 1992). None positioned the ID in the C—C' loop of FnIII-2.

Example 7

N-linked Glycosylation

The IR ectodomain homodimer contains a total of 36 potential N-linked glycosylation sites distributed across all of the extracellular domains (Adams et al., 2000). There are 14 predicted sites for N-glycosylation in the hIR α-chain (residues 16, 25, 78, 111, 215, 255, 295, 337, 397, 418, 514, 606, 624, 671) and four in the β-chain (residues 742, 755, 893, 906, IR-B numbering). The presence of such a high degree of glycosylation (about one site per fifty residues) is likely to be one of the factors that has hindered attempts to crystallize the intact IR ectodomain. Electron density corresponding to glycan was seen at residues 16, 25, 111, 215, 255, 295 (poor), 337, 397 and 418, but not at Asn78, as previously reported in the structure of the L1-CR-L2 fragment of IR (see examples 1-4) and at five (514, 606, 624, 881 and 894, IR-A numbering) of the six N-linked sites that are present in the insert domain and the three FnIII domains of our construct. These findings are consistent with our chemical analyses of isolated IR glycopeptides summarised in Table 5. As shown in FIGS. 8 and 11, the N-linked glycosylation sites in the L1-CR-L2 half of the monomer are distributed over the outer surface of these domains, away from the surfaces involved in ligand binding or monomer-monomer interactions in the dimer.

To elucidate the structural consequences of N-glycosylation on the accessibility of different domains for protein-protein, protein-macromolecular or protein-small molecule interactions we determined the chemical composition of the oligosaccharides in the exon 11 plus (or B isoform), of the hIR ectodomain expressed and secreted from the CHO-K1 cells. The enzyme digests and the chromatographic procedures used to isolate each glycopeptide are summarized in FIG. 13 and Table 4 and the glycan compositions for the isolated glycopeptides are summarized in Table 5. Mass spectrometry showed that eleven sites had multiple species of complex glycans (residues 16, 25, 255, 295, 418, 606, 624, 742 and 755, IR-B numbering) or high mannose glycans (residues 111, 514) while only single glycans were identified at Asn671 (GlcNAc2Man3Gal4Fuc) and Asn215 and Asn893 (both GlcNAc2Man6, IR-B numbering). The N-linked sites at Asn397 and Asn906 (IR-B numbering) were shown to be glycosylated by amino acid sequencing but were not characterized by mass spectrometry due to insufficient material. The N-linked site at Asn78, and the atypical site Asn282LysCys, were not glycosylated. The peptide containing the final site, Asn337, was not recovered.

Figure 14A:
FIG. 14: Schematic diagram of the IRΔβ homodimer showing the distribution of the N-linked glycans modelled at their respective locations on the surface of the human IRAΔβ ectodomain dimer: (a) viewed orthogonal to the homodimer two-fold axis, (b) viewed along the homodimer two-fold axis towards the apex of the inverted "V"-shaped molecule (i.e. away from the membrane), (c) viewed along the homodimer two-fold axis towards the base of the inverted "V"-shaped molecule (i.e. towards the membrane). The protein molecular surface is shown in light grey atomic sphere representation whilst the glycan atoms are shown as black atomic sphere representation.
Figure 14B:
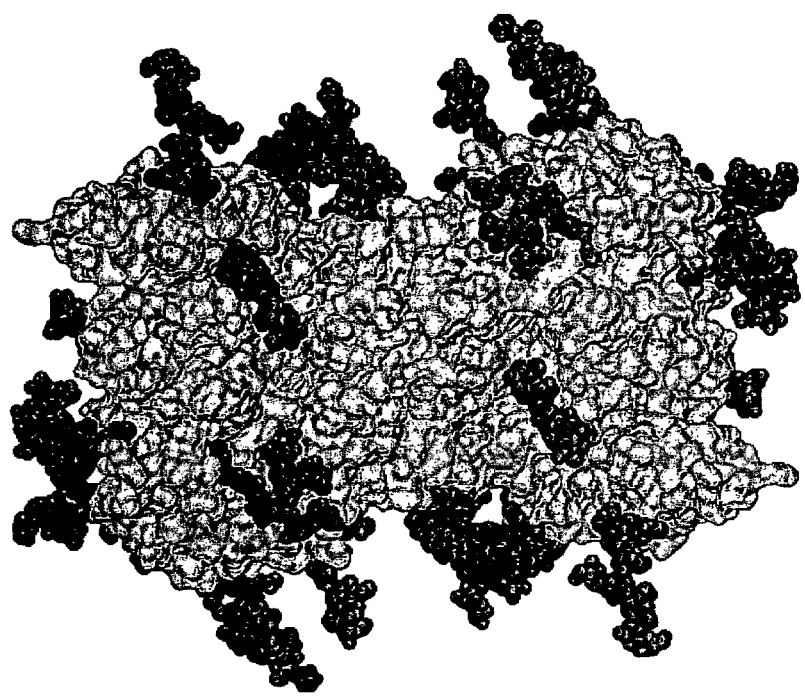
Figure 14C:
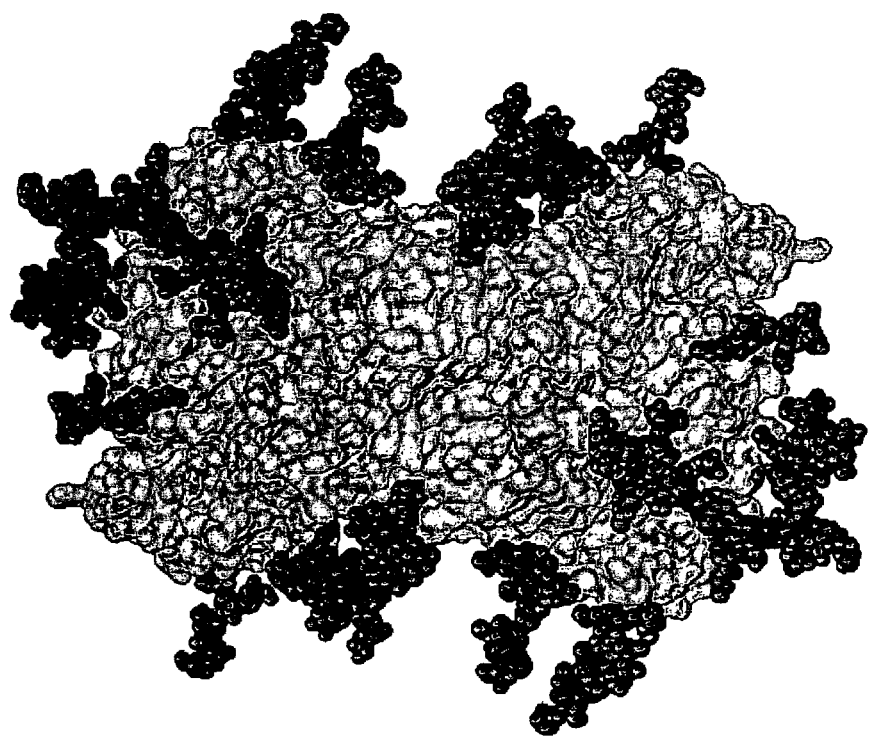

The structure of the IR ectodomain with the glycan structures incorporated is shown in FIG. 14 and the coordinates for the glycosylated IR are listed in Appendix IV.

Example 8

Comparison with Electron Microscopy Data

Figure 15:
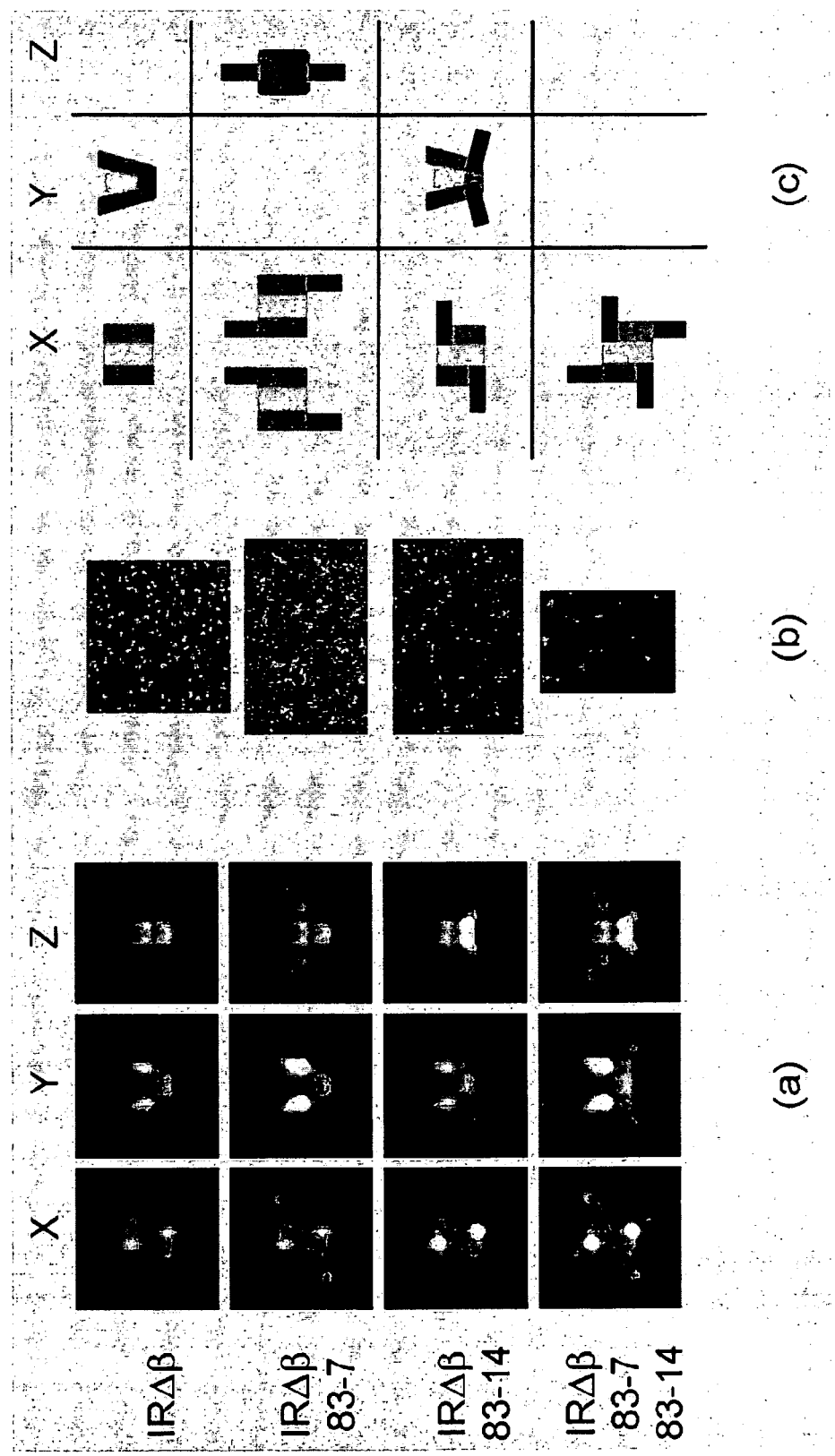
FIG. 15: A comparison of simulated projection images with previously determined negative stain images. (a) Simulated projection images at ~20 Å resolution obtained from the crystal structure of IRΔβ in isolation and in complex with 83-7 Fab and/or 83-14 Fab. (b) Negative stain images obtained from the same complexes by Tulloch et al. (1999), their FIGS. 2-4, used by permission. (c) Orthogonal views of the particles observed in (b) as proposed by Tulloch et al. (1999). Projection images in (a) were obtained using SPIDER (Frank et al. 1999).
Figure 16:
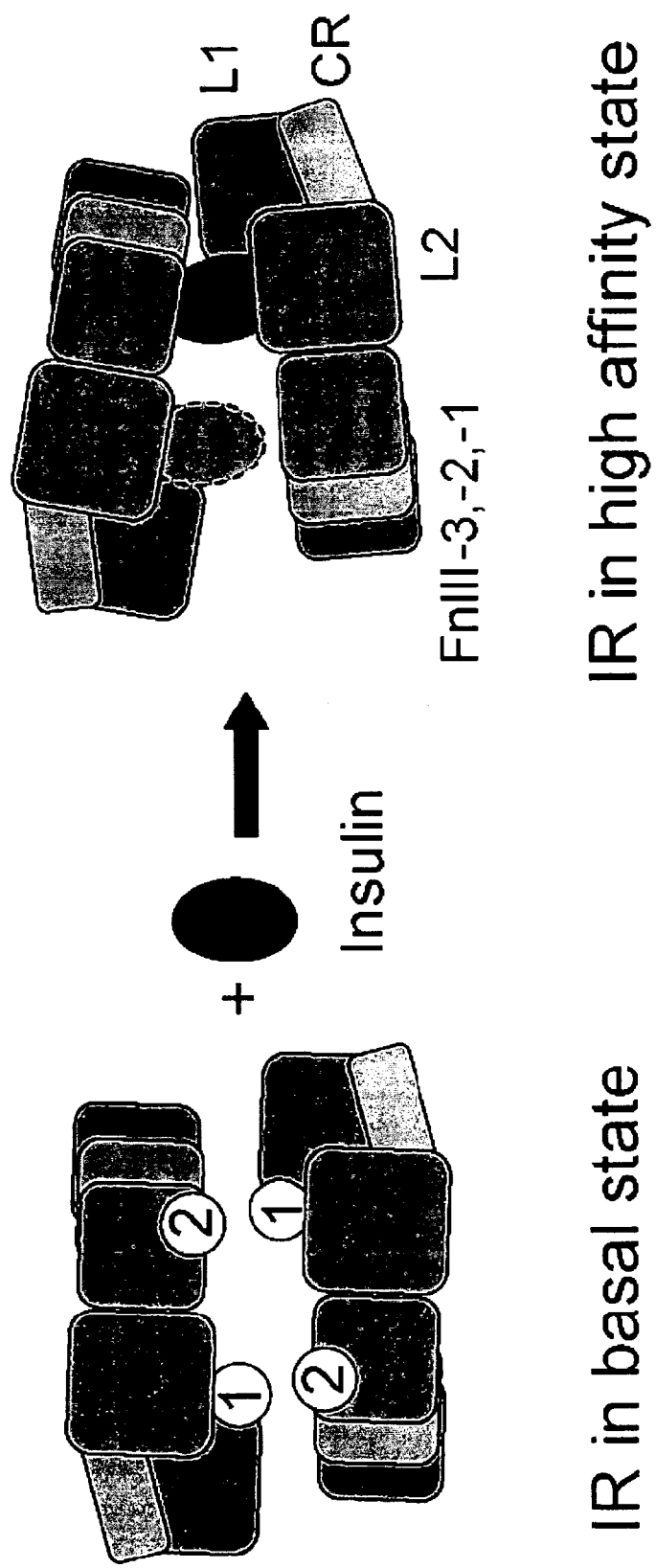
FIG. 16: Cartoon of insulin binding to membrane anchored IR. The symmetrical alignment of the ectodomains of the two monomers in the IR dimer are shown when viewed down the Y-axis. The shading for the domains are the same as in FIG. 7. The approximate locations of Sites 1 and 2 on each monomer are indicated by the numbered circles. In the basal state both low affinity sites are equally accessible. In the high affinity state, one insulin molecule crosslinks Sites 1 and 2 on one side of the dimer causing the two monomers to close up on that side and open up on the opposite side. Negative co-operativity is explained by the formation of the alternate cross-link involving the two left over binding sites and the disruption of the first bridging contacts. The monomers in the dimer can be viewed as "see-sawing" between these two alternatives.

Low-resolution projection images generated from our structure both with and without the 83-7 and 83-14 Fabs attached, can be compared with negative stain electron micrograph images obtained previously (Tulloch et al., 1999) (FIG. 15). The correspondence of our projected structure with these images is striking, suggesting that the three-dimensional structure observed here in the crystal is closely similar in conformation to the particles observed in our EM studies (Tulloch et al., 1999). However, the current structure reveals that the original interpretation of the EM images in terms of the arrangement of domains was incorrect. The L1 and L2 domains of one monomer are not in an upper layer at the ends of the U or V in contact with the L2 and L1 domains of the other monomer respectively, nor do the FnIII domains form a second layer at the bottom of the U (Tulloch et al., 1999). Rather, the U-shaped EM model should be inverted with the apex being formed by the L2 and FnIII-1 domains and the two legs by L1-CR-L2 and FnIII-1-FnIII-2-FnIII-3 respectively as described above.

We are unable to correlate our model with that proposed for the whole receptor in complex with insulin based of a 3D reconstruction of approximately 700 STEM dark-field images (Luo et al., 1999; Ottensmeyer et al., 2000, 2001; Yip & Ottensmeyer, 1999). Our data are incompatible with their suggested overall shape of the particle and with their proposed arrangement of domains. In particular, their EM model has the L1 domains protruding at the membrane distal end of the molecule and the FnIII-2 and FnIII-3 domains lying coplanar to the membrane, whereas our structure has the L1 domains lying towards the centre of the molecule at the start of one leg of the inverted V and the FnIII domains arranged in a linear fashion forming the other leg (FIGS. 7 and 8). These differences may be a consequence of structural transitions upon insulin binding, similar to that seen with the EGFR family (Burgess et al., 2003), given their EM data is on the detergent solubilised, high-affinity, whole receptor/insulin complex compared to our crystal structure on low affinity IR ectodomain. However this appears to us to be unlikely given the observation that ligand binding causes the receptor to become more compact rather than more extended (Lee et al., 1997; Florke et al., 2001).

Example 9

Implications for Signalling

Residues implicated in insulin binding by IR have been identified by examining patients' receptors, site-directed mutants, chimeric receptors and chemical cross-linking (reviewed in—Adams et al., 2000; De Meyts & Whittaker, 2002; Ward et al., 2003).

This data reveals the importance of residues in three regions of the receptor:
(i) the central β-sheet of the L1 domain;
(ii) the last 16 residues of the α-chain (the so-called CT peptide) (Surinya et al., 2002); and
(iii) the central modules of the CR region.

The CR region appears to be involved in restricting IGF-I binding to IR and promoting IGF binding to the IGF-1R. The electrostatic potential properties of the CR region differs markedly between the two receptors with that of IR being predominantly positive while that of IGF-1R is overwhelmingly negative as discussed in Example 2. These three ligand contact regions (L1, CT and CR) are all important for ligand binding to soluble ectodomain and account for the low affinity site that governs specificity. The details of the low affinity site and the potential interactions with ligand that govern specificity are discussed in detail in Examples 1-4.

Figure 12:
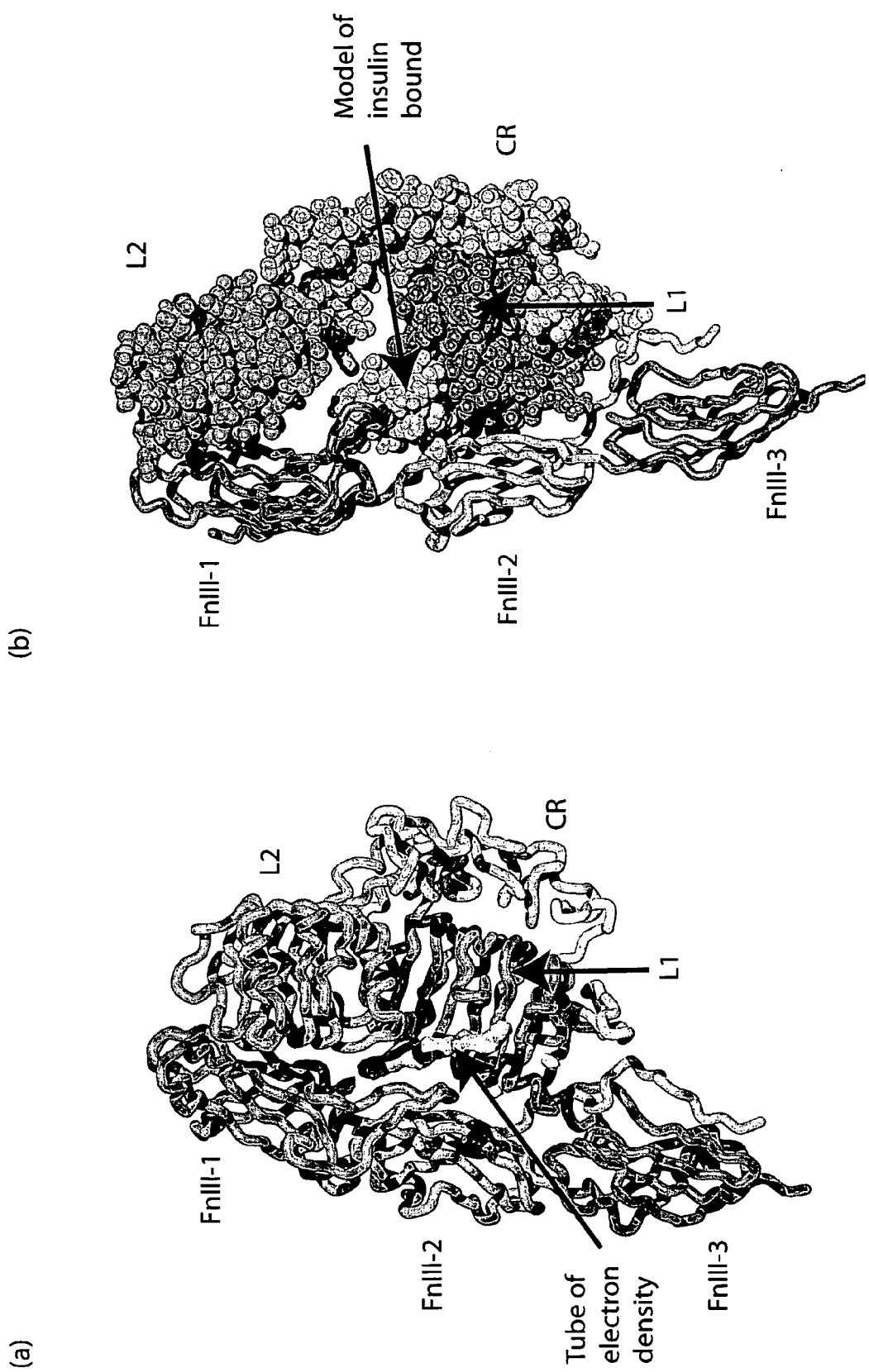
FIG. 12: (a) (a) Additional electron density on the face of the L1 domains of the IRΔβ ectodomain homodimer. This density is tentatively interpreted to correspond to a segment of the insert domain ID, most likely to the C-terminal region of the receptor α-chain (residues 704-719). (b) Schematic diagram of possible binding location of insulin bridging two monomers in the IRΔβ homodimer. Note that in this diagram the L1, CR and L2 domains are from one monomer within the homodimer, whilst the FnIII domains are from the other monomer. Domains are shaded as in FIG. 7, whilst insulin is shown in grey CPK representation. The positioning of insulin is based on the model of insulin bound to L1-CR-L2 (described in Example 4).

The generation of the high affinity binding state leading to the initiation of IR autophosphorylation requires additional receptor contacts that induce a change in the conformation of the IR dimer (Schaffer, 1994). The domain arrangements seen in the present structure indicate how such high affinity binding may occur. Our structure reveals how an insulin molecule bound to the L1 and α-chain CT binding site of one receptor monomer could make contact with the AB, CC' and EF loops of FnIII-1 from the other to generate the high affinity state (FIG. 12b). Evidence supporting the involvement of these portions of FnIII-1 in high affinity binding is:
(i) the demonstrated importance of the region 325-524 in insulin binding to IR/IGF-1R chimeras (Schumacher et al., 1993);
(ii) the labeling, with a photoreactive PheB1 insulin derivative (Fabry et al., 1992), of an 18-kDa fragment (extending from Gly390 to either Arg498 or Lys508 allowing for the two N-linked glycans at 397 and 418) and
(iii) the differential binding properties of a series of truncated IR ectodomains (Kristensen et al., 1999; Surinya et al., 2002).

The only differences between the IR593.CT fragment, which shows high-affinity binding (Surinya et al., 2002), and the IR mini-receptor (Kristensen et al., 1999) which binds insulin with 1000-fold lower affinity, are the presence of the first fibronectin domain (FnIII-1) between L2 and the CT peptide and the assembly of IR593.CT into a disulphide-linked dimer.

Examples 1-4 present a model for insulin binding to the L1 face of IR. The model is consistent with the above suggestions for the formation of the high affinity state and has the residues corresponding to the hexamer face of insulin (Schaffer, 1994; De Meyts, 1994; De Meyts, 2004), the so-called second site, fully exposed. The structure of the IR ectodomain dimer, described in Examples 5-10 suggests that this second region of insulin binds to one or more of the three loops AB, CC' and EF in FnIII-1 on the other monomer to generate the high affinity, signalling complex. Molecular modelling based on the wild-type receptor-like properties of the IR ectodomain-GCN4 leucine zipper chimera (Hoyne et al., 2000) suggests that the distance between the pair of FnIII-3 domains, observed here with the soluble ectodomain, could be halved in the membrane-anchored wild type receptor dimer. This would result in an increase in the distance between the L1 domain ligand-binding face and the loops of FnIII-1 adjacent to FnIII-2. High affinity binding would thus require some movement of the L1-CR module of one monomer towards the bottom of the FnIII-1 domain of the other. Such closure between the two monomers on one side of the dimer may open up space between the equivalent contact sites on the other side as first suggested by De Meyts (De Meyts, 1994). Such a "see-saw" model (FIG. 15) would explain the phenomenon of negative co-operativity and the ability of the IR dimer to bind simultaneously one molecule of insulin with high affinity and a second molecule of insulin with low affinity (Schaffer, 1994). Such a model is also consistent with the observation that a hybrid receptor comprising a normal monomer and a binding defective mutant could still create one normal, high affinity complex, but could not exhibit negative co-operativity (Chakravarty et al., 2005) because the alternate combination of potential ligand binding sites cannot bind ligand because of the mutation. Such arguments remain speculative and high resolution structures of insulin/IR complexes will be required to establish the details of ligand/receptor binding and the domain re-arrangements that accompany signalling.

Example 10

Models for Insulin Binding and Negative Co-operativity

The current view of insulin binding to the IR has been reviewed extensively (Schaffer 1994; De Meyts 1994, 2004; De Meyts & Whittaker 2002) and is as follows. The soluble ectodomain dimer can bind two molecules of insulin, but only with low affinity. It shows linear Scatchard plots and fast dissociation rates which are not accelerated by the presence of unlabelled insulin (does not exhibit negative co-operativity). Isolated half-receptors (IR monomers) are similar and display low-affinity binding, fast dissociation rates and do not exhibit negative co-operativity. In contrast, the membrane-anchored receptor dimer exhibits negative co-operativity and curvilinear Scatchard plots indicating that it binds one insulin molecule with high affinity and a second insulin molecule with low affinity. In the high-affinity state, the insulin molecule makes a bridging contact between the two monomers in the IR dimer.

Schaffer (1994) was the first to propose a cross-linking model for insulin/IR binding that accounted for the ability of one insulin molecule to bridge two distinct sites, Site 1 and Site 2, on the two monomers in the IR dimer as well as for a second and possibly a third insulin molecule to bind with low affinity to the remaining two unoccupied Sites 1 and 2 in the dimer. However, the explanation for the mechanism of negative co-operativity was less convincing and required negative interactions between the bound tracer and the unlabelled insulin at the left-over binding Site 1. The inhibition of accelerated dissociation by high levels of unlabelled insulin was suggested to result from the binding of a third insulin molecule at the left-over Site2 which in effect put a "lid" on the complex.

De Meyts (1994) overcame these latter difficulties simply by recognizing the fact that the IR dimer would have internal symmetry, as subsequently demonstrated (Tulloch et al., 1999), which would allow alternative cross-linking at either of the two sets of α-chain binding sites. In this revised model, Site 1 on each monomer is positioned near the Site 2 of the other. In the high-affinity state one molecule of insulin simultaneously contacts Site 1 of one monomer and Site 2 of the other. Negative co-operativity occurs because high-affinity binding can only occur with either the tracer on one side or the unlabelled insulin on the alternate side of the dimer; .i.e. the ligand/receptor bridging can oscillate from Sites 1 and 2' on one side of the receptor dimer to Sites 1' and 2 on the other side. The 1:2 stoichiometry indicates that two insulin molecules cannot bridge a Site 1-Site 2 pair simultaneously. This model elegantly showed how a second insulin molecule could bind the vacant Site 1 in a high-affinity insulin/IR complex to trigger the alternate bridging associated with negative co-operativity. It also showed how at very high ligand concentrations, a third insulin might bind the left-over Site 2 and thus prevent the switch to the alternate high-affinity configuration given both left-over sites are now occupied and the high affinity state is capped as Schaffer (1994) suggested.

Our data is consistent with the key features of the De Meyts model (De Meyts 1994, 2004; De Meyts & Whittaker 2002) and allow descriptions of the two binding sites to be made. We suggest that Site 1 corresponds to the low-affinity site which controls ligand binding specificity and includes contributions from several distinct regions of the receptor: the L1 domain binding face; the C-terminus of the α-chain (referred to as CT); possibly an additional peripheral portion of the insert region (ID) (Wan et al., 2004), and in the case of IGF binding, the CR region. All of these regions are important for low-affinity ligand-binding to the soluble ectodomain. Our structure, described in Examples 5-9 suggests that Site 2 corresponds to one or more of the AB, CC' and EF loops at the C-terminal end of the first FnIII domain, FnIII-1.

The features of the model are summarized in FIG. 15. We envisage that high-affinity binding is associated with some movement of the L1-CR module of one monomer towards the bottom of the FnIII-1 domain of the other. Such closure between the two monomers on one side of the dimer would open up the space between the equivalent contact sites on the other side, as first suggested by De Meyts (1994). Such a "see-saw" model would explain the phenomenon of negative co-operativity and the ability of the IR dimer to bind simultaneously one molecule of insulin with high affinity and a second molecule of insulin with low affinity (De Meyts 1994; 2004). Such a model is also consistent with the properties of a hybrid IGF-1R dimer comprising a normal monomer disulphide bonded to a monomer with a mutation (in Site 1) that abolishes binding (Chakravarty et al., 2005). This hybrid receptor showed wild-type binding since it could still create one normal, high-affinity binding site with Site 1 from the wild-type monomer and the non-mutated Site 2 of its partner. However, it could not exhibit negative co-operativity (Chakravarty et al., 2005) because the alternate combination of the mutated (defective) Site 1 and wild-type Site 2 is unable to bind ligand and thus is unable to form the alternate high affinity cross-link.

In this model we propose that the classical binding surface of insulin contacts Site 1 on the receptor, while the second binding site of insulin, involving residues from its hexamer forming surface, contacts Site 2. We further propose that the order of binding is Site 1 which induces the known conformational changes at the N-and C-terminal ends of insulin (Wan et al., 2004), followed by Site 2. We base this suggestion on the fact that the insulin residues involved in binding to our suggested Site 1 are equally important for low-affinity binding to soluble ectodomain and to half-receptors, whereas mutations in the residues in the hexamer face selectively impair only the formation of the high-affinity state and signaling. This is opposite to the order suggested by De Meyts (De Meyts 1994; 2004).

The disclosure of all publications referred to in this application are incorporated herein by reference.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

Accili, D., Mosthaf, L., Ullrich, A. & Taylor, S. I. (1991). A mutation in the extracellular domain of the insulin receptor impairs the ability of insulin to stimulate receptor autophosphorylation, J. Biol. Chem., 266, 434-439.

Adams, T. E., Epa, V. C., Garrett, T. P. J. & Ward, C. W. (2000). Structure and function of the type 1 insulin-like growth factor receptor, Cell. Molec. Life Sci., 57, 1050-1093.

Andersen, A. S., Kjeldsen, T., Wiberg, F. C., Vissing, H., Schaffer, L., Rasmussen, J. S., De-Meyts, P. & Moller, N. P. H. (1992). Identification of determinants that confer ligand specificity on the insulin receptor, J. Biol. Chem., 267, 13681-13686.

Apfel, S. C. (1999). Neurotrophic factors in the therapy of diabetic neuropathy, Am. J. Med., 107, 34S-42S.

Auer, R. N. (1998). Insulin, blood glucose levels, and ischemic brain damage. Neurology, 51, S39-S43.

Ausubel et al. (1999). Short Protocols in Molecular Biology, 4th Ed, John Wiley & Sons, Inc.; and the full version entitled Current Protocols in Molecular Biology.

Bailyes, E. M., Nave, B. T., Soos, M. A., Orr, S. R., Hayward, A. C. & Siddle, K. (1997). Insulin receptor/IGF-I receptor hybrids are widely distributed in mammalian tissues: quantification of individual receptor species by selective immunoprecipitation and immunoblotting, Biochem. J., 327, 209-215.

Bajaj, M., Waterfield, M. D., Schlessinger, J., Taylor, W. R. & Blundell, T. (1987). On the tertiary structure of the extracellular domains of the epidermal growth factor and insulin receptors, Biochim. Biophys. Acta, 916, 220-226.

Bartlett et al., (1989). CAVEAT: A Program to Facilitate the Structure-Derived Design of Biologically Active Molecules, in Molecular Recognition in Chemical and Biological Problems, Special Pub., Royal Chem. Soc., 78, 182-196.

Bayne, M. L., Applebaum, J., Chicchi, G. G., Hayes, N. S., Green, B. G. & Cascieri, M. A. (1988). Structural analogs of human insulin-like growth factor I with reduced affinity for serum binding proteins and the type 2 insulin-like growth factor receptor, J. Biol. Chem., 263, 6233-6239.

Bebbington, C. R. & Hentschel, C. C. G. (1987). The use of vector based on gene amplification for the expression of cloned genes in mammalian cells, in DNA Cloning, ed. Glover, D. M., Academic Press, San Diego. Vol 3, p163.

Bentley, G. A. (1997). Phased translation function, Meth. Enzym., 276, 611-619.

Binz, H. K., Amstutz, P. & Pluckthun, A. (2005). Engineering novel binding proteins from nonimmunoglobulin domains, Nature Biotechnology, 23, 1257-1268.

Blanc, E., Roversi, P., Vonrhein, C., Flensburg, C., Lea, S. M. & Bricogne, G. (2004). Refinement of severely incomplete structures with maximum likelihood in BUSTER-TNT, Acta Crystallogr. D. Biol. Crystallogr., 60, 2210-2221.

Blondelle, S. E. & Houghten, R. A. (1996). Novel antimicrobial compounds identified using synthetic combinatorial library technology, Trends Biotechnol., 14, 60-65. Bohm & Stahl (1999). M. Med. Chem. Res., 9, 445.

Bohne-Lang, A. & von der Leith, C. W. (2005). GlyProt: in silico glycosylation of proteins. Nucl. Acids Res. 33, W214-219.

Brandt, J., Andersen, A. S. & Kristensen, C. (2001). Dimeric fragment of the insulin receptor alpha-subunit finds insulin with full holoreceptor affinitym, J. Biol. Chem., 276, 12378-12384.

Bricogne, G. (1997). Bayesian statistical viewpoint on structure determination: basic concepts and examples, Methods Enzymol., 276, 361-423.

Brooks, B. R., Bruccoleri, R. E., Olafson, B. D., States, D. J., Swaminathan, S. & Karplus, J. M. (1983). Comp. Chem., 4, 187-217.

Brunger, A. T. (1996). X-PLOR reference manual 3.851 (Yale Univ., New Haven, Conn.).

Brunger, A. T., Adams, P. D., Clore, G. M., DeLano, W. L., Gros, P., Grosse-Kunstleve, R. W., Jiang, J. S., Kuszewski, J., Nilges, M., Pannu, N. S., Read, R. J., Rice, L. M., Simonson, T. & Warren, G. L. (1998). Crystallography and NMR system: A new software suite for macromolecular structure determination, Acta Crystallogr. D. Biol. Crystallogr., 54, 905-921.

Brunger (1997). Meth. Enzym., 276, 558-580.

Burgess & Leach (1973a). Biopolymers, 12(12), 2691-2712.
Burgess & Leach (1973b). Biopolymers, 12(11), 599-2605.
Burgess, A. W., Cho, H—S., Eigenbrot, C., Ferguson, K. M., Garrett, T. P. J., Leahy, D. J., Lemmon, M. A., Sliwkowski, M. X., Ward, C. W. & Yokoyama, S. (2003). An open-and-shut case? Recent insights into the activation of EGF/ErbB receptors, Molecular Cell, 12, 541-552.
Buttel et al. (1999). Immunol. Cell Biol., 77, 256-262.
Carell et al. (1994a). Angew. Chem. Int. Ed. Engl., 33, 2059.
Carell et al. (1994b). Angew. Chem. Int. Ed. Engl., 33, 2061.
Chakravarty, A.; Hinrichsen, J.; Whittaker, L. & Whittaker, J. (2005). Rescue of ligand binding of a mutant IGF-I receptor by complementation, Biochem. Biophys. Res. Commun., 331, 74-77.
Chan, S. J., et al. (2007). Complementation Analysis Demonstrates That Insulin Cross-links Both α-Subunits in a Truncated Insulin Receptor Dimer. J. Biol. Chem. 282: 13754-13758.
Cho et al. (1993). Science, 261, 1303.
Chow et al. (1998). Biol. Chem., 273, 4672-4680.
Clarke et al. (2000). Cancer Res., 60, 4804-4811.
Cohen et al. (1990). Molecular Modeling Software and Methods for Medicinal Chemistry, J. Med. Chem., 33, 883-894.
Cowtan, K. D. (1994). 'dm': An automated procedure for phase improvement by density modification, Joint CCP4 and ESF-EACBM newsletter on protein crystallography 31, 9-14.
Cull et al. (1992). Proc. Natl. Acad. Sci. USA, 89, 1865-1869.
Cwirla et al. (1990). Proc. Natl. Acad. Sci. USA, 97, 6378-6382.
de la Fortelle, E. & Bricogne, G. (1997). Maximum-likelihood heavy-atom parameter refinement for multiple isomorphous replacement and multiwavelength anomalous diffraction methods, Methods Enzymol., 276, 472-494.
De Meyts, P., Gu, J-L., Shymko, R. M., Kaplan, B. E., Bell, G. I. & Whittaker, J. (1990). Identification of a ligand-binding region of the human insulin receptor encoded by the second exon of the gene, Molecular Endocrinol., 4, 409-416.
De Meyts, P. (1994). The structural basis of insulin and IGF-1 Receptor binding and negative co-operativity, and its relevance to mitogenic versus metabolic signaling, Diabetologia, 37 (Suppl 2), S135-S148.
De Meyts, P. & Whittaker, J. (2002). Structural biology of insulin and IGF 1 receptors: implications for drug design, Nat. Rev. Drug Discov., 1, 769-783.
De Meyts, P. (2004). Insulin and its receptor: structure, function and evolution, Bioessays, 26, 1351-1362.
DeWitt et al. (1993). Proc. Natl. Acad. Sci. USA, 90, 6909.
Denley, A., Wallace, J. C., Cosgrove, L. J. & Forbes, B. E. (2003). The insulin receptor isoform exon 11-(IR-A) in cancer and other diseases: a review, Horm. Metab. Res., 35, 778-785.
Denley, A., Bonython, E. R., Booker, G. W., Cosgrove, L. J., Forbes, B. E., Ward, C. W. & Wallace, J. C. (2004). Structural determinants for high-affinity binding of insulin-like growth factor II to insulin receptor (1R)-A, the exon 11 minus isoform of the IR, Mol. Endocrinol., 18, 2502-2512.
Derewenda, U., Derewenda, Z., Dodson, E. J., Dodson, G. G., Bing, X. & Markussen, J. (1991). X-ray analysis of the single chain B29-A1 peptide-linked insulin molecule. A completely inactive analogue, J. Mol. Biol., 220, 425-433.
Devlin (1990). Science, 249, 404-406.
Emsley, P. & Cowtan, K. (2004). Coot: model-building tools for molecular graphics, Acta Crystallographica, Section D-Biological Crystallography, 60, 2126-2132.
Erb et al. (1994). Proc. Natl. Acad. Sci. USA, 91, 11422.
Evan, G. I.; Lewis, G. K.; Ramsay, G. & Bishop, J. M. (1985). Isolation of monoclonal antibodies specific for human c-myc proto-oncogene product, Mol. Cell. Biol., 5, 3610-3616.
Ewing et al. (2001). J. Comput-Aid. Mol. Design, 15, 411.
Fabry, M., Schaefer, E., Ellis, L., Kojro, E., Fahrenholz, F. & Brandenburg, D. (1992). Detection of a new hormone contact site within the insulin receptor ectodomain by the use of a novel photoreactive insulin, J. Biol. Chem., 267, 8950-8956.
Felici (1991). J. Mol. Biol., 222, 301-310.
Florke, R. R., Schnaith, K., Passlack, W., Wichert, M., Kuehn, L., Fabry, M., Federwisch, M. & Reinauer, H. (2001). Hormone-triggered conformational changes within the insulin-receptor ectodomain: requirement for transmembrane anchors. Biochem. J., 360, 189-198.
Fodor (1993). Nature, 364, 555-556.
Frank et al. (1999). J. Struct. Biol., 116, 190-199.
Garrett, T. P. J., McKern N. M., Lou M., Frenkel M. J., Bentley J. D., Lovrecz G. O., Elleman T. C., Cosgrove L. J. & Ward C. W. (1998). Crystal structure of the first three domains of the type-1 insulin-like growth factor receptor, Nature, 394, 395-399.
Gallop et al. (1994). J. Med. Chem., 37, 1233.
Gilliland, L. K., Norris, N. A., Marquardt, H., Tsu, T. T., Hayden, M. S., Neubauer, M. G., Yelton, D. E., Mittler, R. S. & Ledbetter, J. A. (1996). Rapid and reliable cloning of antibody variable regions and generation of recombinant single chain antibody fragments, Tissue Antigens, 47, 1-20.
Goodford, P. J. (1985). A Computational Procedure for Determining Energetically Favorable Binding Sites on Biologically Important Macromolecules, J. Med. Chem., 28, 849-857 (1985).
Goodsell, D. S. & Olsen, A. J. (1990). Automated Docking of Substrates to Proteins by Simulated Annealing, Proteins: Structure, Function, and Genetics, 8, 195-202.
Gronskov, K., Vissing, H., Shymko, R. M., Tornqvist, H. & De Meyts, P. (1993). Mutation of arginine 86 to proline in the insulin receptor alpha subunit causes lack of transport of the receptor to the plasma membrane, loss of binding affinity and a constitutively activated tyrosine kinase in transfected cells, Biochem. Biophys. Res. Commun., 192, 905-911.
Guida, W. C. (1994). Software For Structure-Based Drug Design, Curr. Opin. Struct. Biology, 4, 777-781.
Gustafson, T. A. & Rutter, W. J. (1990). The cysteine-rich domains of the insulin and insulin-like growth factor I receptors are primary determinants of hormone binding specificity, J. Biol. Chem., 265, 18663-18667.
Harlow & Lane (1988). Antibodies: A Laboratory Manual, Cold Spring Harbor Laboratory, New York.
Houghten et al. (1991). Nature, 354, 84-86.
Houghten (1992). Biotechniques, 13, 412-421.
Hoyne, P. A., Elleman, T. C., Adams, T. E., Richards, K. M. & Ward, C. W. (2000). High affinity insulin binding by soluble insulin receptor extracellular domain fused to a leucine zipper, FEBS Letters, 479, 15-18.
Hruby et al. (1992). Applications of Synthetic Peptides, in Synthetic Peptides: A User's Guide, 259-345, W. H. Freeman & Co.
Hua, Q. X., Shoelson, S. E., Kochoyan, M. & Weiss, M. A. (1991). Receptor binding redefined by a structural switch in a mutant human insulin, Nature, 354, 238-241.
Huang, K., Xu, B., Hu, S. Q., Chu, Y. C., Hua, Q. X., Qu, Y., L1, B., Wang, S., Wang, R. Y., Nakagawa, S. H., Theede, A. M., Whittaker, J., De Meyts, P., Katsoyannis, P. G. &

Weiss, M. A. (2004). How insulin binds: the B-chain alpha-helix contacts the L1 beta-helix of the insulin receptor, J. Mol. Biol., 341, 529-550.

Jancarik, J. & Kim, S.-H. (1991). Sparse matrix sampling: a screening method for crystallization of proteins, J. Appl. Cryst., 24, 409-411.

Jones, T. A., Zou, J. Y., Cowan, S. W. & Kjeldgaard (1991). Improved methods for finding protein models in electron density maps and the location of errors in these models, Acta Crystallogr., A 47, 110-119.

Kadowaki, H., Kadowaki, T., Cama, A., Marcus-Samuels, B., Rovira, A., Bevins, C. L. & Taylor, S. I. (1990). Mutagenesis of Lysine 460 in the human insulin receptor: effects upon receptor recycling and cooperative interactions among binding sites, J. Biol. Chem., 265, 21285-21296.

Kitamura, T., Kahn, C. R. & Accili, D. (2003). Insulin receptor knockout mice. Annu Rev Physiol., 65, 313-332.

Kjeldsen, T., Andersen A. S., Wiberg F. C., Rasmussen J. S., Schaffer L., Balschmidt P., Moller, K. B. & Moller N. P. (1991). The ligand specificities of the insulin receptor and the insulin-like growth factor I receptor reside in different regions of a common binding site, Proc. Natl. Acad. Sci. USA, 88, 4404-4408.

Kjeldsen T., Wiberg F. C. & Andersen A. S. (1994). Chimeric receptors indicate that phenylalanine 29 is a major contributor to insulin specificity of the insulin receptor, J. Biol. Chem., 269, 32942-32946.

Kleywegt, G. J. & Jones, T. A. (1994). A super position. CCP4/ESF-EACBM, Newsletter on Protein Crystallography, 31, 9-14.

Kobayashi, M., Takata, Y., Ishibashi, O., Sasaoka, T., Iwasaki, T. M., Shigeta, Y. & Inouye, K. (1986). Receptor binding and negative cooperativity of a mutant insulin, Biochem. Biophys. Res. Commun., 137, 250-257.

Kristensen, C., Kjeldsen, T., Wiberg, F. C., Schaffer, L., Hach, M., Havelund, S., Bass, J., Steiner, D. F. & Andersen, A. S. (1997). Alanine scanning mutagenesis of insulin, J. Biol. Chem., 272, 12978-12983.

Kristensen, C., Wiberg, F. C. & Andersen, A. S. (1999). Specificity of insulin and insulin-like growth factor I receptors investigated using chimeric mini-receptors—Role of C-teriminal of receptor alpha subunit, J. Biol. Chem., 274, 37351-37356.

Kristensen, C., Wiberg, F. C., Schaffer, L. & Andersen, A. S. (1998). Expression and characterization of a 70-kDa fragment of the insulin receptor that binds insulin, J. Biol. Chem., 273, 17780-17786.

Kuntz, I. D., Blaney, J. M., Oatley, S. J., Langridge, R. & Ferrin, T. E. (1982). A Geometric Approach to Macromolecule-Ligand Interactions, J. Mol. Biol., 161, 269-288.

Kurose, T., Pashmforoush, M., Yoshima, Y., Carroll, R., Schwartz, G. P., Burke, G. T., Katsoyannis, P. G. & Steiner, D. F. (1994). Cross-linking of a B25 azidophenylalanine insulin derivative to the carboxy-terminal region of the alpha-subunit of the insulin receptor. Identification of a new insulin-binding domain in the insulin receptor, J. Biol. Chem., 269, 29190-29197.

Jones, T. A., Zou, J. Y., Cowan, S. W. & Kjeldgaard (1991). Improved methods for binding protein models in electron density maps and the location of errors in these models, Acta Crystallogr. A., 47, 110-119.

Laemmli, U. K. (1970). Cleavage of structural proteins during the assembly of the head of bacteriophage T4, Nature, 227, 680-685.

Ladner: U.S. Pat. No. 5,223,409

Lam et al. (1991). Nature, 354, 82-84.

Lam, K. S. (1997). Anticancer Drug Des., 12, 145. Lattman (1985). Use of the Rotation and Translation Functions, Meth. Enzymol., 115, 55-77.

Lee, J., Pilch, P. F., Shoelson, S. E. & Scarlata, S. F. (1997). Conformational changes of the insulin receptor upon insulin binding and activation as monitored by fluorescence spectroscopy, Biochemistry, 36, 2701-2708.

Liu J. P., Baker, J., Perkins, A. S., Robertson, E. J., & Efstratiadis, A. (1993). Mice carrying null mutations of the genes encoding insulin-like growth factor I (Igf-1) and type 1 IGF receptor (Igflr), Cell, 75, 59-72.

Ludvigsen, S., Olsen, H. B. & Kaarsholm, N. C. (1998). A structural switch in a mutant insulin exposes key residues for receptor binding, J. Mol. Biol., 279, 1-7.

Luo, R. Z. T., Beniac, D. R., Fernandes, A., Yip, C. C. & Ottensmeyer, F. P. (1999). Quaternary structure of the insulin-insulin receptor complex, Science, 285, 1077-1080.

Lütteke, T, Frank, M. & von der Leith, C. W. (2005). Carbohydrate Structure Suite (CSS): analysis of carbohydrate 3D structures derived from the PDB.

Lütteke, T., Bohne-Lang, A., Loss, A., Goetz, T., Frank, M. & von der Lieth, C. W. (2006). Glycosciences de: an Internet portal to support glycomics and glycobiology research. Glycobiology 16, 71R-81R.

Marino-Buslje, C., Mizuguchi, K., Siddle, K. & Blundell, T. L. (1998). A third fibronectin type III domain in the extracellular region of the insulin receptor family, FEBS Lett., 441, 331-336.

Marino-Buslje, C., Martin-Martinez, M., Mizuguchi, K., Siddle, K. & Blundell, T. L. (1999). The insulin receptor: from protein sequence to structure, Biochem. Soc. Trans., 27, 715-726.

Marsh B. J., Alm R. A., McIntosh S. R. & James D. E. (1995). Molecular regulation of GLUT-4 targeting in 3T3-L1 adipocytes, J. Cell Biol., 130, 1081-1091.

Martin (1992). 3D Database Searching in Drug Design, J. Med. Chem., 35, 2145-2154.

McCoy, A. J., Grosse-Kunstleve, R. W., Storoni, L. C. & Read, R. J. (2005). Likelihood-enhanced fast translation functions, Acta Crystallogr. D. Biol. Crystallogr., 61, 458-464.

McKern, N. M., Lou, M., Frenkel, M. J., Verkuylen, A., Bentley, J. D., Lovrecz, G. O., Ivancic, N., Elleman, T. C., Garrett, T. P. J., Cosgrove L. & Ward, C. W. (1997). Crystallization of the first three domains of the human insulin-like growth factor-1 receptor, Protein Sci., 6, 2663-2666.

McRee, D. E. (1999). XtalView/Xfit—a versatile program for manipulating atomic coordinates and electron density, J. Struct. Biol., 125, 156-165.

Miranker, A. & Karplus, M. (1991). Functionality Maps of Binding Sites: A Multiple Copy Simultaneous Search Method, Proteins: Structure, Function and Genetics, 11, 29-34.

Moody et al. (1974). Horm. Metab. Res., 6(1), 12-6.

Morton T. A. & Myszka, D. G. (1998). Kinetic analysis of macromolecular interactions using surface plasmon resonance biosensors, Methods Enzymol., 295, 268-294.

Mulhern, T. D., Booker, G. W. & Cosgrove, L. (1998). A third fibronectin type-III domain in the insulin-family receptors, TIBS, 23, 465-466.

Murshudov, G. N., Vagin, A. A. & Dodson, E. J. (1997). Refinement of Macromolecular Structures by the Maximum-Likelihood, Method Acta Cryst., D53, 240-255.

Mynarcik, D. C., Yu, G. Q. & Whittaker, J. (1996). Alanine-scanning mutagenesis of a C-terminal ligand binding domain of the insulin receptor alpha subunit., J. Biol. Chem., 271, 2439-2442.

Mynarcik, D. C., Williams, P. F., Schaffer, L., Yu, G. Q. & Whittaker, J. (1997a). Analog binding properties of insulin receptor mutants—identification of amino acids interacting with the COOH terminus of the B-chain of the insulin molecule, J. Biol. Chem., 272, 2077-2081.

Mynarcik, D. C., Williams, P. F., Schaffer, L., Yu, G. Q. & Whittaker, J. (1997b). Identification of common ligand binding determinants of the insulin and insulin-like growth factor 1 receptors—insights into mechanisms of ligand binding, J. Biol. Chem., 272, 18650-18655.

Nakae, J., Morioka, H., Ohtsuka, E. & Fujieda, K. (1995). Replacements of leucine 87 in human insulin receptor alter affinity for insulin, J. Biol. Chem., 270, 22017-22022.

Nakagawa, S. H. & Tager, H. S. (1989). Perturbation of insulin-receptor interactions by intramolecular hormone cross-linking. Analysis of relative movement among residues A1, B1 and B29, J. Biol. Chem., 264, 272-279.

Nakagawa, S. H. & Tager, H. S. (1992). Importance of aliphatic side-chain structure at positions 2 and 3 of the insulin A chain in insulin-receptor interactions, Biochemistry, 31, 3204-3214.

Nakagawa, S. H., Tager, H. S. & Steiner, D. F. (2000) Mutational analysis of invariant valine B12 in insulin: Implications for binding. Biochemistry 39, 15826-15835.

Nice, E. C. & Catimel, B. (1999). Instrumental biosensors: new perspectives for the analysis of biomolecular interactions, Bioessays, 21, 339-352.

Nicholls, A., Sharp, K. & Honig, B. (1991). Protein Folding and Association: Insights from the Interfacial and thermodynamic properties of hydrocarbons, Proteins: Struct. Funct. Genet., 11, 281-295.

Navia & Murcko (1992). The Use of Structural Information in Drug Design, Curr. Opin. Struct. Biol., 2, 202-210.

Navaza & Saludjian (1997). Meth. Enzym., 276, 581-594.

O'Bryan, J. P., Frye, R. A., Cogswell, P. C., Neubauer, Z., Kitch, B., Prokop, C., Espinosa III, R., Le Beau, M. M., Earp, H. S. & Liu, E. T. (1991). Axl, a transforming gene isolated from primary human myeloid leukemia cells, encodes a novel receptor tyrosine kinase, Molec. Cell. Biol., 11, 5016-5031.

O'Donohue et al. (1995). Protein Sci., 4(10), 2191-2202).

Olefsky J. M. (1978). Mechanisms of the ability of insulin to activate the glucose-transport system in rat adipocytes, Biochem. 1, 172, 137-145.

Ottensmeyer, F. P., Beniac, D. R., Luo, R. Z. T. & Yip, C. C. (2000). Mechanism of transmembrane signaling: Insulin binding and the insulin receptor, Biochemistry, 39, 12103-12112.

Ottensmeyer, F. P., Beniac, D. R., Luo, R. Z. T. & Yip, C. C. (2001). Mechanism of transmembrane signaling: Insulin binding and the insulin receptor, Biochemistry, 40, 6988-6988.

Otwinowski, Z. & Minor, W. (1997). Processing of X-ray diffraction data collected in oscillation mode. Methods Enzymol., 276, 307-326.

Peng, K., Vucetic, S., Radivojac, P., Brown, C I, Dunker, A. K. & Obradovic, Z. (2005). Optimizing long intrinsic disorder predictors with protein evolutionary information, J. Bioinformatics Comput. Biol., 3, 35-60.

Pflugrath, J. W. (1999). The finer things in X-ray diffraction data collection, Acta Crystallogr. D. Biol. Crystallogr., 55, 1718-1725.

Pillutla, R. C., Hsiao, K. C., Beasley, J. R., Brandt, J., Ostergaard, S., Hansen, P. H., Spetzler, J. C., Danielsen, G. M., Andersen, A. S., Brissette, R. E., Lennick, M., Fletcher, P. W., Blume, A. J., Schaffer, L. & Goldstein, N. I. (2002). Peptides identify the critical hotspots involved in the biological activation of the insulin receptor, J. Biol. Chem., 277, 22590-22594.

Pitt, J. J. & Gorman, J. J. (1996.) Matrix-assisted laser desorption/ionization time-of-flight mass spectrometry of sialylated glycopeptides and proteins using 2,6-dihydroxyacetophenone as a matrix, Rapid Commun. Mass Spectrom., 10, 1786-1788.

Pitt, J. J. & Gorman, J. J. (1997). Oligosaccharide characterization and quantitation using 1-phenyl-3-methyl-5-pyrazolone derivatization and matrix-assisted laser desorption/ionization time-of-flight mass spectrometry, Anal Biochem., 248, 63-75.

Prigent, S. A., Stanley, K. K. & Siddle, K. (1990). Identification of epitopes on the human insulin receptor reacting with rabbit polyclonal antisera and mouse monoclonal antibodies, J. Biol. Chem., 265, 9970-9977.

Pullen, R. A., Lindsay, D. G., Wood, S. P., Tickle, I. J., Blundell, T. L., Wollmer, A., Krail, G., Brandenburg, D., Zahn, H., Gliemann. J. & Gammeltoft, S. (1976). Receptor binding region of insulin, Nature, 259, 369-373.

Rarey, M. et al. (1996). J. Mol. Biol., 261, 470.

Robinson, L. J. & James, D. E. (1992). Insulin-regulated sorting of glucose transporters in 3T3-L1 adipocytes, Am. J. Physiol., 263, E383-E393

Rossmann, ed. (1972). The Molecular Replacement Method, Int. Sci. Rev. Ser., No. 13, Gordon & Breach, New York.

Rouard, M., Bass, J., Grigorescu, F., Garrett, T. P. J., Ward, C. W., Lipkind, G., Jaffiole, C., Steiner, D. F. & Bell, G. I. (1999). Congenital insulin resistance associated with a conformational alteration in a conserved beta-sheet in the insulin receptor L1 domain, J. Biol. Chem., 274, 18487-18491.

Sall and Blundell (1993). J. Mol. Biol., 234, 779-815.

Sambrook et al. (2001). Molecular Cloning: A Laboratory Manual, 3$^{rd}$ ed. Cold Spring Harbor Laboratory Press, Cold Spring Harbor, N.Y.

Schaefer, E. M., Erickson, H. P., Federwisch, M., Wollmer, A. & Ellis, L. (1992). Structural organization of the human insulin receptor ectodomain, J. Biol. Chem., 267, 23393-23402.

Schaffer L. (1994). A model for insulin binding to the insulin receptor, Eur. J. Biochem., 221, 1127-1132.

Schaffer, L., Brissette, R. E., Spetzler, J. C., Pillutla, R. C., Ostergaard, S., Lennick, M., Brandt, J., Fletcher, P. W., Danielsen, G. M., Hsiao, K. C., Andersen, A. S., Dedova, O., Ribel, U., Hoeg-Jensen, T., Hansen, P. H., Blume, A. J., Markussen, J. & Goldstein, N. I. (2003). Assembly of high-affinity insulin receptor agonists and antagonists from peptide building blocks, Proc. Natl. Acad. Sci. USA, 100, 4435-4439.

Schaefer E. M., Siddle K. & Ellis L. (1990). Deletion analysis of the human insulin receptor ectodomain reveals independently folded soluble subdomains and insulin binding by a monomeric A-subunit, J. Biol. Chem., 265, 13248-13253.

Schlehuber, S. & Skerra, A. (2005). Lipocalins in drug discovery: from natural ligand-binding proteins to anticalins', Drug Disc. Today, 10, 23-33.

Schumacher, R., Mosthaf, L., Schlessinger, J., Brandenburg, D. & Ullrich, A. (1991). Insulin and insulin-like growth factor-1 binding specificity is determined by distinct regions of their cognate receptors, J. Biol. Chem. 266, 19288-19295.

Schumacher, R., Soos, M. A., Schlessinger, J., Brandenburg, D., Siddle, K. & Ullrich, A. (1993). A. Signaling-competent receptor chimeras allow mapping of major insulin receptor binding domain determinants., J. Biol. Chem., 268, 1087-1094.

Scott & Smith (1990). Science, 249, 386-390.

Silverman, J., Liu, Q., Bakker, A., To, W., Duguay, A., Alba, B. M., Smith, R., Rivas, A., L1, P., Le, H., Whitehorn, E., Moore, K. W., Swimmer, C., Perlroth, V., Vogt, M., Kolkman, J. & Stemmer, W. P. (2005) Multivalent avimer proteins evolved by exon shuffling of a family of human receptor domains. Nature Biotechnology 23, 1556-1561.

Sitkoff, D., Lockhart, D. J., Sharp, K. A. & Honig, B. (1994). Calculation of electrostatic effects at the amino terminus of an alpha helix, Biophys. J., 67, 2251-2260.

Smith et al. (1999). Nat. Med., 5, 1390-1395.

Songyang et al. (1993). Cell, 72, 767-778.

Soos, M. A., Siddle, K., Baron, M. D., Heward, J. M., Luzio, J. P., Bellatin, J. & Lennox, E. S. (1986). Monoclonal antibodies reacting with multiple epitopes on the human insulin receptor, Biochem. J., 235, 199-208.

Sparrow, L. G., McKern, N. M., Gorman, J. J., Strike, P. M., Robinson, C. P., Bentley, J. D. & Ward, C. W. (1997). The disulfide bonds in the C-terminal domains of the human insulin receptor ectodomain, J. Biol. Chem., 272, 29460-29467.

Sparrow, L. G., Gorman, J. J., Strike, P. M., Robinson, C. P., McKern, N. M., Epa, V. C., & Ward, C. W. (2006). The location and characterisation of the O-linked glycans of the human insulin receptor, Protein Sci., Submitted.

Spellman, M. W., Basa, L. J., Leonard, C. K., Chakel, J. A., O'Connor, J. V., Wilson, S. & van Halbeek, H. (1989). Carbohydrate structures of human tissue plasminogen activator expressed in Chinese hamster ovary cells, J. Biol. Chem., 264, 14100-14111.

Stanley, P. (1989). Chinese hamster ovary cell mutants with multiple glycosylation defects for the production of glycoproteins with minimal carbohydrate heterogeneity, Molec. Cellul. Biol., 9, 377-383.

Surinya, K. H., Molina, L., Soos, M. A., Brandt, J., Kristensen, C. & Siddle, K. (2002). Role of insulin receptor dimerization domains in ligand binding, cooperativity, and modulation by anti-receptor antibodies, J. Biol. Chem., 277, 16718-16725.

Rossmann, (1972) ed., "The Molecular Replacement Method", Int. Sci. Rev. Ser., No. 13, Gordon & Breach, New York.

Taylor, S. I., Wertheimer, E., Accili, D., Cama, A., Hone, J., Roach, P., Quon, M. J., Suzuki, Y., Levy-Toledano, R., Taouis, M., Sierra, M de la S., Barbetti, F, & Gorden P. (1994). Mutations in the insulin receptor gene:update Endocrine Reviews. 2, 58-65.

Terwilliger, T. C. (2000) Maximum-likelihood density modification. Acta Crystallogr D Biol Crystallogr 56, 965-972.

Tong and Rossmann, (1997) Meth. Enzym., vol. 276, pp. 594-611,

Tulloch, P. A., Lawrence, L. J., Mckern, N. M., Robinson, C. P., Bentley, J. D., Cosgrove, L., Ivancic, N., Lovrecz, G. 0., Siddle, K., and Ward, C. W. (1999) Single-molecule imaging of human insulin receptor ectodomain and its Fab complexes. J. Struct. Biol. 125, 11-18.

Ullrich, A., Bell, J. R., Chen, E. Y., Herrera, R., Petruzzelli, L. M., Dull, T. J., Gray, A., Coussens, L., Liao, Y.-C., Tsubokawa, Mason, A., Seeburg, P. H., Grunfeld, C., Rosen, O. M. & Ramachandran, J. (1985). Human insulin receptor and its relationship to the tyrosine kinase family of oncogenes. Nature 313, 756-761

Ullrich, A., Gray, A., Tam, A. W., Yang-Feng, T., Tsubokawa, M., Collins, C., Henzel W., Le Bon, T., Kathuria, S., Chen, E., Jacobs, S., Francke, U., Ramachandran, J. & Fujita-Yamaguchi, Y. (1986). Insulin-like growth factor 1 receptor primary structure: comparison with insulin receptor suggests structural determinants that define functional specificity. EMBO J. 5, 2503-2512

Ulrich, H. (2006) RNA aptamers: from basic science towards therapy. Handb Exp Pharmacol. Issue 173, 305-326.

van der Vorm, E. R., Kuipers, A., Kielkopfrenner, S., Krans, H. M. J., Moller, W. & Maassen, J. A. 1994, A mutation in the insulin receptor that impairs proreceptor processing but not insulin binding. J. Biol. Chem. 269, 14297-14302

Wada, A., Yokoo, H., Yanagita, T. & Kobayashi, H. (2005). New twist on neuronal insulin receptor signaling in health, disease, and therapeutics. J Pharmacol Sci. 99, 128-143.

Wan Z., Xu, B., Huang, K., Chu, Y. C., L1, B., Nakagawa, S. H., Qu, Y., Hu, S. Q., Katsoyannis, P. G., & Weiss, M. A. (2004) Enhancing the activity of insulin at the receptor interface: crystal structure and photo-cross-linking of A8 analogues. Biochemistry. 2004; 43(51): 16119-33.

Wan, Z. L., Huang, K., Xu, B., Hu, S. Q., Wang, S., Chu, Y. C., Katsoyannis, P. G. & Weiss, M. A. (2005). Diabetes-associated mutations in human insulin: crystal structure and photo-cross-linking studies of A-chain variant insulin Wakayama. Biochemistry 44, 5000-5016.

Ward, C. W., Hoyne, P. A. & Flegg, R. H. (1995). Insulin and epidermal growth factor receptors contain the cysteine repeat motif found in the tumor necrosis factor receptor. Proteins: Struct. Funct. Genet., 22, 141-153.

Ward, C. W. (1999). Members of the insulin receptor family contain three fibronectin type III domains. Growth Factors, 16, 315-322.

Ward, C. W. & Garrett, T. P. J. (2001). The relationship between the L1 and L2 domains of the insulin and epidermal growth factor receptors and leucine-rich repeat modules, BMC Bioinformatics 2:4 on the world-wide web at address biomedcentral.com/473-2105/2/4).

Ward, C. W., Garrett, T. P. J., Lou, M., McKern, N. M., Adams, T. E., Elleman, T. C., Hoyne, P. A., Frenkel, M. J., Cosgrove, L. J., Lovrecz, G. O., Sparrow, L. G., Lawrence, L. J. & Epa, V. C. (2003). The structure of the type-I insulin like growth factor receptor, in Insulin-like growth factors (LeRoith D, Zumkeller, W. & Baxter R. (eds), Eurekah-.com and Kluwer Academic/Plenum Publishers, 1-21.

Wedekind, F., Baer-Pontzen, K., Bala-Mohan, S., Choli, D., Zahn, H. & Brandenburg, D. (1989). Hormone binding site of the insulin receptor: analysis using photoaffinity-mediated avidin complexing, Biol. Chem. Hoppe Seyler, 370, 251-258.

Weiner, S. J., Kollman, P. A., Case, D. A., Singh, U. C., Ghio, C., Alagona, G. & Weiner, P. (1984). J. Am. Chem. Soc., 106, 765-784.

Whittaker, J., Garcia, P., Yu, G. Q. & Mynarcik, D. C. (1994). Transmembrane domain interactions are necessary for negative cooperativity of the insulin receptor, Mol. Endocrinol., 8, 1521-1527.

Whittaker, J., Groth, A. V., Mynarcik, D. C., Pluzek, L., Gadsboll, V. L. & Whittaker, L. J. (2001). Alanine scanning mutagenesis of a type 1 insulin-like growth factor receptor ligand binding site, J. Biol. Chem., 276, 43980-43986.

Whittaker, J., Sorensen, H., Gadsboll, V. & Hinrichsen, J. (2002). Comparison of the functional insulin binding epitopes of the A and β isoforms of the insulin receptor, J. Biol. Chem., 277, 47380-47384.

Williams, P. F., Mynarcik, D. C., Yu, G. Q. & Whittaker, J. (1995). Mapping of an NH2-terminal ligand binding site of the insulin receptor by alanine scanning mutagenesis, J. Biol. Chem., 270, 3012-3016.

Wood & Wetzel (1992). Int. J. Peptide Protein Res., 39, 533-39.

Xu, B., Hua, Q., Nakagawa, S. H., Jia, W., Chu, Y-C, Katsoyannis, P. G. & Weiss, M. A. (2002). Chiral Mutagenesis of insulin's hidden receptor-binding surface: Structure of an allo-isoleucine[42] analogue, J. Mol. Biol., 316, 435-441.

Xu, B., Hu, S. Q., Chu, Y. C., Huang, K., Nakagawa, S. H., Whittaker, J., Katsoyannis, P. G. & Weiss, M. A. (2004). Diabetes-associated mutations in insulin: consecutive residues in the B chain contact distinct domains of the insulin receptor, Biochemistry, 43(26), 8356-72.

Yip, C. C., Hsu, H., Patel, R. G., Hawley, D. M., Maddux, B. A. & Goldfine, I. D. (1988). Localization of the insulin-binding site to the cysteine-rich region of the insulin receptor alpha-subunit, Biochem. Biophys. Res. Commun., 157, 321-329.

Yip, C. C. & Ottensmeyer, P. (2003). Three-dimensional structural interactions of insulin and its receptor, J. Biol. Chem., 278, 27329-27332.

Zhang, W., Gustafson, T. A., Rutter, W. J. & Johnson, J. D. (1994). Positively charged side chains in the insulin-like growth factor-1 C-and D-regions determine receptor binding specificity, J. Biol. Chem., 269, 10609-10613.

Zuckermann et al. (1994). J. Med. Chem., 37, 2678

TABLE 1

Amino acid sequence of human insulin receptor.
The sequence shown is that of the mature polypeptide,
Exon 11+ isoform, GENBANK reference NM 000208
(SEQ ID NO: 1). The residues shown in underlined bold
format are absent in the Exon 11- isoform.

HLYPGEVCPGMDIRNNL

TRLHELENCSVIEGHLQILLMFKTRPEDFRDLSFPKLIMITDYLLLFRVYGLESLKDL

FPNLTVIRGSRLFFNYALVIFEMVHLKELGLYNLMNITRGSVRIEKNNELCYLATIDW

SRILDSVEDNHIVLNKDDNEECGDICPGTAKGKTNCPATVINGQFVERCWTHSHCQKV

CPTICKSHGCTAEGLCCHSECLGNCSQPDDPTKCVACRNFYLDGRCVETCPPPYYHFQ

DWRCVNFSFCQDLHHKCKNSRRQGCHQYVIHNNKCIPECPSGYTMNSSNLLCTPCLGP

CPKVCHLLEGEKTIDSVTSAQELRGCTVINGSLIINIRGGNNLAAELEANLGLIEEIS

GYLKIRRSYALVSLSFFRKLRLIRGETLEIGNYSFYALDNQNLRQLWDWSKHNLTTTQ

GKLFFHYNPKLCLSEIHKMEEVSGTKGRQERNDIALKTNGDKASCENELLKFSYIRTS

FDKILLRWEPYWPPDFRDLLGFMLFYKEAPYQNVTEFDGQDACGSNSWTVVDIDPPLR

SNDPKSQNHPGWLMRGLKPWTQYAIFVKTLVTFSDERRTYGAKSDIIYVQTDATNPSV

PLDPISVSNSSSQIILKWKPPSDPNGNITHYLVFWERQAEDSELFELDYCLKGLKLPS

RTWSPPFESEDSQKHNQSEYEDSAGECCSCPKTDSQILKELEESSFRKTFEDYLHNVV

FVPRKTSSGTGAEDPRPSRKRRSLGDVGNVTVAVPTVAAFPNTSSTSVPTSPEEHRPF

EKVVNKESLVISGLRHFTGYRIELQACNQDTPEERCSVAAYVSARTMPEAKADDIVGP

VTHEIFENNVVHLMWQEPKEPNGLIVLYEVSYRRYGDEELHLCVSRKHFALERGCRLR

GLSPGNYSVRIRATSLAGNGSWTEPTYFYVTDYLDVPSNIAKIIIGPLIFVFLFSVVI

GSIYLFLRKRQPDGPLGPLYASSNPEYLSASDVFPCSVYVPDEWEVSREKITLLRELG

QGSFGMVYEGNARDIIKGEAETRVAVKTVNESASLRERIEFLNEASVMKGFTCHHVVR

LLGVVSKGQPTLVVMELMAHGDLKSYLRSLRPEAENNPGRPPPTLQEMIQMAAEIADG

MAYLNAKKFVHRDLAARNCMVAHDFTVKIGDFGMTRDIYETDYYRKGGKGLLPVRWMA

PESLKDGVFTTSSDMWSFGVVLWEITSLAEQPYQGLSNEQVLKFVMDGGYLDQPDNCP

ERVTDLMRMCWQFNPKMRPTFLEIVNLLKDDLHPSFPEVSFFHSEENKAPESEELEME

FEDMENVPLDRSSHCQREEAGGRDGGSSLGFKRSYEEHIPYTHMNGGKKNGRILTLPR

SNPS

TABLE 2

Effect of L1 domain mutations on IR and IGF-1R ligand binding affinity

| IR mutations[a] | Relative affinity to wild type receptor (%) | | | IGF-1R mutations | Relative affinity (%) |
|---|---|---|---|---|---|
| | IR-A isoform | IR-B isoform | IR patients | | |
| Arg14 | 0.1-0.5 | <1 | | Arg10 | 70-142 |
| Asn15 | 0.04-0.15 | <1 | | Asn11 | 14-27 |
| Asn15Lys | — | — | 20 | | |
| Phe64 | 0.04-0.15 | <1 | | Phe58 | 28-33 |
| Arg86Pro | — | — | <1% | — | — |
| Leu37 | 5 | 5 | | Leu33 | 17 |
| Phe39 | 4-10 | — | | Ser35 | 100 |
| Ile13 | 5-8 | — | | Ile9 | 100 |
| Glu34 | 7.6-9 | 8 | | His30 | 22 |
| Lys121 | 9 | 10.5 | | Lys115 | 300 |
| Asp12 | 10-15 | — | | Asp8 | 11-33 |
| Leu36 | 10-14 | | 14 | Leu32 | 77-100 |
| Leu87 | 11 | 14 | | Leu81 | 100 |
| Leu87Ile | — | — | 400 | — | |
| Leu87Pro | — | — | 15 | | |
| Glu97 | 11 | 12 | | Glu91 | 143 |
| Asn90 | 11-17 | 15 | | Asn84 | 67-300 |
| Phe89 | 20-22 | 17 | | Tyr83 | 100 |
| Tyr91 | 22-33 | 17 | | Tyr85 | 77-300 |
| Asp59Gly | — | — | 25% | | |
| Met38 | 28-33 | — | | Ile34 | — |
| Glu44 | 28-34 | — | | Glu38 | 67 |
| Glu120 | 29 | 29 | | Glu114 | 100 |
| Tyr67 | 31-43 | — | | Tyr61 | 77 |
| Phe88 | 40 | 43 | | Phe82 | 200 |
| His32 | 100 | 100 | | Tyr28 | 22 |
| Leu62 | 100 | 100 | | Leu56 | 20 |
| Arg65 | 100 | 100 | | Arg59 | 20 |
| Ser85 | 100 | 100 | | Trp79 | 33 |
| Phe96 | — | | | Phe90 | 4.5 |

[a]Mutations were to Ala except for the natural mutants which are indicated. Residues that differ between IR and IGF-1R are shaded. Data sources: Taylor et al. (1994), Gronskov et al. (1993) Williams et al. (1995), Mynarcik et al. (1996; 1997a; 1997b), Rouard et al. (1999) and Whittaker et al. (2001; 2002).

TABLE 3

Diffraction data and refinement statistics from IR ectodomain crystal IR IRΔβ.

| | Native #1 | PIP derivative | Native #2 |
|---|---|---|---|
| Beamline | IMCA-CAT 17-ID | IMCA-CAT 17-ID | PF BL5A |
| Wavelength (Å) | 1.2398 | 1.0707 | 1.0000 |
| Unit cell dimensions (Å) | 121.9, 316.8, 204.8 | 124.1, 316.8, 210.7 | 123.0, 319.7, 204.9 |
| Resolution range (Å) | 58.4-4.5 (4.66-4.50)[a] | 42.5-5.5 (5.70-5.50) | 47.4-3.8 (3.9-3.8) |
| Unique reflections | 23898 | 25936 | 41126 |
| Multiplicity | 7.13 (7.23) | 3.63 (3.30) | 5.24 (5.3) |
| $R_{merge}$[b] | 0.34 (0.733) | 0.271 (0.680) | 0.12 (0.7)[b] |
| $<I/\sigma(I)>$ | 2.9 (1.0) | 3.0 (1.2) | 5.8 (1.0) |
| Data completeness (%) | 99.8 (98.9) | 99.0 (99.0) | 99.9 (100.0) |
| Refinement resolution range (Å) | | | 12.0-3.8 (3.9-3.8) |
| $R_{work}$[c] (%) | | | 25.0 (26.4) |
| $R_{free}$[d] (%) | | | 29.4 (32.4) |
| Rms bonds (Å), angles (°) | | | 0.005, 1.094 |

[a]Values in parenthesis are for the highest shell.
[b]Rmerge = ΣhklΣj|Ij − <Ij>|/ΣhklΣj |Ij|, where hkl specifies unique indices, j indicates equivalent observations of hkl, and <Ij> is the mean value.
[c]R = Σhkl||Fo| − Fc|/Σhkl|Fo|, where |Fo| and |Fc| are the observed and calculated structure factor amplitudes, respectively.
[d]Represents approximately 5% of the data.

TABLE 4

Chromatographic procedures employed in the isolation of glycopeptides from hIR expressed in CHO-K1 cells.

| Isolation step | Peptide | N-linked site | Retention Time (min) | Column | Gradient Range (%) | Gradient Time (min) |
|---|---|---|---|---|---|---|
| CNBr | CN4 | 78 | 29.0-30.0 | Brownlee BU-300 | 5-50 | 30 |
| [a] | 2V-9 | 16 | 25.5-26.3 | C8 | 10-65 | 55 |
| [a] | 2V-9B | 16 | 17.2-19.0 | C8 | 15-45 | 36 |
| [b] | 2T-9 | 25 | 36.4-37.0 | C8 | 5-70 | 50 |
| [b] | 2T-10 | 25 | 37.0 37.5 | C8 | 5-70 | 50 |
| [c] initial | 3T-F | 742, 755 | 31.1-35.2 | C8 | 10-65 | 55 |
| [c] re-run | 3T-F | 742, 755 | 27.6-31.3 | C8 (45° C.) | 15-55 | 59 |
| [d] | 3T-F-Pep10 | 755 | 45.8-51.0 | C18b | 5-60 | 56 |
| [d] | 3T-F-Pep12 | 742 | 55.2-59.6 | C18b | 5-60 | 56 |
| [e] | 5AP-5 | 671 | 19.3-19.9 | C8 | 5-60 | 55 |
| [f] | 5T-12 | 893 | 22.1-22.6 | C8 | 5-100 | 60 |
| [g] | 5T-12-2 | 893 | 14.7-15.2 | C18b | 10-40 | 40 |
| [g] | 5T-12-3 | 893 | 16.3-16.9 | C18b | 10-40 | 40 |
| [f] | 5T-15 | 624 | 23.7-24.4 | C8 | 5-100 | 60 |
| [f] | 5T-15-7 | 624 | 16.8-17.8 | C18b | 15-60 | 45 |
| [f] | 5T-21 | 906 | 28.9-29.6 | C8 | 5-100 | 60 |

TABLE 4-continued

Chromatographic procedures employed in the isolation of glycopeptides from hIR expressed in CHO-K1 cells.

| Isolation step | Peptide | N-linked site | Retention Time (min) | Column | Gradient Range (%) | Gradient Time (min) |
|---|---|---|---|---|---|---|
| [f] | 5T-24 | 606 | 30.2-30.8 | C8 | 5-100 | 60 |
| [i] | 5T-24AspN-9 | 606 | 24.1-24.8 | C18a | 2-60 | 40 |
| [j] | 6AP-7,8 | 397 | 19.6-24.3 | Brownlee C4 (2.1 × 30 mm) | 5-100 | 45 |
| [k] | 6AP-7,8-7 | 397 | 33.2-34.3 | C8 | 10-60 | 47 |
| [l] | 6AP-7,8-7-4 | 397 | 19.0-20.0 | C18a | 23-50 | 34 |
| [m] | D | 111, 215, 255, 514 | 22.3-25.3 | C4 | 32-65 | 30 |
| [m] | H | 295, 418 | 43.2-45.8 | C4 | 32-65 | 30 |
| [n] | D-AspN-24 | 215, 514 | 36.8-37.7 | C8 | 5-70 | 66 |
| [o] | D-AspN-24C | 215, 514 | 18.4-18.8 | C8 | 23-40 | 21 |
| [n] | D-AspN-25 | 255 | 37.7-38.6 | C8 | 5-70 | 66 |
| [p] | D-AspN-25B | 255 | 16.2-16.9 | C8 | 26-41 | 19 |
| [n] | D-AspN-27 | 111 | 39.4-40.3 | C8 | 5-70 | 66 |
| [q] | D-AspN-27A | 111 | 12.5-13.8 | C8 | 30-42 | 15 |
| [r] | H-AspN-7 | 418 | 40.8-41.4 | C8 | 5-70 | 66 |
| [r] | H-AspN-8 | 295 | 43.1-44.5 | C8 | 5-70 | 66 |
| [s] | H-AspN-8-T7 | 295 | 26.3-28.0 | C8 | 5-70 | 30 |

Figure 13:
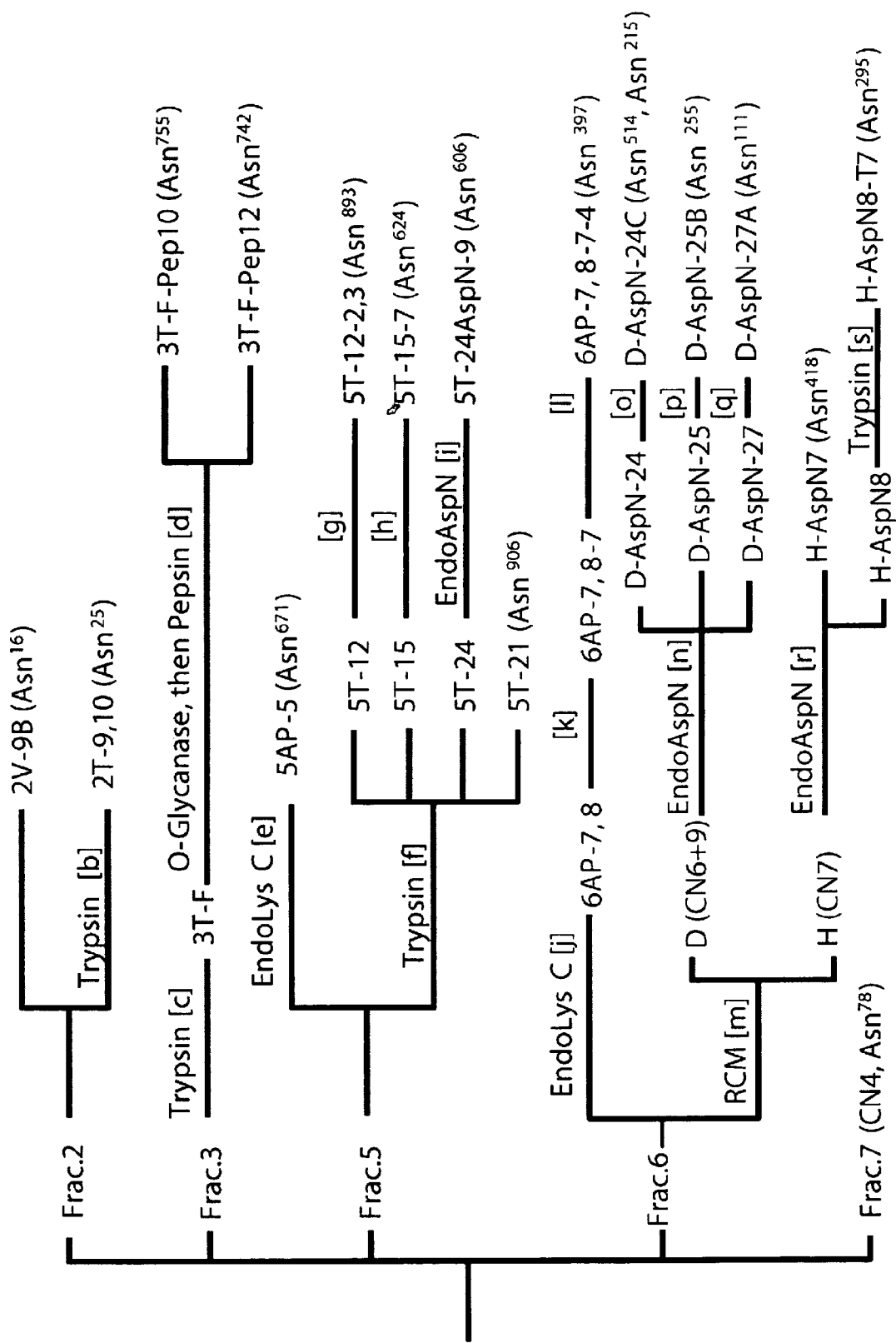
FIG. 13: Summary of the scheme for the isolation of N-linked glycopeptides from hIR ectodomain expressed in CHO-K1 cells. Enzyme digestions were carried out as described in the Experimental Procedures section described herein. The conditions for reversed-phase chromatographic isolation of each specific peptide are summarized in Table 4.

The strategy employed in the generation and isolation of the N-linked glycopeptides is summarised in FIG. 13. The fractionation of the CNBr digest of CHO-K1 expressed hIR is described in Sparrow et al. (1997). The letters [a] to [s] in this Table and FIG. 13 refer to the chromatographic separation employed for the various enzyme digests. Unless otherwise specified, all columns used were from Vydac (The Separations Group). The C8 column used was 2.1 × 150 mm and the C18a column was 2.1 × 50 mm; both were run at 0.2 ml/min. The C18b column was 1.0 × 150 mm and was run at 0.05 ml/min. The C4 column was 4.6 × 250 mm and was run at 1.0 ml/min. The Brownlee C4 column used was a cartridge, 2.1 × 30 mm. All chromatography was carried out at room temperature unless otherwise specified.

TABLE 5

Characterisation of glycopeptides from hIR ectodomain expressed in CHO-K1 cells

| Site | Peptide[a] | Sequence (Calculated Mass) | Mass Observed[a] | Glycan Mass (Calculated) | Glycan Type | Probable Composition[b] | Glycan Mass (Theoretical) | Abundance (%)[c] |
|---|---|---|---|---|---|---|---|---|
| 16 | 2V-9B | $D^{12}$-$E^{22}$ (1379.7)# | 3514.4 | 2134.7 | Complex | $GlcNAc_5Man_3Gal_3Fuc$ | 2133.8 | 6.4 |
| | | | 3149.3 | 1769.6 | Complex | $GlcNAc_4Man_3Gal_2Fuc$ | 1768.6 | 17.7 |
| | | | 3003.2 | 1622.7 | Complex | $GlcNAc_4Man_3Gal_2$ | 1622.6 | 12.3 |
| | | | 2962.2 | 1582.5 | Hybrid | $GlcNAc_3Man_5Gal$ | 1581.6 | 19.9 |
| | | | 2800.1 | 1420.4 | Hybrid | $GlcNAc_3Man_5$ | 1419.5 | 13.8 |
| | | | 2638.1 | 1258.4 | Complex | $GlcNAc_3Man_3Gal$ | 1257.4 | 9.7 |
| | | | 2597.0 | 1217.3 | High Man | $GlcNAc_2Man_5$ | 1216.4 | 20.1 |
| 25 | 2T-9 | $L^{20}$-$Hse^{38}$ (2161.5)* | 4589.6 | 2427.1 | Complex | $GlcNAc_5Man_3Gal_3FucNeuAc$ | 2426.2 | 9.0 |
| | | | 4297.7 | 2135.2 | Complex | $GlcNAc_5Man_3Gal_3Fuc$ | 2135.0 | 11.3 |
| | | | 4223.1 | 2060.6 | Complex | $GlcNAc_4Man_3Gal_2FucNeuAc$ | 2060.9 | 25.8 |
| | | | 3931.7 | 1769.2 | Complex | $GlcNAc_4Man_3Gal_2Fuc$ | 1768.6 | 53.9 |
| 78 | Fraction 7 | $I^{57}$-$Hse^{110}$ (6365.6)* | ND | ND | No Glycan[d] | No Glycan[d] | No Glycan[d] | 100 |
| 111 | D-AspN-27A | $N^{111}$-$I^{131d}$ (2465.8)* | 4331.6 | 1865.8 | High Man | $GlcNAc_2Man_9$ | 1865.7 | 62.9 |
| | | | 4169.8 | 1704.0 | High Man | $GlcNAc_2Man_8$ | 1703.5 | 20.6 |
| | | | 4007.6 | 1541.8 | High Man | $GlcNAc_2Man_7$ | 1541.4 | 10.6 |
| | | | 3845.9 | 1380.1 | High Man | $GlcNAc_2Man_6$ | 1379.2 | 5.8 |
| 215 | D-AspN 24C | $(D)^{175}$-$P^{222d}$ (5446.5)* | 6824.7 | 1378.2 | High Man | $GlcNAc_2Man_6$ | 1379.2 | 100 |
| 255 | D-AspN-25B | $D^{250}$-$Q^{260d}$ (1520.6)* | 3656.3 | 2135.7 | Complex | $GlcNAc_5Man_3Gal_3Fuc$ | 2135.0 | 1.4 |
| | | | 3582.3 | 2061.7 | Complex | $GlcNAc_4Man_3Gal_2FucNeuAc$ | 2060.9 | 6.3 |
| | | | 3290.8 | 1770.2 | Complex | $GlcNAc_4Man_3Gal_2Fuc$ | 1769.6 | 91.2 |
| | | | 3128.8 | 1608.2 | Complex | $GlcNAc_4Man_3GalFuc$ | 1607.5 | 0.7 |
| | | | 2927.0 | 1406.4 | Complex | $GlcNAc_3Man_3GalFuc$ | 1404.3 | 0.4 |
| 295 | H-AspN 8-T7 | $N^{295}$-$K^{310e}$ (1819.7)# | 4317.5 | 2497.8 | Complex | $GlcNAc_6Man_3Gal_4Fuc$ | 2498.9 | 12.9 |
| | | | 3952.5 | 2132.8 | Complex | $GlcNAc_5Man_3Gal_3Fuc$ | 2133.8 | 32.3 |
| | | | 3587.6 | 1767.9 | Complex | $GlcNAc_4Man_3Gal_2Fuc$ | 1768.6 | 54.8 |
| 337 | Not recovered | ND | ND | ND | NA | NA | NA | NA |
| 397 | 6AP-7,8-7-4 | $T^{392}$-$K^{416}$ | ND | NA | NA | NA | NA | NA |
| 397 | 6AP-7,8-7-4 | $T^{392}$-$K^{416}$ | ND | NA | NA | NA | NA | NA |
| 418 | H-AspN7 | $D^{413}$-$S^{437}$ (3037.4)* | 5537.3 | 2499.9 | Complex | $GlcNAc_6Man_3Gal_4Fuc$ | 2500.3 | 13.2 |
| | | | 5172.0 | 2134.6 | Complex | $GlcNAc_5Man_3Gal_3Fuc$ | 2135.0 | 36.7 |
| | | | 4806.9 | 1769.5 | Complex | $GlcNAc_4Man_3Gal_2Fuc$ | 1769.6 | 50.1 |
| 514 | D-AspN 24C | $L^{505}$-$F^{518}$ (1749.0)* | 3128.3 | 1379.3 | High Man | $GlcNAc_2Man_6$ | 1379.2 | 34.8 |
| | | | 2966.6 | 1217.6 | High Man | $GlcNAc_2Man_5$ | 1217.1 | 65.2 |

TABLE 5-continued

Characterisation of glycopeptides from hIR ectodomain expressed in CHO-K1 cells

| Site | Peptide[a] | Sequence (Calculated Mass) | Mass Observed[a] | Glycan Mass (Calculated) | Glycan Type | Probable Composition[b] | Glycan Mass (Theoretical) | Abundance (%)[c] |
|---|---|---|---|---|---|---|---|---|
| 606 | 5T-24 AspN 9 | $D^{600}$-$K^{614}$ (1587.8)* | 4089.2 | 2500.4 | Complex | $GlcNAc_6Man_3Gal_4Fuc$ | 2500.3 | 16.3 |
|  |  |  | 3724.0 | 2135.2 | Complex | $GlcNAc_5Man_3Gal_3Fuc$ | 2135.0 | 28.8 |
|  |  |  | 3358.8 | 1770.0 | Complex | $GlcNAc_4Man_3Gal_2Fuc$ | 1769.6 | 54.9 |
| 624 | 5T-15-7 | $W^{615}$-$Y^{628}$ (1625.8)* | 3764.3 | 2137.5 | Complex | $GlcNAc_5Man_3Gal_3Fuc$ | 2135.0 | 26.7 |
|  |  |  | 3618.1 | 1991.3 | Complex | $GlcNAc_5Man_3Gal_3$ | 1988.8 | 7.9 |
|  |  |  | 3398.2 | 1771.4 | Complex | $GlcNAc_4Man_3Gal_2Fuc$ | 1769.6 | 53.4 |
|  |  |  | 3252.1 | 1625.3 | Complex | $GlcNAc_4Man_3Gal_2$ | 1623.5 | 11.9 |
| 671 | 5AP-5 | $H^{670}$-$K^{687}$ (1984.1)* | 4486.8 | 2501.7 | Complex | $GlcNAc_6Man_3Gal_4Fuc$ | 2500.3 | 100 |
| 742 | 3T-F | Glycan only[f]# | NA[f] | 2280.5[f] | Complex | $GlcNAc_5Man_3Gal_3Fuc_2$ | 2279.8 | 11.0 |
|  |  |  |  | 2133.4[f] | Complex | $GlcNAc_5Man_3Gal_3Fuc$ | 2133.8 | 20.7 |
|  |  |  |  | 1768.6[f] | Complex | $GlcNAc4Man_3Gal_2Fuc$ | 1768.6 | 68.3 |
| 751 | 3T-F | Glycan only[f]# | NA[f] | 2133.5[f] | Complex | $GlcNAc_5Man_3Gal_3Fuc$ | 2133.8 | 18.3 |
|  |  |  |  | 1768.4[f] | Complex | $GlcNAc_4Man_3Gal_2Fuc$ | 1768.6 | 81.7 |
| 893 | 5T-12-2 | $G^{888}$-$Y^{894}$ | ND | NA | NA | NA | NA | NA |
| 893 | 5T-12-3 | $G^{888}$-$R^{897}$ (1049.2)* | 2447.2 | 1397.0 | High Man | $GlcNAc_2Man_6Na$ | 1402.2 | 100 |
| 906 | 5T-21 | $A^{900}$-$S^{925}$ | ND | NA | NA | NA | NA | NA |

[a]Glycopeptide masses obtained by mass spectrometry and used for subsequent calculations were either (*) average or (#) monoisotopic;
[b]probable glycan composition is based on the known structures of N-linked glycans found on proteins expressed in CHO cells (see Spellman et al., 1989);
[c]calculation of the relative abundance of each glycoform was based on peak heights in the corresponding mass spectrum;
[d]based on recovery of PTH-Asn in amino acid sequence analysis (see Table 6 for MS data on corresponding peptide from Lec8 expressed hIR ectodomain);
[e]Cys residues are as carboxymethyl-cysteine; NA = not applicable; ND = not determined;
[f]The peptides contained both O-linked and N-linked glycans. The N-linked glycans mass was determined after PNGase-release and derivitization with PMP.

Lengthy table referenced here

US08301398-20121030-T00001

Please refer to the end of the specification for access instructions.

Lengthy table referenced here

US08301398-20121030-T00002

Please refer to the end of the specification for access instructions.

Lengthy table referenced here

US08301398-20121030-T00003

Please refer to the end of the specification for access instructions.

Lengthy table referenced here

US08301398-20121030-T00004

Please refer to the end of the specification for access instructions.

LENGTHY TABLES

The patent contains a lengthy table section. A copy of the table is available in electronic form from the USPTO web site (http://seqdata.uspto.gov/?pageRequest=docDetail&DocID=US08301398B2). An electronic copy of the table will also be available from the USPTO upon request and payment of the fee set forth in 37 CFR 1.19(b)(3).

The invention claimed is:

1. A method of identifying a compound that binds insulin receptor (IR), comprising:
   (a) obtaining a crystal comprising IR selected from the group consisting of:
      (i) an orthorhombic crystal of IR ectodomain comprising a protein consisting of residues 1-485 of SEQ ID NO:1 in space group $P2_12_12_1$ having a cell unit dimension of a=103.86 Angstrom, b=130.24 Angstrom, and c=160.92 Angstrom, and
      (ii) an orthorhombic crystal of a complex consisting of IR-delta-beta (IRΔβ) of SEQ ID NO:15, Fab 83-7 of SEQ ID NOs:8 and 10, and Fab 83-14 of SEQ ID NOs:4 and 6 in space group $C222_1$ having a unit cell dimension of a=123.0 Angstrom, b=319.7 Angstrom, and c=204.9 Angstrom;
   (b) determining the three-dimensional structure of the IR by X-ray diffraction to obtain the atomic coordinates of Appendix I and or II;
   (c) contacting an IR structure defined by the atomic coordinates of Appendix I and/or Appendix II, or a subset thereof with a test compound; and detecting an interaction between the compound and the atomic coordinates, wherein an energetically favored interaction between the test compound and the atomic coordinates is indicative of a compound that binds IR.

2. The method of claim 1, comprising identifying a compound which interacts with the three-dimensional structure of: (i) IR ectodomain, the structure defined by the atomic coordinates shown in Appendix I, a subset of the atomic coordinates shown in Appendix I in combination with the atomic coordinates shown in Appendix II or a subset of the atomic coordinates shown in Appendix I in combination with a subset of the atomic coordinates shown in Appendix II; (ii) a region of IR ectodomain, the structure being defined by the atomic coordinates shown in Appendix II, or a subset of the atomic coordinates shown in Appendix I or Appendix II; (iii)

IR ectodomain as defined in (i) in combination with the atomic coordinates given in Appendix III and/or Appendix IV, or in combination with a subset of the atomic coordinates given in Appendix III and/or Appendix IV; or (iv) a region of IR ectodomain as defined in (ii) in combination with the atomic coordinates given in Appendix III and/or Appendix IV, or in combination with a subset of the atomic coordinates given in Appendix III and/or Appendix IV; wherein interaction of the compound with the structure is favored energetically.

3. The method according to claim 2, further comprising synthesising or obtaining an identified or designed candidate compound and determining the ability of the candidate compound to interact with IR.

4. The method according to claim 1, wherein the atomic coordinates define one or more regions as set forth in SEQ ID NO:1 from one or more of (i) from about residue 4 to 158 (the central β-sheet of L1), (ii) from about residue 159 to 310 (the central modules of CR), (iii) from about residue 471 to 593 (the AB loop of FnIII-1), (iv) from about residue 594 to 655 (the CC' loop of FnIII-1), (v) from about residue 759 to 807 (the EF loop of FnIII-1) and (vi) from about residue 808 to 909 (FnIII-2).

5. The method according to claim 4, wherein the atomic coordinates define the region including Phe39 in the $2^{nd}$ rung of the L1 face and the inserted loop comprising residues 86-91 in the $4^{th}$ rung of the L1 face of the central β-sheet of L1.

6. The method according to claim 4, wherein the atomic coordinates define the region of module 6 of the central modules of CR.

7. The method according to claim 1, wherein the structure defined by the atomic coordinates comprises a target binding site of IR ectodomain.

8. The method according to claim 7, wherein the atomic coordinates defining the target binding site define one or more regions defining the low affinity binding site for insulin.

9. The method according to claim 8, wherein the atomic coordinates define one or more regions from one or more of the L1 domain, the CT peptide and the CR domain.

10. The method according to claim 9, wherein the atomic coordinates define portions of the molecular surface of the central β-sheet of L1 and portions of the molecular surface of the second LRR which contain Phe39 and/or the loop in the fourth LRR rung of L1.

11. The method according to claim 9, wherein the atomic coordinates define module 6 of the CR domain.

12. The method according to claim 8, wherein the atomic coordinates define one or more amino acids selected from IR amino acid residues 1-156, 704-719 and 157-310.

13. The method according to claim 12, wherein the atomic coordinates define at least one amino acid selected from Arg14, Asn15, Gln34, Leu36, Leu37, Phe39, Pro43-Phe46, Phe64, Leu87, Phe88, Asn90 and Phe89.

14. The method according to claim 7, wherein the target binding site comprises one or more regions defining the high affinity binding site for insulin.

15. The method according to claim 14, wherein the atomic coordinates define one or more regions of the IR ectodomain selected from regions of the FnIII-1 domain.

16. The method according to claim 15, wherein the atomic coordinates define one or more regions selected from one or more of the AB loop of FnIII-1, the CC' loop of FnIII-1 and the EF loop of FnIII-1.

17. The method according to claim 14, wherein the atomic coordinates define one or more amino acids selected from IR amino acid residues 472-594, 475-489, 508-536 and 550-569.

18. A method of identifying a compound that binds insulin-like growth factor 1 receptor (IGF-1R), comprising:
(a) obtaining a crystal comprising IR selected from the group consisting of:
(i) an orthorhombic crystal of IR ectodomain comprising a protein consisting of residues 1-485 of SEQ ID NO:1 in space group $P2_12_12_1$ having a cell unit dimension of a=103.86 Angstrom, b=130.24 Angstrom, and c=160.92 Angstrom, and
(ii) an orthorhombic crystal of a complex consisting of IR-delta-beta (IRΔβ) of SEQ ID NO:15, Fab 83-7 of SEQ ID NOs:8 and 10, and Fab 83-14 of SEQ ID NOs:4 and 6 in space group $C222_1$ having a unit cell dimension of a=123.0 Angstrom, b=319.7 Angstrom, and c=204.9 Angstrom;
(b) determining the three-dimensional structure of the IR by X-ray diffraction to obtain the atomic coordinates of Appendix I and or II; and
(c) contacting an IR structure defined by the atomic coordinates of Appendix I and/or Appendix II, or a subset thereof with a test compound; and detecting an interaction between the compound and the atomic coordinates, wherein an energetically favored interaction between the test compound and the atomic coordinates is indicative of a compound that binds IGF-1R.

19. The method according to claim 18, wherein a candidate compound for interacting with IGF-1R is chemically modified as a result of the structure-based evaluation.

20. The method according to claim 19, wherein the chemical modification is designed to reduce the potential for the candidate compound to bind to IR.

21. An orthorhombic crystal of IR ectodomain comprising a protein consisting of residues 1-485 of SEQ ID NO:1 in space group $P2_12_12_1$ having a cell unit dimension of a=103.86 Angstrom, b=130.24 Angstrom, and c=160.92 Angstrom with up to 2% variation in any cell dimension.

22. An orthorhombic crystal of a complex consisting of IR-delta-beta (IRΔβ) of SEQ ID NO:15, Fab 83-7 of SEQ ID NOs:8 and 10, and Fab 83-14 of SEQ ID NOs:4 and 6 in space group $C222_1$ having a unit cell dimension of a=123.0 Angstrom, b=319.7 Angstrom, and c=204.9 Angstrom with up to 2% variation in any cell dimension.

23. The method of claim 1, wherein the method is performed using a computer system.

24. The method of claim 18, wherein the method is performed using a computer system.

* * * * *